(12) United States Patent
Viswanathan et al.

(10) Patent No.: US 12,257,080 B2
(45) Date of Patent: *Mar. 25, 2025

(54) SYSTEMS, APPARATUSES, AND METHODS FOR FILTERING HIGH VOLTAGE NOISE INDUCED BY PULSED ELECTRIC FIELD ABLATION

(71) Applicant: Boston Scientific Scimed, Inc., Maple Grove, MN (US)

(72) Inventors: Raju Viswanathan, Mountain View, CA (US); William Bowers, Westminster, CO (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 532 days.

This patent is subject to a terminal disclaimer.

(21) Appl. No.: 17/340,745

(22) Filed: Jun. 7, 2021

(65) Prior Publication Data
US 2021/0290172 A1    Sep. 23, 2021

Related U.S. Application Data

(63) Continuation of application No. 17/091,289, filed on Nov. 6, 2020, now Pat. No. 11,033,236, which is a
(Continued)

(51) Int. Cl.
*A61B 18/12* (2006.01)
*A61B 5/00* (2006.01)
(Continued)

(52) U.S. Cl.
CPC ............ *A61B 5/7217* (2013.01); *A61B 5/305* (2021.01); *A61B 5/308* (2021.01);
(Continued)

(58) Field of Classification Search
CPC ............ A61B 18/1206; A61B 18/1293; A61B 18/1492; A61B 2018/1293; A61B 2018/00839; A61B 2018/00351
See application file for complete search history.

(56) References Cited

U.S. PATENT DOCUMENTS 3,683,923 A    8/1972   Anderson
4,092,986 A    6/1978   Schneiderman
(Continued)

FOREIGN PATENT DOCUMENTS

CN    105283143 A    1/2016
EP    1042990 A1    10/2000
(Continued)

OTHER PUBLICATIONS

First Office Action for Chinese Application No. 201680077941.2, dated Jun. 30, 2020, 13 pages.
(Continued)

*Primary Examiner* — Daniel W Fowler
(74) *Attorney, Agent, or Firm* — Nelson Mullins Riley & Scarborough LLP

(57) ABSTRACT

Systems, apparatuses, and methods for electroporation ablation therapy are disclosed, with a protection device for protecting electronic circuitry, devices, and/or other components from induced currents and voltages generated during a cardiac ablation procedure. A system can include an ablation device near cardiac tissue of a heart. The system can further include a signal generator configured to generate a pulse waveform, where the signal generator coupled to the ablation device and configured to repeatedly deliver the pulse waveform to the ablation device in synchrony with a set of cardiac cycles of the heart. The system can further
(Continued)

include a protection device configured to suppress induced current and voltage in an electronic device coupled to the protection device.

20 Claims, 26 Drawing Sheets

Related U.S. Application Data continuation of application No. PCT/US2019/030922, filed on May 6, 2019.

(60) Provisional application No. 62/667,887, filed on May 7, 2018.

(51) Int. Cl.
  *A61B 5/305* (2021.01)
  *A61B 5/308* (2021.01)
  *A61B 18/00* (2006.01)
  *A61B 18/14* (2006.01)
  *A61N 1/37* (2006.01)

(52) U.S. Cl.
  CPC ............ *A61B 18/1206* (2013.01); *A61B 2018/00351* (2013.01); *A61B 2018/00577* (2013.01); *A61B 2018/00839* (2013.01); *A61B 2018/1293* (2013.01); *A61B 18/1492* (2013.01); *A61N 1/3718* (2013.01)

(56) References Cited

U.S. PATENT DOCUMENTS

| | | |
|---|---|---|
| 4,200,104 A | 4/1980 | Harris |
| 4,429,694 A | 2/1984 | McGreevy |
| 4,438,766 A | 3/1984 | Bowers |
| 4,470,407 A | 9/1984 | Hussein |
| 4,739,759 A | 4/1988 | Rexroth et al. |
| 4,919,508 A | 4/1990 | Grace et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,293,868 A | 3/1994 | Nardella |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,509,411 A * | 4/1996 | Littmann ............ A61B 5/6852 600/585 |
| 5,515,848 A | 5/1996 | Corbett, III et al. |
| 5,531,685 A | 7/1996 | Hemmer et al. |
| 5,545,161 A | 8/1996 | Imran |
| 5,558,091 A | 9/1996 | Acker et al. |
| 5,578,040 A | 11/1996 | Smith |
| 5,617,854 A | 4/1997 | Munsif |
| 5,624,430 A | 4/1997 | Eton et al. |
| 5,662,108 A | 9/1997 | Budd et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,016,452 A * | 1/2000 | Kasevich ............ A61B 18/1206 606/49 |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,504 B1 * | 9/2002 | Ben-Haim ............ A61B 34/20 606/15 |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |

(56) References Cited

U.S. PATENT DOCUMENTS

| | | |
|---|---|---|
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,810,241 B1 | 10/2004 | Salib |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Christian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,010,186 B1 | 8/2011 | Ryu et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |

(56) References Cited

U.S. PATENT DOCUMENTS

| | | |
|---|---|---|
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,788,885 B2 | 10/2017 | Long et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,117,701 B2 | 11/2018 | Davalos et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,292,755 B2 | 5/2019 | Arena et al. |
| 10,322,286 B2 | 6/2019 | Viswanathan et al. |
| 10,342,598 B2 | 7/2019 | Long et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 10,531,914 B2 | 1/2020 | Stewart et al. |
| 10,625,080 B1 | 4/2020 | Viswanathan |
| 10,688,305 B1 | 6/2020 | Viswanathan |
| 10,709,502 B2 | 7/2020 | Viswanathan |
| 10,709,891 B2 | 7/2020 | Viswanathan et al. |
| 10,842,572 B1 | 11/2020 | Viswanathan |
| 11,033,236 B2 | 6/2021 | Viswanathan et al. |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0078494 A1 | 4/2003 | Panescu et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0122494 A1* | 6/2004 | Eggers .................. A61B 18/04 607/103 |
| 2004/0147920 A1 | 7/2004 | Keidar |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0091970 A1 | 5/2006 | Mondal |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0021803 A1* | 1/2007 | Deem .................. A61N 1/05 607/46 |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0191830 A1* | 8/2007 | Crompton, Jr. ........ A61B 18/14 606/41 |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |

(56) References Cited

U.S. PATENT DOCUMENTS

| | | |
|---|---|---|
| 2009/0069799 A1* | 3/2009 | Daw .................. A61B 18/1206 606/33 |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0192441 A1* | 7/2009 | Gelbart ................ A61B 5/0538 604/22 |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306641 A1* | 12/2009 | Govari .................. A61N 1/362 607/9 |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0134273 A1 | 6/2010 | Weiss et al. |
| 2010/0135550 A1 | 6/2010 | Arnon |
| 2010/0137861 A1 | 6/2010 | Soroff et al. |
| 2010/0168550 A1 | 7/2010 | Byrd et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0015628 A1 | 1/2011 | Dalal et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0043297 A1* | 2/2011 | Stevenson ............ G01R 33/285 333/12 |
| 2011/0071513 A1* | 3/2011 | Shin .................. A61B 18/1206 606/33 |
| 2011/0098694 A1 | 4/2011 | Long |
| 2011/0098699 A1 | 4/2011 | Pachon et al. |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0202051 A1 | 8/2011 | Hagg et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0109242 A1 | 5/2012 | Levin et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0066913 A1* | 3/2014 | Sherman ............ A61B 18/1492 606/41 |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2014/0378958 A1 | 12/2014 | Eussler |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0080693 A1 | 3/2015 | Solis |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |

(56) References Cited

U.S. PATENT DOCUMENTS

| | | |
|---|---|---|
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0223902 A1 | 8/2015 | Walker et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0327944 A1 | 11/2015 | Neal, II et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0078170 A1 | 3/2018 | Panescu et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0145595 A1 | 5/2018 | Fontana et al. |
| 2018/0168511 A1 | 6/2018 | Hall et al. |
| 2018/0184982 A1 | 7/2018 | Basu et al. |
| 2018/0193090 A1 | 7/2018 | de la Rama et al. |
| 2018/0200497 A1 | 7/2018 | Mickelsen |
| 2018/0214195 A1 | 8/2018 | Fraasch et al. |
| 2018/0214202 A1 | 8/2018 | Howard et al. |
| 2018/0221078 A1 | 8/2018 | Howard et al. |
| 2018/0221085 A1 | 8/2018 | Blanck et al. |
| 2018/0243558 A1 | 8/2018 | Athos et al. |
| 2018/0250508 A1 | 9/2018 | Howard |
| 2018/0289417 A1 | 10/2018 | Schweitzer et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0038171 A1 | 2/2019 | Howard |
| 2019/0060632 A1 | 2/2019 | Asirvatham et al. |
| 2019/0069950 A1 | 3/2019 | Viswanathan et al. |
| 2019/0125439 A1 | 5/2019 | Rohl et al. |
| 2019/0151015 A1 | 5/2019 | Viswanathan et al. |
| 2019/0183378 A1 | 6/2019 | Mosesov et al. |
| 2019/0192223 A1 | 6/2019 | Rankin |
| 2019/0201089 A1 | 7/2019 | Waldstreicher et al. |
| 2019/0209238 A1 | 7/2019 | Jimenez |
| 2019/0223938 A1 | 7/2019 | Arena et al. |
| 2019/0223950 A1 | 7/2019 | Gelbart et al. |
| 2019/0231421 A1 | 8/2019 | Viswanathan et al. |
| 2019/0231425 A1 | 8/2019 | Waldstreicher et al. |
| 2019/0233809 A1 | 8/2019 | Neal, II et al. |
| 2019/0256839 A1 | 8/2019 | Neal, II et al. |
| 2019/0269912 A1 | 9/2019 | Viswanathan et al. |
| 2019/0328445 A1 | 10/2019 | Sano et al. |
| 2019/0336198 A1 | 11/2019 | Viswanathan et al. |
| 2019/0336207 A1 | 11/2019 | Viswanathan |
| 2019/0350647 A1 | 11/2019 | Ramberg et al. |
| 2019/0376055 A1 | 12/2019 | Davalos et al. |
| 2020/0129233 A1 | 4/2020 | Viswanathan et al. |
| 2020/0139114 A1 | 5/2020 | Viswanathan et al. |
| 2020/0230403 A1 | 7/2020 | Bowers |
| 2021/0022794 A1 | 1/2021 | Viswanathan |
| 2021/0077030 A1 | 3/2021 | Viswanathan et al. |
| 2021/0077816 A1 | 3/2021 | Viswanathan |
| 2021/0121230 A1 | 4/2021 | Viswanathan |
| 2021/0145503 A1 | 5/2021 | Pare et al. |

FOREIGN PATENT DOCUMENTS

| | | |
|---|---|---|
| EP | 1125549 | 8/2001 |
| EP | 0797956 | 6/2003 |
| EP | 1127552 | 6/2006 |
| EP | 1340469 | 3/2007 |

(56) References Cited

FOREIGN PATENT DOCUMENTS

| | | |
|---|---|---|
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 3287090 A1 | 2/2018 |
| EP | 2382935 B1 | 3/2018 |
| EP | 3111871 B1 | 3/2018 |
| EP | 3151773 B1 | 4/2018 |
| EP | 3056242 B1 | 7/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| JP | 2015-524732 | 8/2015 |
| JP | 2015-532604 | 11/2015 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2008/035070 | 3/2008 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/036439 | 3/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/140741 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/024123 | 2/2017 |
| WO | WO 2017/093926 | 6/2017 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/005511 | 1/2018 |
| WO | WO 2018/200800 | 11/2018 |
| WO | WO 2018/208795 | 11/2018 |
| WO | WO 2019/118436 | 6/2019 |
| WO | WO 2019/133606 | 7/2019 |
| WO | WO 2019/133608 | 7/2019 |
| WO | WO 2019/147832 | 8/2019 |
| WO | WO 2019/152986 | 8/2019 |
| WO | WO 2019/173309 | 9/2019 |
| WO | WO 2019/217317 | 11/2019 |
| WO | WO 2019/217433 | 11/2019 |

OTHER PUBLICATIONS

Extended European Search Report for European Application No. 16884132.8, mailed Jul. 8, 2019, 7 pages.
Notice of Reasons for Rejection for Japanese Application No. 2018-534869, mailed Jul. 29, 2020, 11 pages.
Office Action for U.S. Appl. No. 15/334,646, mailed Jul. 25, 2017, 19 pages.
Office Action for U.S. Appl. No. 15/334,646, mailed Nov. 16, 2017, 26 pages.
International Search Report and Written Opinion for International Application No. PCT/US2016/057664, mailed Feb. 24, 2017, 11 pages.
Office Action for U.S. Appl. No. 15/796,375, mailed Jan. 24, 2018, 25 pages.
Office Action for U.S. Appl. No. 15/796,375, mailed May 30, 2018, 26 pages.
Office Action for U.S. Appl. No. 15/796,375, mailed Nov. 16, 2018, 27 pages.
Office Action for U.S. Appl. No. 16/416,677, mailed Aug. 15, 2019, 8 pages.
Office Action for U.S. Appl. No. 16/722,650, mailed Mar. 25, 2020, 12 pages.
Office Action for U.S. Appl. No. 15/499,804, mailed Jan. 3, 2018, 20 pages.
Office Action for U.S. Appl. No. 15/794,717, mailed Feb. 1, 2018, 10 pages.
International Search Report and Written Opinion for International Application No. PCT/US2018/029552, mailed Jun. 29, 2018, 13 pages.
International Search Report and Written Opinion for International Application No. PCT/US2019/017322, mailed May 10, 2019, 15 pages.
International Search Report and Written Opinion for International Application No. PCT/US2019/030922, mailed Sep. 6, 2019, 12 pages.
Office Action for U.S. Appl. No. 16/573,704, mailed Dec. 17, 2019, 6 pages.
Office Action for U.S. Appl. No. 16/741,506, mailed Feb. 28, 2020, 5 pages.
Office Action for U.S. Appl. No. 16/689,967, mailed Jul. 22, 2020, 23 pages.
Office Action for U.S. Appl. No. 16/405,515, mailed Sep. 6, 2019, 9 pages.
International Search Report and Written Opinion for International Application No. PCT/US2019/031135, mailed Aug. 5, 2019, 11 pages.
Office Action for U.S. Appl. No. 16/723,407, mailed Mar. 19, 2020, 13 pages.

(56) References Cited

OTHER PUBLICATIONS

Office Action for U.S. Appl. No. 16/785,392, mailed May 29, 2020, 18 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Tekle, E. et al., "Electroporation by using bipolar oscillating electric field: An improved method for DNA transfection of NIH 3T3 cells," Proc. Natl. Acad. Sci. USA, vol. 88, pp. 4230-4234, May 1991.
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Second Office Action for Chinese Application No. 201680077941.2, dated Apr. 2, 2021, 15 pages.
Office Action for European Application No. 16884132.8, mailed Apr. 12, 2021, 4 pages.
Office Action for U.S. Appl. No. 17/091,289, mailed Jan. 26, 2021, 18 pages.
International Search Report and Written Opinion for International Application No. PCT/US2020/051272, mailed Jan. 22, 2021, 10 pages.
Office Action for U.S. Appl. No. 16/689,967, mailed Dec. 22, 2020, 16 pages.
International Search Report and Written Opinion for International Application No. PCT/US2020/061564, mailed Mar. 12, 2021, 14 pages.
International Search Report and Written Opinion for International Application No. PCT/US2020/061809, mailed Mar. 18, 2021, 12 pages.

* cited by examiner

SYSTEMS, APPARATUSES, AND METHODS FOR FILTERING HIGH VOLTAGE NOISE INDUCED BY PULSED ELECTRIC FIELD ABLATION

CROSS-REFERENCE TO RELATED APPLICATIONS

This application is a continuation of U.S. application Ser. No. 17/091,289, filed on Nov. 6, 2020, which is a continuation of International Application No. PCT/US2019/030922, filed on May 6, 2019, which claims the benefit of U.S. Provisional Application No. 62/667,887, filed on May 7, 2018, the entire disclosure of each of which is incorporated herein by reference in its entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high direct current (DC) voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death). Subsequently, the surrounding tissue may heal naturally. High DC voltage pulses, however, may cause complications (e.g., ventricular fibrillation) if delivered during certain periods of cardiac activity.

For example, to avoid the risk of inducing arrhythmias, high voltage pulses may be applied in synchrony with a cardiac cycle of a subject. For example, high voltage pulses can be applied during specific periods of the cardiac cycle. In some applications, a cardiac stimulator can be used to stimulate the cardiac chamber(s) of a subject to establish periodicity of electrocardiogram (ECG) activity of the heart. Other devices, e.g., sensing and/or mapping systems, can also be used to monitor a subject's cardiac cycle. When these devices are used during a pulsed electric field ablation procedure, however, they can become exposed to high voltages. Such exposure can result in induced currents that can disrupt the operation of the devices. Accordingly, it can be desirable to have systems, apparatuses, and methods for addressing this issue.

SUMMARY

Described herein are systems, devices, and methods for protecting electronic circuitry, devices, and/or other components from induced currents during pulsed electric field ablation procedures. In some embodiments, the ablation devices used in these systems may be deployed epicardially or endocardially in cardiac applications. The pulsed waveforms may include predetermined parameters or may be automatically generated by a signal generator.

In some embodiments, a system may comprise a set of electrodes disposable near tissue of a subject. A signal generator may be configured to generate a voltage pulse waveform, the signal generator coupleable to the set of electrodes and configured to deliver the voltage pulse waveform to the set of electrodes to ablate the tissue. The set of electrodes may be configured to induce currents in a first electronic device disposed near the cardiac tissue in response to receiving the voltage pulse waveform. A protection device may be coupleable between the first electronic device and a second electronic device. The protection device may be configured to reduce the currents induced in the first electronic device.

In some embodiments, the first electronic device is a pacing device including a set of leads, and the second electronic device is a cardiac stimulator configured to deliver pacing signals to the pacing device. In some embodiments, the currents induced in the first electronic device include one or more of common mode currents or differential mode currents. The protection device may include one or more transformers configured to reduce the common mode currents or the differential mode currents.

In some embodiments, each transformer of the one or more transformers includes a toroid core, a first winding around a first portion of the toroid core, and a second winding around a second portion of the toroid core. In some embodiments, the protection device includes one or more capacitors configured to shunt currents above a predetermined frequency to reduce the currents induced in the first electronic device. In some embodiments, the protection device includes one or more diodes configured to shunt high voltages away from the second electronic device. In some embodiments, the protection device includes one or more inductors configured to reduce alternating currents induced in the first electronic device. In some of these embodiments, the one or more inductors includes a first inductor coupled to a first lead of the first electronic device and a second inductor coupled to a second lead of the first electronic device. The first and second inductors may be configured to reduce alternating currents induced in the first and second leads.

In some embodiments, the protection device includes first and second capacitors each configured to short voltages above a predetermined frequency, a first transformer coupled between the first electronic device and the first capacitor, a second transformer coupled between the first capacitor and the second capacitor. The first and second transformers may be configured to reduce common mode currents or differential mode currents induced in the first electronic device. A set of diodes may be arranged in parallel with the second capacitor and coupled to the second electronic device. The set of diodes may be configured to shunt high voltages away from the second electronic device. In some of these embodiments, the first and second transformers each are common mode transformers configured to reduce common mode currents induced in the first electronic device. In some of these embodiments, one of the first and second transformers is a differential mode transformer configured to reduce differential mode currents induced in the first electronic device. The other of the first and second transformers is a common mode transformer configured to reduce common mode currents induced in the first electronic device.

In some embodiments, the protection device includes one or more balun circuits configured to reduce common mode currents induced in the first electronic device over a predetermined frequency range. In some of these embodiments, the one or more balun circuits includes a plurality of balun circuits each configured to reduce common mode currents induced in the first electronic device over a predetermined frequency range of a set of predetermined frequency ranges. Each predetermined frequency range of the set of predetermined frequency ranges at least partially overlapping at least one other predetermined frequency range of the set of predetermined frequency ranges. In some of these embodiments, the protection device includes one or more inductors configured to reduce alternating currents induced in the first electronic device. The one or more balun circuits may be coupled between the one or more inductors and the second electronic device.

In some embodiments, at least one balun circuit of the one or more balun circuits may include an inductor in parallel with a capacitor and a resistor. In some embodiments, at least one balun circuit of the one or more balun circuits includes a coaxial cable winding including first and second conductors. The first conductor may be coupled to a first lead of the first electronic device and the second conductor may be coupled to a second lead of the first electronic device. In some embodiments, the one or more balun circuits includes a plurality of balun circuits connected in series. In some embodiments, the protection device is further coupled between the first electronic device and the signal generator. In some embodiments, the protection device is integrated into at least one of the signal generator and the second electronic device.

In some embodiments, an apparatus may comprise a protection device coupleable between a first electronic device and a second electronic device, the first electronic device disposable near cardiac tissue of a subject such that currents can be induced in the first electronic device by voltage pulse waveforms delivered to a set of electrodes near tissue. The protection device may include a set of capacitors each configured to shunt currents above a predetermined frequency to reduce the currents induced in the first electronic device. A set of transformers may each be configured to reduce common mode currents or differential mode currents of the currents induced in the first electronic device. A set of diodes may be configured to shunt high voltages away from the second electronic device.

In some embodiments, a signal generator may be configured to generate the voltage pulse waveform. The signal generator may be coupled to the set of electrodes and configured to deliver the voltage pulse waveform to the set of electrodes. A cardiac stimulator may be configured to deliver pacing signals to the first electronic device, the cardiac stimulator being the second electronic device. In some embodiments, the first electronic device may be a pacing device including a set of leads, and the second electronic device may be a cardiac stimulator configured to deliver pacing signals to the pacing device.

In some embodiments, each transformer of the one or more transformers includes a toroid core, a first winding around a first portion of the toroid core, and a second winding around a second portion of the toroid core. In some of these embodiments, the toroid core of each transformer of the one or more transformers includes a set of laminations having an aspect ratio of less than or equal to five. In some embodiments, the toroid core of each transformer of the one or more transformers defines a central axis with the first winding of that transformer winding around the central axis of the toroid core in a first direction and the second winding of that transformer winding around the central axis in a second direction opposite the first direction. In some embodiments, an outer radius of the toroid core of each transformer of the one or more transformers is between about 4 cm and about 10 cm, and an inner radius of the toroid core of each transformer of the one or more transformers is between about 2 cm and about 9 cm. In some embodiments, a thickness of the toroid core of each transformer of the one or more transformers may be between about 1 cm and about 6 cm.

In some embodiments, each transformer of the one or more transformers may include an inductance of at least about 1 milliHenry and a resistance of at least about 500 Ohms. In some embodiments, each diode of the set of diodes may be a Zener diode. In some embodiments, the set of diodes includes first and second diodes arranged in series facing opposite directions. In some embodiments, the set of diodes may be arranged in parallel to at least one capacitor of the set of capacitors.

In some embodiments, the set of capacitors includes first and second capacitors. The set of transformers includes a first transformer coupled between the first electronic device and the first capacitor. A second transformer may be coupled between the first capacitor and the second capacitor. The set of diodes includes first and second diodes coupled to the second electronic device. In some of these embodiments, the first and second transformers may each be common mode transformers configured to reduce common mode currents of the currents induced in the first electronic device. In some embodiments, one of the first and second transformers may be a differential mode transformer configured to reduce differential mode currents of the currents induced in the first electronic device, and the other of the first and second transformers is a common mode transformer configured to reduce common mode currents of the currents induced in the first electronic device. In some embodiments, the protection device may include one or more inductors configured to reduce alternating currents induced in the first electronic device.

In some embodiments, an apparatus may comprise a protection device coupleable between a first electronic device and a second electronic device, the first electronic device disposable near tissue of a subject such that currents can be induced in the first electronic device by voltage pulse waveforms delivered to a set of electrodes near the cardiac tissue. The protection device may include a set of balun circuits connected in series and collectively configured to reduce the currents induced in the first electronic device over a set of predetermined frequency ranges.

In some embodiments, a signal generator may be configured to generate the voltage pulse waveform, the signal generator coupled to the set of electrodes and configured to deliver the voltage pulse waveform to the set of electrodes. In some embodiments, a cardiac stimulator may be configured to deliver pacing signals to the first electronic device, the cardiac stimulator being the second electronic device. In some embodiments, the first electronic device may be a pacing device including a set of leads, and the second electronic device is a cardiac stimulator configured to deliver pacing signals to the pacing device. In some embodiments, each predetermined frequency range of the set of predetermined frequency ranges may at least partially overlap at least one other predetermined frequency range of the set of predetermined frequency ranges. In some embodiments, each predetermined frequency range of the set of predetermined frequency ranges may have a resonance peak associated with a balun circuit of the set of balun circuits.

In some embodiments, the protection device may further include one or more inductors configured to reduce an alternating current of the currents induced in the first electronic device. In some of these embodiments, the set of balun circuits may be coupled between the one or more inductors and the first electronic device. In some of these embodiments, the one or more inductors may include first and second sets of inductors. The first set of inductors may be coupled between the set of balun circuits and the first electronic device. The second set of inductors may be coupled between the set of balun circuits and the second electronic device.

In some embodiments, at least one balun circuit of the set of balun circuits may include an inductor in parallel with a capacitor and a resistor. In some embodiments, at least one balun circuit of the set of balun circuits includes a coaxial cable winding including first and second conductors. The first conductor may be coupled to a first lead of the first electronic device and the second conductor coupled to a second lead of the first electronic device.

In some embodiments, a method may comprise delivering, using a pacing device positioned near cardiac tissue of a heart, pacing signals to the heart; delivering, using a signal generator, voltage pulse waveforms to an ablation device positioned near the cardiac tissue to ablate the cardiac tissue; inducing, in response to delivering the voltage pulse waveform, currents in a set of first electronic devices positioned near the cardiac tissue, the set of first electronic devices including the pacing device; reducing, using a protection device coupled between the set of first electronic devices and a second electronic device, the currents induced in the set of first electronic devices.

In some embodiments, the second electronic device may be a cardiac stimulator configured to generate the pacing signals. In some embodiments, the second electronic device may be an electrocardiogram (ECG) recording system. In some embodiments, the method may further comprise reducing, using the protection device, the current induced in the set of first electronic devices includes reducing, using one or more transformers or capacitors of the protection device, common mode currents or differential mode currents of the currents induced in the set of first electronic devices. In some embodiments, reducing, using the protection device, the current induced in the set of first electronic devices includes shunting, using a set of diodes of the protection device, high voltages away from the second electronic device. In some embodiments, reducing, using the protection device, the current induced in the set of first electronic devices includes reducing, using one or more inductors of balun circuits of the protection device, alternating currents having frequencies within a predetermined range of frequencies of the currents induced in the set of first electronic devices. In some embodiments, reducing, using the protection device, the current induced in the set of first electronic devices includes reducing, using one or more inductors of balun circuits of the protection device, alternating currents having frequencies within a predetermined range of frequencies of the currents induced in the set of first electronic devices.

The pulse waveforms of the present invention may be hierarchical in organization and have a nested structure. Further, they involve a sequence of groupings with a variety of associated timescales. Furthermore, the associated timescales and pulse widths, and the numbers of pulses and hierarchical groupings, may be selected so as to satisfy one or more of a set of Diophantine inequalities involving the frequency of cardiac pacing.

DETAILED DESCRIPTION

Figure 1:
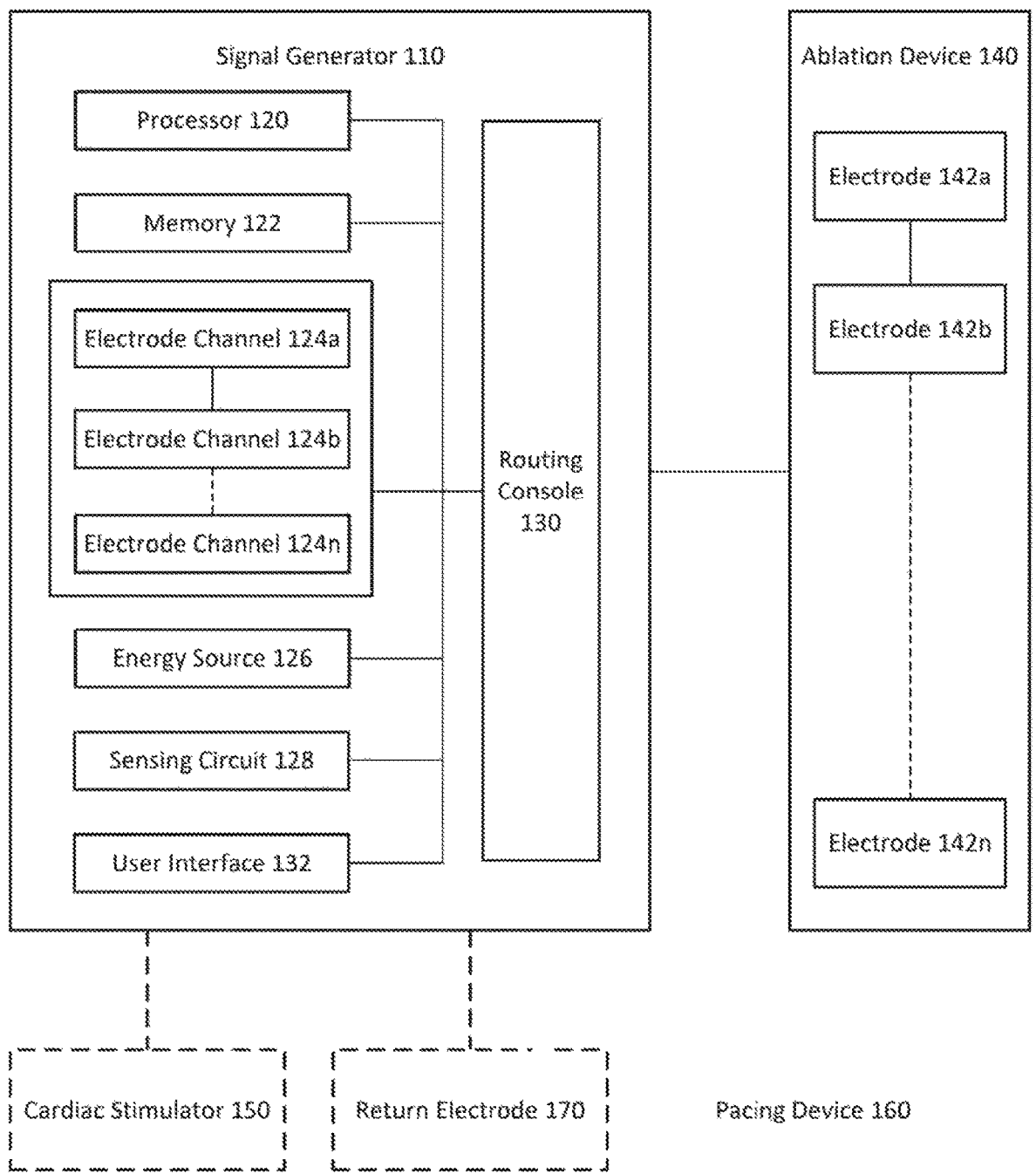
FIG. 1 is a block diagram of an electroporation system, according to embodiments.

Described herein are systems, devices, and methods for protecting circuits from high power noise induced during pulsed electric field ablation, e.g., pulsed electric fields to ablate tissue by irreversible electroporation. Generally, pulsed electric field systems may be used to generate large electric field magnitudes (e.g., electric fields of about 200 V/cm and above) at desired regions of interest to ablate tissue. As an example for illustrative purposes, pulsed electric field systems for the treatment of atrial fibrillation via irreversible electroporation in synchronicity with a cardiac cycle are described herein. Synchronizing ablation energy delivery with the cardiac cycle may reduce the risk of induced arrhythmias such as atrial and/or ventricular fibrillation. For example, a cardiac stimulator may be used to deliver pacing pulses to one or more cardiac chambers such that the cardiac rhythm of a patient synchronizes with the pacing pulse. However, high voltage pulse waveforms applied to tissue, for example cardiac tissue, may couple to the pacing device and induce currents in one or more of the pacing device and devices coupled thereto. This noise may lead to stimulator device malfunction, and/or device damage.

An ablation system as described herein may include a signal generator and a processor configured to apply one or more voltage pulse waveforms to a selected set of electrodes of an ablation device to deliver energy to a region of interest (e.g., ablation energy to tissue in a pulmonary vein ostium). The pulse waveforms disclosed herein may aid in therapeutic treatment of a variety of cardiac arrhythmias (e.g., atrial fibrillation). The system may further include a cardiac stimulator and pacing device used to electrically pace the heart and/or measure cardiac activity to ensure pacing capture to establish periodicity and predictability of the cardiac cycle.

The cardiac stimulator may synchronize the generation of the pulse waveform to a paced heartbeat in order to reduce unintended tissue damage. For example, a time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. In some embodiments, the ablation device may include one or more catheters, guidewires, balloons, and electrodes. The ablation device may transform into different configurations (e.g., compact and expanded) to position the device within an endocardial space. In some embodiments, the system may optionally include one or more return electrodes.

Generally, to ablate tissue, one or more catheters may be advanced in a minimally invasive manner through vasculature to a target location. In a cardiac application, the electrodes through which the ablation pulse waveform is delivered may be disposed on an epicardial device or on an endocardial device. The methods described here may include introducing an ablation device into an endocardial space of an atrium (e.g., a left atrium) of the heart and disposing the device in contact with a pulmonary vein ostium. The ablation pulse waveform may be generated in synchronization with a pacing signal of the heart to avoid disruption of the sinus rhythm of the heart. The pulse waveform may delivered to one or more electrodes of the device to ablate tissue. The pulse waveform may include hierarchical waveforms to aid in tissue ablation and reduce damage to healthy tissue.

Generally, the forward and return currents of electrical leads of the pacing device are balanced (e.g., equal in magnitude and opposite in direction) during delivery of pacing pulses. However, electrical coupling of the high voltage ablation energy to the pacing device may induce large and unbalanced currents in a frequency band in the electrical leads of the pacing device. These induced currents may disrupt the operation of the pacing device and/or cardiac stimulator coupled thereto. For example, the large voltage exposure of the pacing device may exceed the common-mode rejection of the cardiac stimulator and interrupt the pacing and/or energy delivery of the system. In some embodiments, the electrical connectors (e.g., wires, cables) coupled between components of the system may receive induced noise due to the high voltage pulse waveforms applied to tissue.

A protection device may be coupled to the pacing device to suppress induced voltage and currents in the pacing device from other electronic components (e.g., cardiac stimulator, signal generator) of the ablation system. For example, common mode and differential mode currents induced in a pacing device may be reduced and/or suppressed by a protection device (e.g., filter device). Consequently, components of the system such as the cardiac stimulator may be protected from currents that may be induced in the pacing device by the high voltage pulse waveforms applied by the ablation device. Additionally or alternatively, the protection device may further provide active circuit protection.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation may observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation may observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, a pulse waveform may include hierarchical groupings of pulses having associated timescales. In some embodiments, the methods, systems, and devices disclosed herein may comprise one or more of the methods, systems, and apparatuses described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," the contents of which are hereby incorporated by reference in its entirety.

Systems

Disclosed herein are systems and devices configured for suppressing induced currents in connection with tissue ablation via the selective and rapid application of voltage pulse waveforms resulting in irreversible electroporation. Generally, a system for ablating tissue described here may include a cardiac stimulator for generating a cardiac pacing signal delivered by a pacing device to the heart. The cardiac pacing signal is used to synchronize delivery of a pulse waveform generated by a signal generator, and the pulse waveform is delivered using an ablation device having one or more electrodes. As described herein for cardiac applications, the systems and devices may be deployed epicardially and/or endocardially. Voltages may be applied to a selected subset of the electrodes, with independent subset selections for anode and cathode electrode selections.

Overview

Figure 12:
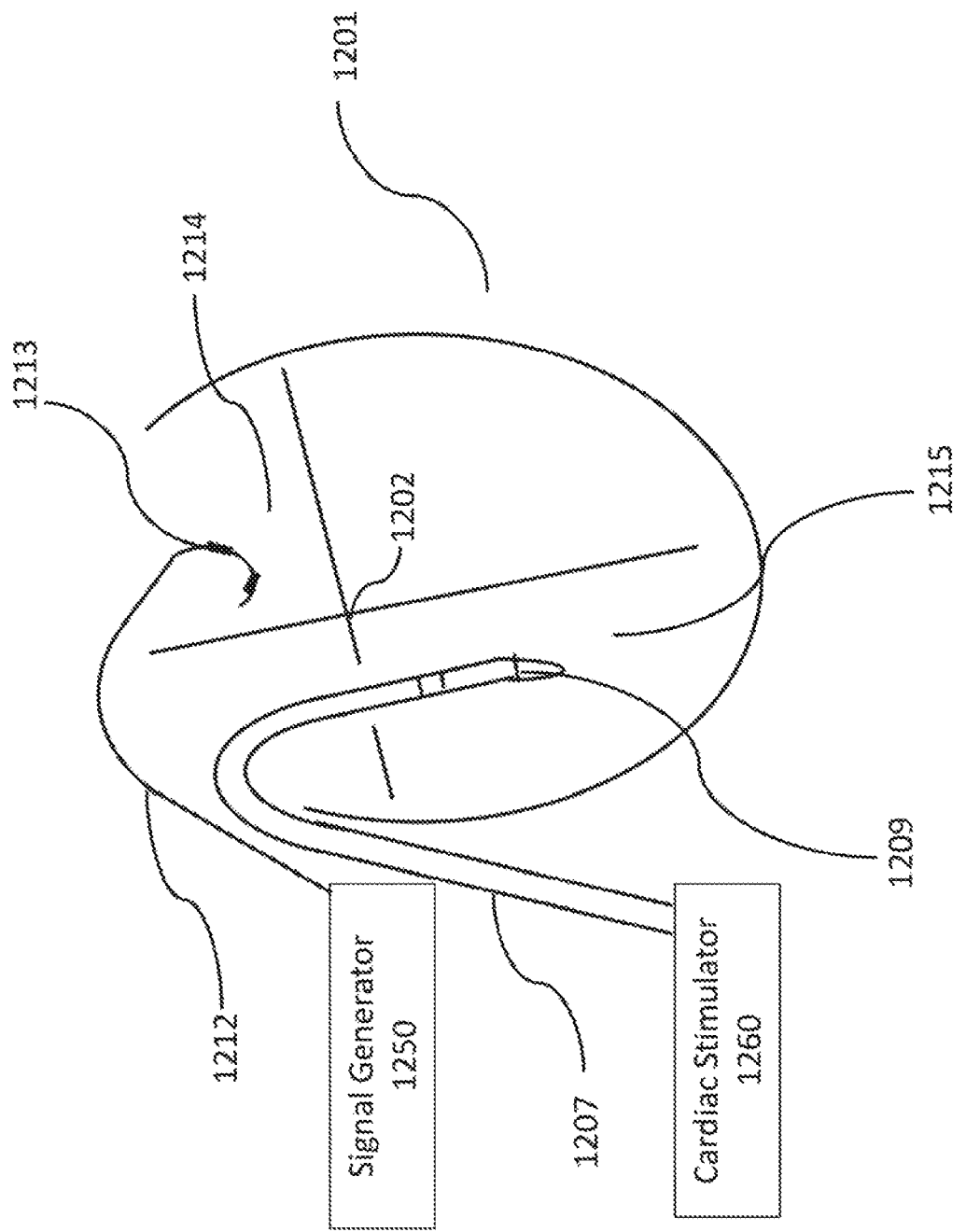
FIG. 12 is a schematic illustration of an ablation system coupled to a patient's heart, according to embodiments.

FIG. 12 is a schematic illustration of an embodiment of an electroporation system including a pacing device (1207) and an ablation device (1212) disposed in a heart (1201). The pacing device (1207) may be configured to measure cardiac activity and/or deliver a pacing signal to the heart (1201) and the ablation device (1212) may be configured to receive and/or deliver a pulse waveform to cardiac tissue. For example, FIG. 12 schematically illustrates an anterior cross-section of a heart (1201) where lines (1202) schematically approximate the boundaries of the four heart chambers including the right ventricle RV (1215) and left atrium LA (1214). Pacing device (1207) may be introduced into the right ventricle (1215) and positioned such that it can stimulate the right ventricle (1215) and obtain pacing capture. The pacing device (1207) may comprise pacing and/or signal electrodes (1209). The pacing electrodes (1209) may be configured as a bipolar pair to pace the right ventricle (1215) and may be coupled to a cardiac stimulator (1260). The signal electrodes (1209) may be configured as sensors configured to measure intracardiac activity (e.g., ECG signal) of the heart (1201). The ablation device (1212) may be configured to couple to a signal generator (1250). The signal generator (1250) may be configured to generate pulse waveforms for irreversible electroporation of tissue, such as, for example, heart tissue (1201).

In some embodiments, a distal portion of an ablation device (1212) may be introduced into an endocardial space of the left atrium (1214) through an atrial septum via a trans-septal puncture. In some embodiments, the methods, systems, and devices disclosed herein may comprise one or more of the methods, systems, and devices described in International Application Serial No. PCT/US2013/031252, filed on Mar. 14, 2013, and titled "CATHETERS, CATHETER SYSTEMS, AND METHODS FOR PUNCTURING THROUGH A TISSUE STRUCTURE AND ABLATING A TISSUE REGION," the contents of which are hereby incorporated by reference in its entirety.

The distal portion of the ablation device (1212) may include a set of electrodes (1213) configured to deliver ablation energy (e.g., pulse electric field energy) to tissue. For example, the ablation device (1212) may be positioned to align one or more electrodes (1213) to contact an inner radial surface of a lumen (e.g., one or more pulmonary vein ostia) (not shown) for delivery of pulse waveforms to ablate tissue. In some embodiments, the electrodes (1213) of the ablation device (1212) may be a set of independently addressable electrodes. Each electrode may include an insulated electrical lead configured to sustain a voltage potential of at least about 700 V without dielectric breakdown of its corresponding insulation. In some embodiments, the insulation on each of the electrical leads may sustain an electrical potential difference of between about 200 V to about 3,000 V across its thickness without dielectric breakdown. In some embodiments, the set of electrodes may include a plurality of electrodes. The plurality of electrodes may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like.

During the delivery of the pacing signal by the cardiac stimulator (1260), the forward current and the return current that flow through the electrical leads of the pacing device (1212) may be balanced; said another way, the magnitude of the forward current may be substantially equal to the magnitude of the return current, while the direction of the forward current is opposite to the direction of the return current. When the signal generator (1250) delivers the voltage pulse waveform to the heart via the ablation device (1212), due to, for example, the proximity of the ablation device (1212) and the pacing device (1207), currents may be induced in the pacing catheter leads. These may generally be unbalanced currents with high power in the kW range, and may span a range of frequencies and impact the operation of the cardiac stimulator (1260) (as well as other electronic components), in turn impacting the delivery of the voltage pulse waveform by the signal generator (1250). Thus, a need exists for methods and apparatuses for suppressing induced currents in the ablation system.

FIG. 1 illustrates an ablation system (100) configured to deliver voltage pulse waveforms for tissue ablation. The system (100) may include a signal generator (110), ablation device (140), and optionally a cardiac stimulator (150), pacing device (160), and return electrode (170). The signal generator (110) may be coupled to at least one ablation device (140), and optionally to the cardiac stimulator (150). The ablation device (140) may include a set of one or more electrodes (142). The signal or waveform generator (1250), the cardiac stimulator (1260), and the ablation catheter (1212) may be structurally and functionally similar to the signal generator (110), the cardiac stimulator (150), and the ablation device (140) described, respectively, with respect to FIG. 1.

Signal Generator

The signal generator (110) may be configured to generate pulse waveforms for irreversible electroporation of tissue, such as, for example, heart tissue. The signal generator (110) may be a voltage pulse waveform generator and deliver a pulse waveform to a set of electrodes (142a, 142b, . . . , 142n) of the ablation device (140). The signal generator (110) may generate and deliver several types of signals including, but not limited to, radiofrequency (RF), direct current (DC) impulses (such as high-voltage, ultra-short pulses used in electroporation), stimulus range impulses, and/or hybrid electrical impulses. For example, the signal generator (110) may generate monophasic (DC) pulses and biphasic (DC and AC) pulses. The signal generator (110) may include a processor (120), memory (122), a set of electrode channels (124a, 124b, . . . , 124n), energy source (126), sensing circuit (128), routing console (130), and user interface (132). One or more signal generator components may be coupled using a communication bus. The processor (120) may incorporate data received from one or more of memory (122), electrode channels (124), energy source (126), sensing circuit (128), routing console (130), user interface (132), ablation device (140), and cardiac stimulator (150) to determine the parameters (e.g., amplitude, width, duty cycle, timing, etc.) of the voltage pulse waveform to be generated by the signal generator (110). The memory (122) may further store instructions to cause the processor (120) to execute modules, processes and/or functions associated with the system (100), such as pulse waveform generation and delivery, electrode channel configuration, fault testing, energy discharge, and/or cardiac pacing synchronization. For example, the memory (122) may be configured to store anode/cathode configuration data, electrode channel configuration data, pulse waveform data, fault data, energy discharge data, heart pacing data, patient data, clinical data, procedure data, and/or the like.

In some embodiments, the ablation device (140) may include a catheter configured to receive and/or deliver the pulse waveforms described herein. For example, the ablation device (140) may be introduced into an endocardial space of the left atrium and positioned to align one or more electrodes (142a, 142b, . . . , 142n) to heart tissue (e.g., one or more pulmonary vein ostia of the left atrium), and then deliver the pulse waveforms to ablate tissue. In another example, the ablation devices (140) may ablate tissue using an epicardial approach. The ablation device (140) may include one or more electrodes (142a, 142b, . . . , 142n), which may, in some embodiments, be a set of independently addressable electrodes. For example, the electrodes (142a, 142b, . . . , 142n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrodes (142) may include any number of electrodes, for example, 2, 3, 4, 5, 6, 7, 8, 9, 10, 12, 14, 16, 18, 20, or more electrodes. In some embodiments, the methods, systems, and devices disclosed herein may comprise one or more of the methods, systems, and devices described in International Patent Application Serial No. PCT/US2017/012099, filed Jan. 4, 2017, and titled "SYSTEMS, DEVICES, AND METHODS FOR DELIVERY OF PULSED ELECTRIC FIELD ABLATIVE ENERGY TO ENDOCARDIAL TISSUE"; International Patent Application Serial No. PCT/US2018/029552, filed on Apr. 26, 2018, and titled "SYSTEMS, DEVICES, AND METHODS FOR SIGNAL GENERATION"; International Application Serial No. PCT/US2019/014226, filed on Jan. 18, 2019, and titled "SYSTEMS, DEVICES, AND METHODS FOR FOCAL ABLATION"; and International Application Serial No. PCT/US2013/031252, filed on Mar. 14, 2013, and titled "CATHETERS, CATHETER SYSTEMS, AND METHODS FOR PUNCTURING THROUGH A TISSUE STRUCTURE AND ABLATING A TISSUE REGION," the contents of each of which are hereby incorporated by reference in their entirety.

In some embodiments, the processor (120) may be any suitable processing device configured to run and/or execute a set of instructions or code and may include one or more data processors, image processors, graphics processing units, physics processing units, digital signal processors, and/or central processing units. The processor (120) may be, for example, a general purpose processor, Field Programmable Gate Array (FPGA), an Application Specific Integrated Circuit (ASIC), and/or the like. The processor (120) may be configured to run and/or execute application processes and/or other modules, processes and/or functions associated with the system and/or a network associated therewith (not shown). In some embodiments, the processor may comprise both a microcontroller unit and an FPGA unit, with the microcontroller sending electrode sequence instructions to the FPGA. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some embodiments, the memory (122) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (122) may store instructions to cause the processor (120) to execute modules, processes and/or functions associated with the system (100), such as pulse waveform generation, electrode channel configuration, fault detection, energy discharge, and/or cardiac pacing.

In some embodiments, a set of electrode channels (124) may include a set of active solid-state switches. The set of electrode channels (124) may be configured in a number of ways, including independent anode/cathode configuration for each electrode channel. For example, the electrode channels (124a, 124b, . . . , 124n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrode channels (124) may include any number of channels, for example, 2, 3, 4, 5, 6, 7, 8, 9, 10, 12, 14, 16, 18, 20, or more electrode channels. Energy delivery may use any combination of electrode channels (124) and any order for an energy delivery sequence. The energy delivered may be an RF and/or any tissue ablation energy.

The set of electrode channels (124) may be coupled to a routing console (130) to deliver energy to a set of electrodes (142) coupled to the routing console (130). The set of electrode channels (124) may be coupled to an energy source (126) to receive energy (e.g., a pulse waveform). Processor (120) may be coupled to each electrode channel (124) to configure an anode/cathode configuration for each electrode channel (124), which may be configured on a per pulse basis, per operator input, and/or the like. The processor (120) and energy source (126) may be collectively configured to deliver a pulse waveform to the set of electrodes (142) through the set of electrode channels (124). In some embodiments, each electrode channel (124) may include an electronic switch (e.g., bipolar transistor) and a drive circuit, as described in detail herein. In some embodiments, each electrode channel (124) may have a bootstrap configuration for low and high frequency operation. For example, the pulse duration of voltage pulses delivered through an electrode channel may be in the range of between about 1 microsecond and about 1000 microseconds. In biphasic mode, this corresponds to an approximate frequency range of between about 500 Hz and about 500 KHz for the frequency associated with the voltage pulses.

In some embodiments, an energy source (126) may be configured to convert and supply energy to a set of electrodes (142) coupled to the signal generator (110). The energy source (126) of the signal generator (110) may include a DC power supply and be configured as an AC/DC switcher. In some embodiments, an energy source (126) of the signal generator (110) may deliver rectangular-wave pulses with a peak maximum voltage of about 7 kV into a device with an impedance in the range of about 30Ω to about 3000Ω for a maximum duration of about 1000 μs. In some of these embodiments, the energy source (126) may be configured to store energy. For example, the energy source (126) may include one or more capacitors to store energy from a power supply. While these examples are included for purely non-limiting illustrative purposes, it is noted that a variety of pulse waveforms with a range of pulse durations, intervals between pulses, pulse groupings, etc. may be generated depending on the clinical application.

In some embodiments, a sensing circuit (128) may be configured to determine an amount of current being delivered to a device coupled to the signal generator (110) (e.g., electrode (142) coupled to the electrode channel (124)). As described in more detail herein, the sensing circuit (128) may also be used to classify an electrode channel fault, monitor capacitor discharge, and/or sense arcing. In some embodiments, the sensing circuit (128) may be a direct current sensing circuit and/or a low-side sensing circuit. The sensing circuit may include one or more operational amplifiers, difference amplifiers (DA), instrumentation amplifiers (IA), and/or current shunt monitors (CSM).

In some embodiments, the routing console (130) may be configured to electrically couple a set of electrodes (142) of an ablation device (140) to a set of electrode channels (124). The routing console (130) may be configured to selectively deliver energy to the set of electrodes (142) using the set of electrode channels (124). One or more ablation devices (140) each having a set of electrodes (142) may be coupled to the routing console (130). The set of electrodes (142) may include any number of electrodes, for example, 1, 2, 3, 4, 5, 6, 7, 8, 9, 10, 12, 14, 16, 18, 20, or more electrodes.

In some embodiments, the electrode channels (124) configured for energy delivery (e.g., configured as an anode/cathode pair of electrode channels) may not be adjacent to each other. For example, the set of electrode channels (124) may include a set of N electrode channels (124n) in a linear array. In one embodiment, a first electrode channel may correspond to a first electrode channel (124a) in the linear array of N electrode channels (124n). One or more of a second and third electrode channel (124b, 124c) may not be adjacent to the first electrode channel (124a) in the linear array of N electrode channels (124n).

Figure 5:
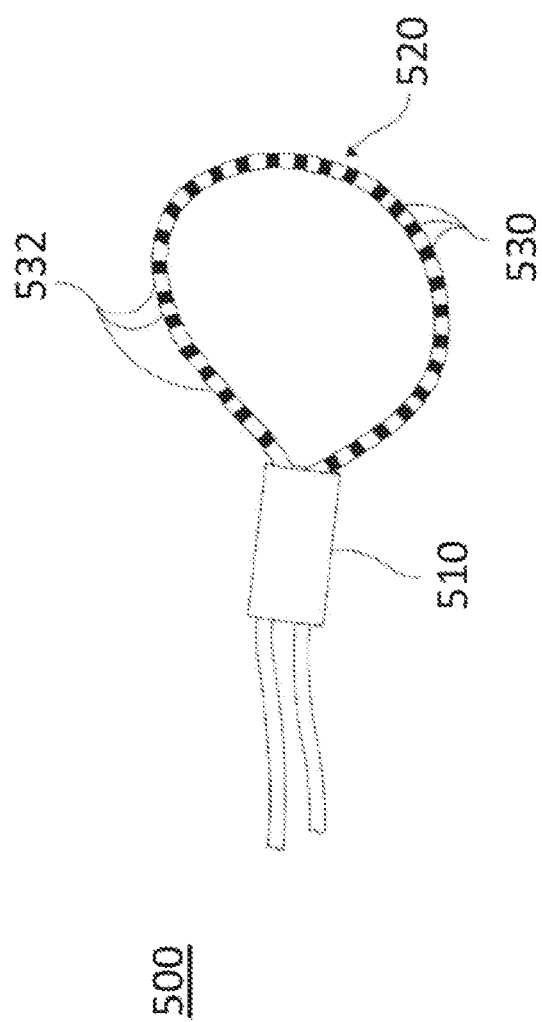
FIG. 5 is a partial close-up view of a central portion of an ablation catheter, according to embodiments.

A multi-electrode ablation device may allow targeted and precise energy delivery to tissue. In some embodiments, the electrodes (142) of an ablation device (140) may be configured for energy delivery (e.g., as an anode/cathode pair of electrodes (142)) and may be adjacent to each other within a linear array of the electrodes (142) in the ablation device (140). For example, an ablation device (140) may include a set of electrodes (142) as a linear array of N electrodes (142n). As discussed in more detail herein, FIG. 5 illustrates another embodiment of an ablation device (500) including a linear array of electrodes (530). The signal generator (110) coupled to the ablation device (140) may include a set of electrode channels (124) having N electrode channels (124n) corresponding to the N electrodes (142n) of the ablation device (140). In one embodiment, the first electrode channel (124a) of the N electrode channels (124n) may correspond to a first electrode (142a) in the linear array of N electrodes (142n). One or more of second and third electrode channel (124b, 124c) of the N electrode channels (124n) may not correspond to any of the electrodes adjacent to the first electrode (142a) in the linear array of N electrodes (142n).

Configurable electrode channel and electrode selection may provide flexibility in positioning the electrodes for ablating a desired region of interest. In one embodiment, the routing console (130) may couple to a set of 16 electrodes (142) of an ablation device (140). The routing console (130) may receive input from the processor (120) and/or user interface (132) for electrode channel selection and energy delivery to one or more electrodes (142). Additionally or alternatively, the routing console (130) may couple to a cardiac stimulator (150) and be configured to receive data from devices (e.g., heart pacing data from a pacing device) used for synchronization of a pulse waveform with a patient cardiac cycle. In embodiments, the waveform or signal generator may integrate and/or include pacing and/or cardiac stimulator functionality.

In some embodiments, a user interface (132) may be configured as a communication interface between an operator and the system (100). The user interface (132) may include an input device and output device (e.g., touch surface and display). For example, patient data from memory (122) may be received by user interface (132) and output visually and/or audibly. Electric current data from sensing circuit (128) may be received and output on a display of user interface (132). As another example, operator control of an input device having one or more buttons, knobs, dials, switches, trackball, touch surface, and/or the like, may generate a control signal to the signal generator (110) and/or ablation device (140).

In some embodiments, an input device of the user interface (132) may include a touch surface for operator input and may be configured to detect contact and movement on the touch surface using any of a plurality of touch sensitivity technologies including capacitive, resistive, infrared, optical imaging, dispersive signal, acoustic pulse recognition, and surface acoustic wave technologies. Additionally or alternatively, the user interface (132) may include a step switch or foot pedal.

In some embodiments, an output device of the user interface (132) may include one or more of a display device and audio device. The display device may include at least one of a light emitting diode (LED), liquid crystal display (LCD), electroluminescent display (ELD), plasma display panel (PDP), thin film transistor (TFT), and organic light emitting diodes (OLED). An audio device may audibly output patient data, sensor data, system data, other data, alarms, warnings, and/or the like. The audio device may include at least one of a speaker, piezoelectric audio device, magnetostrictive speaker, and/or digital speaker. In one embodiment, the audio device may output an audible warning upon detection of a fault in the signal generator (110).

In some embodiments, the signal generator (110) may be mounted on a trolley or cart. In some embodiments, the user interface (132) may be formed in the same or different housing as the signal generator (110). The user interface (132) may be mounted to any suitable object, such as furniture (e.g., a bed rail), a wall, a ceiling, or may be self-standing. In some embodiments, the input device may include a wired and/or wireless transmitter configured to transmit a control signal to a wired and/or wireless receiver of the signal generator (110).

In some embodiments, a cardiac stimulator (150) including a pacing device (160) may be configured to generate a heart pacing signal to be delivered to a patient via the pacing device (160) to pace one or more chambers of the heart for cardiac stimulation. The pacing device (160) may be configured to pace the heart and measure cardiac activity. The pacing device (160) may include pacing electrodes and signal electrodes. In some embodiments, the pacing device (160) may deliver a pacing pulse generated by a cardiac stimulator (150) using the pacing electrodes. The pacing device (160) may further measure cardiac activity corresponding to intracardiac activity (e.g., ECG signal) using the signal electrodes. An indication of the pacing signal may be transmitted by the cardiac stimulator (150) to the signal generator (110). Based on the pacing signal, an indication of a voltage pulse waveform may be selected, computed, and/or otherwise identified by the processor (120) and generated by the signal generator (110). In some embodiments, the signal generator (110) may further include circuitry for the generation of cardiac stimulation and/or pacing signals and thereby provide stimulator functionality. In some embodiments, the signal generator (110) may be configured to generate the voltage pulse waveform in synchronization with the indication of the pacing signal (e.g., within a common refractory window). For example, in some embodiments, the common refractory window may start substantially immediately following a ventricular pacing signal (or after a very small delay) and last for a duration of approximately 250 milliseconds (ms) or less (e.g., between about 150 ms and about 250 ms) thereafter. In such embodiments, an entire pulse waveform may be delivered within this duration. Heart pacing is described further herein with respect to FIG. 11.

The return electrode (170) may be coupled to a patient (e.g., disposed on a patient's back) to allow current to pass from the pacing device (160) through the patient and then to the return electrode (170) to provide a safe current return path from the patient (not shown). In some embodiments, the systems described herein may include one or more sterile coverings configured to create a sterile barrier around portions of the system (100). In some embodiments, the system (100) may include one or more sterile coverings to form a sterile field. For example, a sterile covering may be placed between the ablation device(s) and the patient, forming a barrier between an interior, non-sterile side including the patient, signal generator, and ablation devices and an exterior, sterile side including the operator. Additionally or alternatively, components of the system (100) may be sterilizable. The sterile covering may include, for example, a sterile drape configured to cover at least a portion of a system component. In one embodiment, a sterile covering (e.g., sterile drape) may be configured to create a sterile barrier with respect to a user interface (132) of the system (100). The sterile drape may be clear and allow an operator to visualize and manually manipulate the user interface (132). The sterile covering may conform tightly around one or more system components or may drape loosely so as to allow components to be adjusted within the sterile field.

Figure 2:
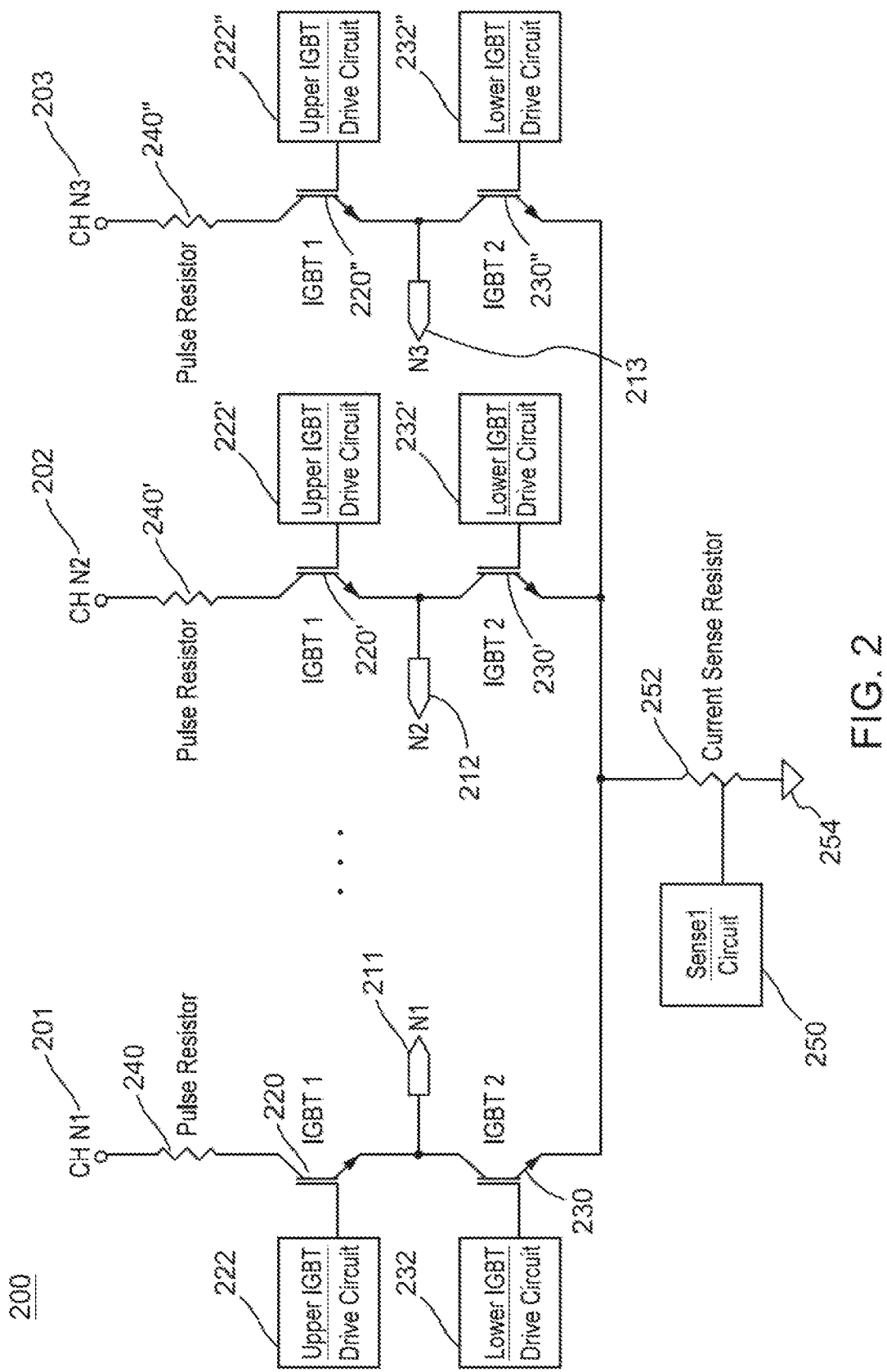
FIG. 2 is a circuit diagram of a signal generator, according to embodiments.

FIG. 2 illustrates a circuit diagram of an embodiment of a signal generator (200) that may be structurally and/or functionally similar to signal generator (110). The signal generator (200) may include one or more electrode channels (201, 202, 203). FIG. 2 illustrates each of the electrode channels having a similar circuit configuration that may be structurally and/or functionally similar to the electrode channels (124a, 124b, . . . , 124n). In some embodiments, each of the electrodes channels (201, 202, 203) may be configured individually as a half bridge amplifier while a pair of the electrode channels may be collectively configured as a full bridge amplifier. The signal generators as described herein may include a flexibly programmable electrode configuration; various subsets of electrodes may be configured as anodes and cathodes dynamically and rapidly. Thus, in an ablation energy delivery process, energy may be delivered rapidly over a sequence of paired electrode subsets. In some cases, a given electrode may be configured as an anode, and shortly thereafter as a cathode, during the course of sequencing over a succession of paired electrode subsets. Likewise, a biphasic waveform may also be delivered with the help of this topology, where an initially given anode-cathode pair may be made to reverse polarity after a very brief switching time interval; repeatedly alternating the sequencing of anode/cathode selection may yield a biphasic voltage pulse train. The signal generator (200) may include N number of electrode channels, for example, 1, 2, 3, 4, 5, 6, 7, 8, 9, 10, 12, 14, 16, 18, 20, or more electrode channels. Described with reference to the first electrode channel (201) for the sake of simplicity, each electrode channel may include a first electronic switch (220) configured to switch between an ON state and an OFF state. A first drive circuit (222) may be coupled to the gate terminal of the first electronic switch (220) to control the state of the first electronic switch (220). The first electrode channel (201) further includes a second electronic switch (230) configured to switch between an ON and an OFF state. A second drive circuit (232) may be coupled to the gate terminal of the second electronic switch (230) to control the state of the second electronic switch (230). Each of the drive circuits (222, 232) may be coupled to and controlled by a processor (e.g., processor (120)). An output channel (211) may be coupled to the emitter terminal of the first electronic switch (220) and to the collector terminal of the second electronic switch (230), and may form part of a current path for electrical currents to pass via electrodes on a medical device (not shown) through an electrical load (such as patient anatomy) to one or more output channels coupled to a second electrode channel as described below. The output channel (211) may be coupled to a first electrode such as a first electrode 142(a) of ablation device (140).

Likewise, second and third electrode channels (202, 203) may include respective first electronic switches (220', 220"), each configured to switch between an ON state and an OFF state. First drive circuits (222', 222") may be coupled to respective first electronic switches (220', 220") to control the state of the first electronic switches (220', 220"). Output channels (212, 213) may be coupled between the emitter terminals of the first electronic switches (220', 220") and the collector terminals of the second electronic switches (230', 230"). The output channels (212, 213) may be coupled to respective second and third electrodes, such as the second electrode (142b) and the third electrode (142c) of ablation device (140). The second and third electrode channels (202, 203) further include respective second electronic switches (230', 230") configured to switch between an ON and an OFF state. Second drive circuits (232', 232") may be coupled to the gate terminals of the second electronic switches (230', 230") to control the state of the second electronic switches (230', 230"). Each of the drive circuits (222', 222", 232', 232") may be coupled to and controlled by a processor (e.g., processor (120)). The drive circuits controlled by the processor effectively comprise the routing console 130. As described above, the routing console may be configured to couple to a set of device electrodes connected to the output channels. Each electrode channel (201, 202, . . . ) corresponds to a respective electrode (142a, 142b, . . . ) of the set of device electrodes. As an exemplary illustration of waveform delivery, if switches (220, 230) are respectively in ON and OFF states, switches (220', 230') are respectively in OFF and ON states, and switches (220" and 230") are respectively in OFF and ON states, and all other switches of all other electrode channels are in an OFF state, a positive voltage pulse is delivered with output channel N (211) as anode or positive terminal and with output channels N+3 (212 in FIG. 2) and N+4 (213 in FIG. 2) as cathodes or negative/ground terminals. The duration of the ON state of the switches determines the time width of the pulse. In this manner a sequence of pulses may be delivered over any sequence of anode-cathode pairings, including repeated pulsing of a given or particular anode-cathode combination. Waveform delivery may be interspersed over a sequence of electrodes with the architecture of the generator disclosed herein. While the example of electrode channel selection disclosed in the foregoing described the selection of one anode channel and two cathode channels, it should be clear that a variety of such anode-cathode combinations may be selected without limitation.

The electronic switches (220-220", 230-230", 320-320", 330-330") as described herein may include one or more bipolar transistors, such as bipolar junction transistors or Bipolar Field Effect Transistors. In some embodiments, one or more of the electronic switches include insulated-gate bipolar transistors (IGBT's). Such IGBT switches may be capable of handling the high instantaneous power associated with high voltages, in the approximate range of about 50,000 W to about 300,000 W. An energy source (not shown) may be coupled to the collector terminals of the first electronic switches (220, 220', 220") of the electrode channels (201, 202, 203) through respective resistive elements (240, 240', 240"). As described herein in more detail, the resistive elements (240, 240', 240") may each be configured to discharge a capacitive element of the energy source when the energy source is not in use. In some embodiments, the resistive element may have a resistance in the range of between about 5 Ohms and about 25 Ohms. Each of the electrode channels (201, 202, 203) may be coupled to a sensing circuit (250) and current sense resistor (252). In some embodiments, the sensing circuit (250) may be configured to detect arcing during use. In FIG. 2, the sensing circuit (250) may be coupled between the emitter terminal of the second electronic switches (230, 230', 230") and ground (254). Additionally or alternatively, each electrode channel (201, 202, 203) may be coupled to a respective sensing circuit (250) and current sense resistor (252).

In some embodiments, as described with respect to FIGS. 1 and 2, a processor such as processor (120) coupled to the set of drive circuits (222, 232) may configure the first electrode channel (201) as an anode. One or more of the second and third electrode channels (202, 203) may similarly be configured by the processor (120) as a cathode. In one embodiment, the first electrode channel (201) may be configured as an anode by setting the first electronic switch (220) of the first electrode channel (201) to the ON state and by setting the second electronic switch (230) of the first electrode channel (201) to the OFF state. Each of the second and third electrode channels (202, 203) may be configured as a cathode by setting their respective first electronic switches (220', 220") to the OFF state and setting their respective second electronic switches (230', 230") to the ON state. In this manner, the electrode channels (201, 202) may, for example, form a current path to a tissue site (e.g., coupled to each of the output channels (211, 212) using the first electronic switch (220) of the first electrode channel (201) and second electronic switch (230') of the second electrode channel (202).

The processor (120) and energy source (126) may be collectively configured to deliver a pulse waveform to the set of electrodes during use via one or more of the electrode channels (201, 202, 203). The signal generator (200) may deliver biphasic (AC) pulses where in some embodiments, after delivering a voltage pulse to the set of output channels (211, 212, 213) with output channels (211) as an anode and output channels (212, 213) as cathodes, the polarities are immediately reversed and a voltage pulse of opposite polarity is then delivered with output channel (211) as a cathode and output channels (212, 213) as anodes, and so on until a desired number of biphasic pulses has been delivered to the output channel set (211, 212, 213) in the form of a suitable waveform. Subsequently (and possibly with a programmable time interval), a different set of device electrodes (or output channels) may be configured as anodes and cathodes, and the waveform may be delivered again over this new set of device electrodes. In this manner, the voltage waveform may be sequenced over any desired collection of electrodes. Generally, the processor (120) and energy source (126) may be collectively configured to deliver the pulse waveform over a sequenced set of electrodes (142a, 142b, . . . , 142n).

In some embodiments, as described in more detail herein, the pulse waveform delivered using the signal generator (200) may include a set of levels of a hierarchy and/or may be in synchronization with the indication of a pacing signal generated from a cardiac stimulator (150).

Figure 3:
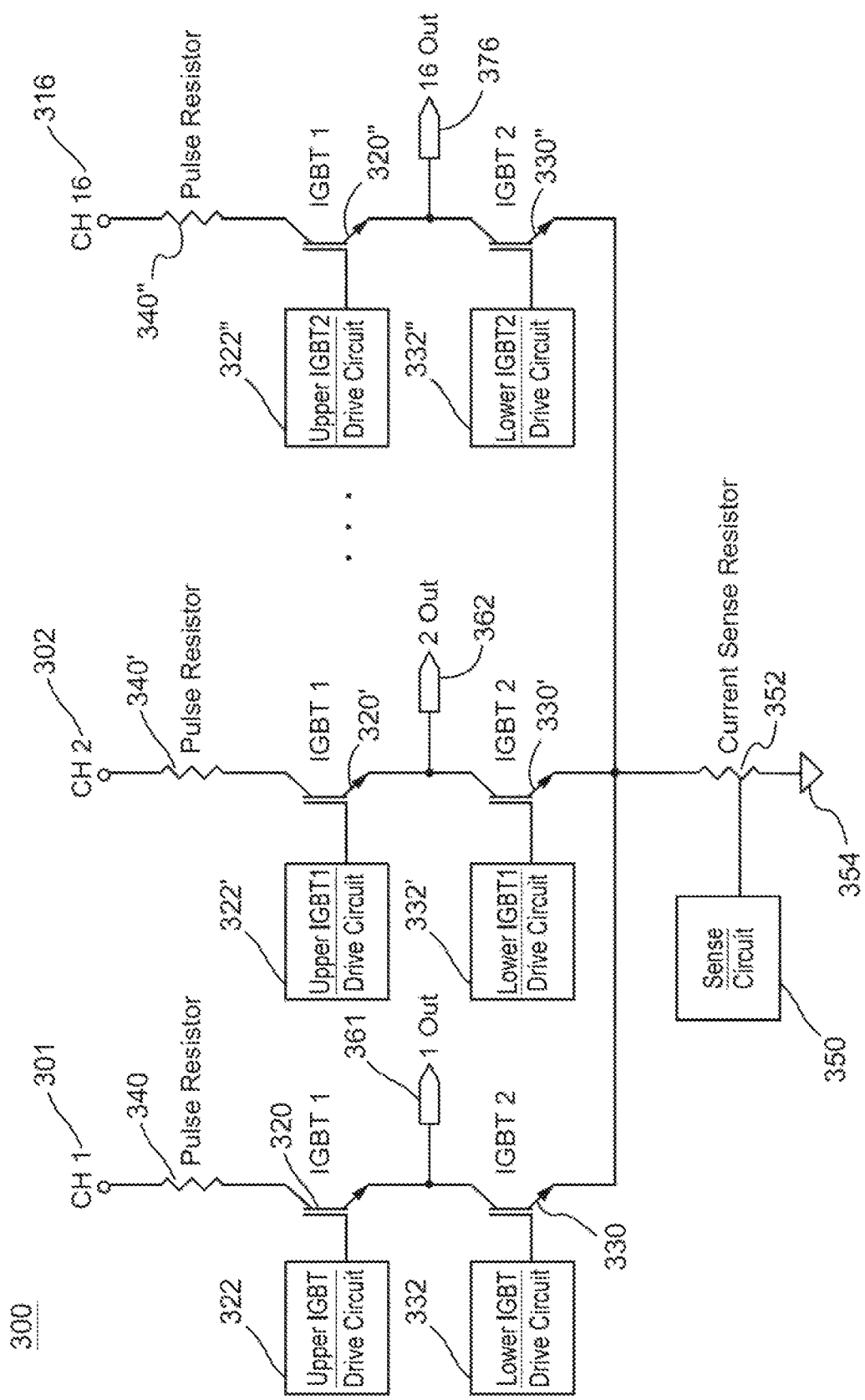
FIG. 3 is a circuit diagram of a signal generator, according to embodiments.

FIG. 3 illustrates a circuit diagram of an embodiment of a signal generator (300) that may be structurally and/or functionally similar to signal generator (110). For example, the signal generator (300) may include one or more electrode channels (301, 302, 316) that may be structurally and/or functionally similar to the electrode channels (124a, 124b, . . . , 124n). For ease of explanation, unless explicitly noted otherwise, elements in FIG. 3 may have the same components, functionality, and/or values as discussed with respect to similar elements in FIG. 2. For example, the electrode channels (201, 202, 203) used to deliver pulse waveforms to a set of electrodes in FIG. 2 may be the same set of electrode channels (301, 302, 316) used for capacitive energy discharge in FIG. 3. The signal generator (300) may include one or more electrode channels (301, 302, . . . , 316) where FIG. 3 illustrates each of the electrode channels having a same circuit configuration. FIG. 3 illustrates 16 electrode channels, although it should be appreciated that the signal generator (300) may include N number of electrode channels, for example, 1, 2, 3, 4, 5, 6, 7, 8, 9, 10, 12, 14, 16, 18, 20, or more electrode channels. A first electrode channel (301) may include a first electronic switch (320) configured to switch between an ON state and an OFF state. A first drive circuit (322) may be coupled to the gate terminal of the first electronic switch (320) to control the state of the first electronic switch (320). The first electrode channel (301) may further include a second electronic switch (330) configured to switch between an ON and an OFF state. A second drive circuit (332) may be coupled to the gate terminal of the second electronic switch (330) to control the state of the second electronic switch (330). An output channel (361) may be coupled between the emitter terminal of the first electronic switch (320) and the collector terminal of the second electronic switch (330).

Likewise, a second and sixteenth electrode channel (302, 316) may include respective first electronic switches (320', 320") configured to switch between an ON state and an OFF state. The first drive circuits (322', 322") may be coupled to respective first electronic switches (320', 320") to control the state of the first electronic switches (320',320"). Output channels (362, 376) may be coupled between the emitter terminal of the first electronic switches (320', 320") and the collector terminal of the second electronic switches (330', 330"). The second and sixteenth electrode channels (302, 316) further include respective second electronic switches (330', 330") configured to switch between an ON and an OFF state. A second drive circuit (332', 332") may be coupled to the gate terminal of the second electronic switch (330', 330") to control the state of the second electronic switch (330', 330"). Each of the output channels (361, 362, 376) may be coupled to respective electrodes on one or more medical devices (not shown). Each electrode channel (301, 302, 316) may thus correspond to a respective electrode of the set of electrodes on one or more medical devices.

The electronic switches as described herein may include one or more bipolar transistors. In some embodiments, one or more of the electronic switches include insulated-gate bipolar transistors. An energy source (not shown) may be coupled to the collector terminals of the first electronic switches (320, 320', 320") of the electrode channel (301, 302, 316) through respective resistive elements (340, 340', 340"). The resistive elements (340, 340', 340") may each be configured to discharge a capacitive element of the energy source when the energy source is not in use. Each of the electrode channels (301, 302, 316) may be coupled to a sensing circuit (350) and current sense resistor (352). In some embodiments, the sensing circuit (350) may be configured to detect arcing during use. In FIG. 3, the sensing circuit (350) may be coupled between the emitter terminal of the second electronic switches (330, 330', 330") and ground (354). Additionally or alternatively, each electrode channel (301, 302, 316) may be coupled to a respective sensing circuit (350) and current sense resistor (352).

In some embodiments, as described with respect to FIGS. 1 and 3, the signal generator (110) may provide active monitoring of the electrode channels. For example, the processor (120) of the signal generator (110) may be configured to perform one or more fault tests to verify operation of one or more electrode channels (124a, 124b, . . . , 124n) (e.g., electronic switches and drive circuits), the energy source (126) (e.g., DC power supply), and sensing circuit (128) (e.g., arc detection). The fault tests may be performed on one or more electrode channels (124a, 124b, . . . , 124n) at predetermined intervals (e.g., upon startup before delivery of a pulse waveform, between delivery of pulse waveforms, when the energy source (126) is not in use). In some embodiments, the signal generator (300) may perform a series of fault tests on one or more electrode channels to classify a working state of one or more electrode channels. In one embodiment, after delivery of a pulse waveform to a set of electrodes (142a, 142b, . . . , 142n) at a first time, a first fault test may be conducted individually for one or more of the set of electrode channels (301, 302, . . . , 316). In some embodiments, the first fault test may include, for the first electrode channel (301), setting the first electronic switch (320) to the ON state and the second electronic switch (330) to the OFF state. A verification DC voltage may be applied to the first electrode channel (301) for fault testing. In one embodiment, the verification DC voltage may be about 50V. The first electrode channel (301) may be classified as passing the first fault test when substantially no current is detected by the sensing circuit (350) during the first fault test. The first electrode channel (301) may be classified as failing the first fault test (e.g., in fault) when a threshold current, for example a current of 10 mA or higher, is detected by the sensing circuit (350). In some embodiments, the second fault test may include, for the first electrode channel (301), setting the first electronic switch (320) to the OFF state and the second electronic switch (330) to the ON state. The first electrode channel (301) may be classified as passing the second fault test when substantially no current is detected by the sensing circuit (350) during the second fault test. The first electrode channel (301) may be classified as failing the second fault test when a threshold current, for example a current of 10 mA or higher, is detected by the sensing circuit (350). In some embodiments, the third fault test may include, for the first electrode channel (301), setting the first electronic switch (320) to the ON state and the second electronic switch (330) to the ON state. The first electrode channel (301) may be classified as passing the third fault test when a predetermined amount of current is detected by the sensing circuit (350) during the third fault test and classified as failing the third fault test when the sensing circuit (350) detects a non-predetermined amount of current. For example, the predetermined amount of current (e.g., about 5 A) may be equal to a DC voltage output by the energy source (e.g., about 50 V) divided by a resistance of the resistive element (340) (e.g., about 10Ω).

A failure in the first fault test may indicate a malfunction in the second electronic switch (330) and/or second drive circuit drive (332) (e.g., lower IGBT circuitry in FIG. 3) while a failure in the second fault test may indicate a malfunction in the first electronic switch (320) and/or first drive circuit (322) (e.g., upper IGBT circuitry in FIG. 3). A failure in the third fault test may indicate a malfunction in one or more of the energy source, sensing circuit, electronic switches, and drive logic. Accordingly, the fault tests may verify the individual and collective operation of upper and lower IGBT circuitry for a fault tested electrode channel. Each of the fault tests described herein may be performed for each electrode channel (301, 302, . . . , 316) at a predetermined interval.

In some embodiments, a fault test may be performed for an electrode channel (124) based on predetermined criteria (e.g., a predetermined number of pulses delivered, a predetermined amount of energy delivered, and/or the like). Each electrode channel or a subset of electrode channels may be verified. For example, fault tests may be performed on each electrode channel (124) configured as an anode, or for each electrode channel (124) after delivery of 5 pulses. In some embodiments, the fault tests may be conducted in conjunction with voltage pulse waveform delivery and capacitor discharge, as described in more detail herein.

The generation and delivery of high voltage pulse waveforms using a signal generator as described herein may lead to an energy source (e.g., one or more capacitors) of the signal generator storing excess energy. This energy may be discharged to ground through a set of discharge pulses using the electrode channels. Discharge may be performed prior to delivering subsequent pulse waveforms. In other words, the electrode channels may be used to deliver tissue ablation energy to one or more electrodes as well as separately and internally discharge excess energy to ground. This configuration may be used in place of a dump circuit and/or bleeder resistor circuit for discharging excess stored energy in the signal generator.

In some embodiments, as described with respect to FIGS. 1 and 3, each electrode channel (124) may sequentially partially discharge the energy source (126) to ground over a set of cycles. Each electrode channel (124) may be configured as a half bridge amplifier to partially discharge the energy source to ground. The energy source (126) may complete discharge of a predetermined amount of energy within seconds. As used herein, a discharge cycle refers to energy discharge of the energy source to ground using each of the electrode channels of the set of electrode channels. For example, energy may be partially discharged to ground one at a time through each electrode channel (124) of a signal generator (110). In some embodiments, fault detection may be performed on the electrode channels (124) at predetermined intervals (e.g., before each discharge cycle, after a predetermined number of discharge cycles, etc.) to ensure that energy discharge is performed as intended. As stored energy is reduced through discharging, a pulse width of a discharge pulse may be increased without causing damage to the electrode channels (124). For example, an initial, first amount of stored energy (e.g., about 3 kJ) of the energy source (126) may correspond to discharge pulses having a first predetermined pulse width (e.g., about 0.5 µs). After discharge of the energy source to a second amount of stored energy, the pulse width of the discharge pulses may be configured to a second predetermined pulse width (e.g., about 2 µs).

In some embodiments, the set of electrode channels illustrated in FIG. 3 may correspond to a set of discharge paths to ground to reduce an amount of stored energy of an energy source (126). In some embodiments, the first electrode channel (301) of the set of electrode channels (301, 302, ..., 316) may be configured to partially discharge energy to ground after a delivering a pulse waveform to a set of electrodes (142). For example, the first electronic switch (320) may be set to the ON state and the second electronic switch (330) may be set to the ON state for a predetermined duration of time to at least partially discharge the energy source (126). This current through the first electrode channel (301) may be about equivalent to the DC voltage of the energy source (126) divided by a resistance of the resistive element (340). The first electrode channel (301) may discharge energy to ground using a predetermined pulse width (e.g., about 0.5 µs).

Once the first electrode channel (301) partially discharges the energy source (126), each of the remaining electrode channels (302, ..., 316) may be configured to partially discharge the energy source (126) one at a time in a manner analogous to the first electrode channel (301). In some embodiments, a channel inactive time period (e.g., dead time) may follow the partial energy discharge of an electrode channel. For example, a channel inactive time period following each electrode channel energy discharge may be about 100 µs. In some embodiments, a discharge cycle inactive time period may follow each discharge cycle. For example, a discharge cycle inactive time period may be about 5 ms and may correspond to a bootstrap charge time. By staggering the discharge of each electrode channel, the signal generator (300) may discharge capacitor energy at a faster rate than conventional circuit topologies.

The set of electrode channels (124) may discharge the energy source to ground sequentially over a set of discharge cycles until reaching a predetermined energy threshold. In some embodiments, energy discharge may be performed such that a pulse width increases over time or over each discharge cycle. The number of pulses may decrease as the pulse width increases. In some embodiments, energy discharge may be configured as follows: a first pulse width may be between about 0.1 µs and about 1 µs and may be set between about 90 discharge cycles and about 130 discharge cycles; a second pulse width may be between about 1 µs and about 5 µs and may be set between about 80 discharge cycles and about 90 discharge cycles; a third pulse width may be between about 5 µs and about 10 µs and may be set between about 70 discharge cycles and about 80 discharge cycles; a fourth pulse width may be between about 10 µs and about 15 µs and may be set for about 70 discharge cycles or less; and a fifth pulse width may be between about 15 µs and about 25 µs and may be set for about 70 discharge cycles or less.

In one merely illustrative and non-limiting example, a set of 16 electrode channels may be used to discharge to ground an energy source of about 3 kJ at an average rate of about 1 kJ/sec such that the signal generator may complete discharge in about 3 seconds. In one embodiment, energy discharge may be configured as follows: a first pulse width of about 0.5 µs may be set for about 110 discharge cycles over about 730 ms; a second pulse width of about 2 µs may be set for about 80 discharge cycles over about 530 ms; a third pulse width of about 6 µs may be set for about 73 discharge cycles over about 490 ms; a fourth pulse width of about 12.5 µs may be set for about 70 discharge cycles over about 480 ms; and a fifth pulse width of about 25 µs may be set over about 780 ms for any remaining discharge cycles left to complete the energy source discharge.

In some embodiments, fault detection as described herein may be performed on an electrode channel prior to a partial energy discharge using that electrode channel. If the electrode channel is determined to be in a fault state, the electrode channel may be excluded from the set of electrode channels used to discharge the energy source to ground and/or the fault status may be output to the operator. Verification of the electrode channels may be performed for each of the electrode channels or a subset of the electrode channels at predetermined intervals such as for: each energy discharge pulse; one or more discharge cycles (e.g., fault test the electrode channels after each cycle or every other cycle); pulse width transitions (e.g., fault detect the electrode channels between every increase in pulse width); and a predetermined time interval (e.g., fault test the electrode channels every 0.1 seconds, 0.25 seconds, 0.5 seconds, 1 second, etc.).

Ablation Device

Figure 4A:
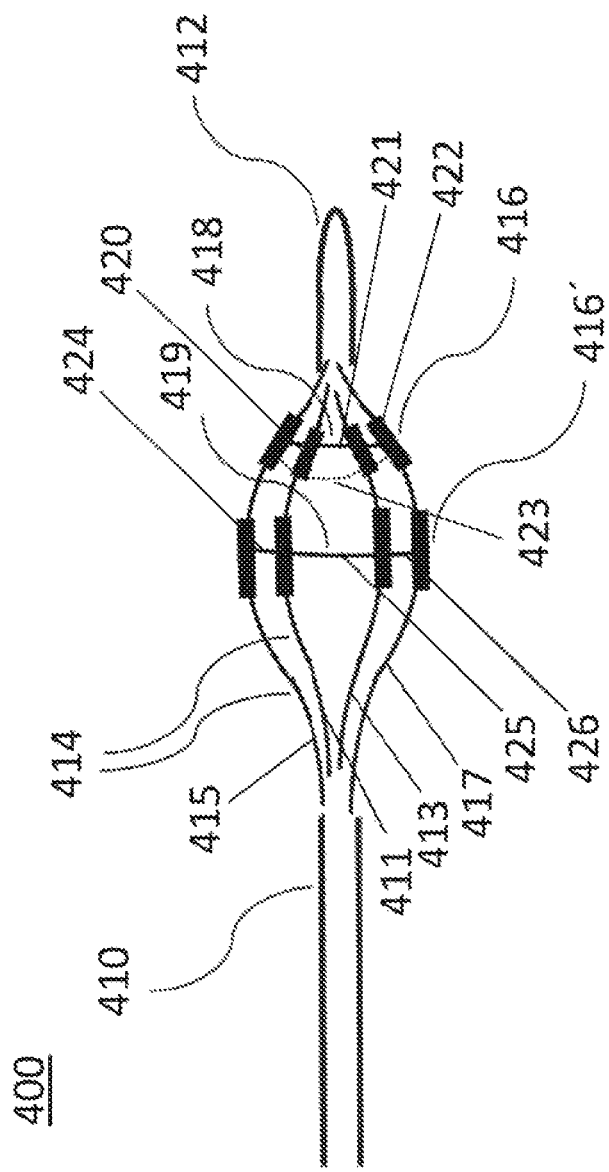
FIG. 4A is a side view of an ablation catheter, according to embodiments.

The systems described here may include one or more multi-electrode ablation devices configured to ablate heart tissue for treating atrial fibrillation such as in a left atrial chamber of a heart. FIG. 4A illustrates an embodiment of an ablation device (e.g., structurally and/or functionally similar to the ablation device (140)) that may be configured to deliver voltage pulse waveforms using a set of electrodes to ablate tissue and electrically isolate a pulmonary vein. In some of these embodiments, the ablation device may be transformed from a first configuration to a second configuration such that the electrodes of the ablation device expand outward to contact a lumen or an ostium or an antrum of an orifice in tissue (e.g., pulmonary vein ostium or pulmonary vein antrum). The ablation devices as described herein are for exemplary or illustrative purposes only and a variety of other ablation devices may be implemented without departing from the scope of the present invention.

The ablation device (400) includes a catheter shaft (410) at a proximal end of the device (400), a distal cap (412) of the device (400), and a set of splines (414) coupled thereto. The distal cap (412) may include an atraumatic shape. A proximal end of the set of splines (414) may be coupled to a distal end of the catheter shaft (410), and a distal end of the set of splines (414) may be tethered to the distal cap (412)

of the device (400). Each spline (414) of the ablation device (400) may include one or more electrodes (416) formed on a surface of the spline (414). Each electrode (416) may include an insulated electrical lead configured to sustain a voltage potential of at least about 700 V without dielectric breakdown of its corresponding insulation. In other embodiments, the insulation on each of the electrical leads may sustain an electrical potential difference of between about 200V to about 1500 V across its thickness without dielectric breakdown. Each spline (414) may include the insulated electrical leads of each electrode (416) formed in a body of the spline (414) (e.g., within a lumen of the spline (414)). A set of spline wires (418, 419) may be electrically conductive and electrically couple adjacent electrodes (416) disposed on different splines (414). For example, the spline wire (418) (connecting electrodes (416)) and the spline wire (419) (connecting electrodes (416')) may extend in a transverse direction relative to a longitudinal axis of the ablation device (400).

FIG. 4A illustrates a set of splines (414) where each spline (414) includes a pair of electrodes (416 and 416') having about the same size, shape, and spacing as the electrodes (416 and 416') of an adjacent spline (414). In other embodiments, the size, shape, and spacing of the electrodes (416, 416') may differ. For example, the electrodes (416) electrically coupled to a first spline wire (418) may differ in size and/or shape from electrodes (416') electrically coupled to a second spline wire (419).

In some embodiments, the first spline wire (418) may include a first set of spline wires (420, 421, 422, 423), where each spline wire of the set of spline wires (420, 421, 422, 423) may couple electrodes (416) between a different pair of splines of the set of splines (414). In some of these embodiments, the set of spline wires (420, 421, 422, 423) may form a continuous loop between the electrodes (416) coupled thereto. Likewise, the second spline wire (419) may include a second set of spline wires (424, 425, 426), where each spline wire of the set of spline wires (424, 425, 426) may couple electrodes (416') across the set of splines (414). The second set of spline wires (424, 425, 426) may couple different electrodes (416') across the set of splines (414) than the first set of spline wires (420, 421, 422, 423). In some of these embodiments, the first set of spline wires (420, 421, 422, 423) may form a first continuous loop between the electrodes (416) coupled thereto and the second set of spline wires (424, 425, 426) may form a second continuous loop between the electrodes (416') coupled thereto. The first continuous loop may be electrically isolated from the second continuous loop. In some of these embodiments, the electrodes (416) coupled to the first continuous loop may be configured as anodes and the electrodes (416') coupled to the second continuous loop may be configured as cathodes. A pulse waveform generated by a signal generator may be delivered to the electrodes (416 and 416') of the first and second continuous loop. In some embodiments, the spline wires such as 421, 422, 423, etc. may be replaced by similar electrical connections in the proximal part of the device (for example, in the device handle). For example, the electrodes (416) may all be electrically wired together in the handle of the device.

Figure 4B:
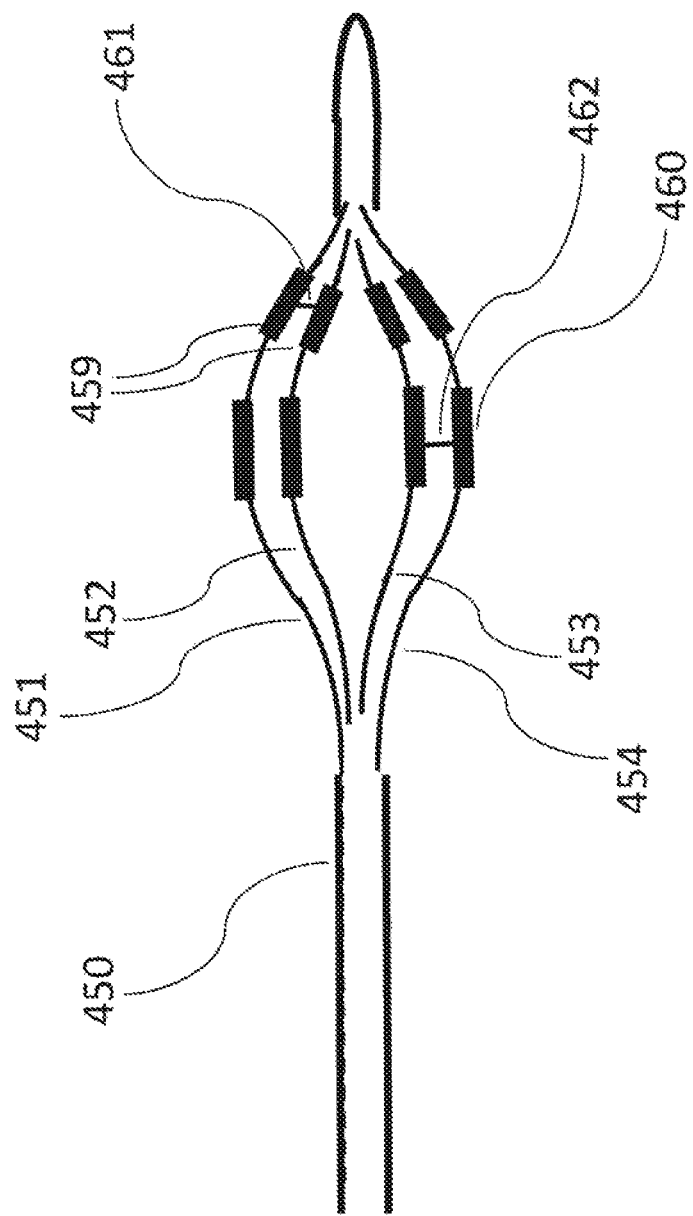
FIG. 4B is a side view of an ablation catheter, according to embodiments.

In another embodiment illustrated in FIG. 4B, the first spline wire (461) of the set of spline wires (461, 462) may couple electrodes (459) between a first spline (451) and a second spline (452) of the set of splines, and a second spline wire (462) of the set of spline wires (461, 462) may couple electrodes (460) between the third spline (453) and a fourth spline (454) of the set of splines. The electrodes (459) coupled by the first spline wire (461) and the electrodes (460) coupled by the second spline wire (462) may be configured as an anode and cathode respectively (or vice-versa). A pulse waveform may be delivered to the electrodes (459) coupled by the first spline wire (461) and the electrodes (460) coupled by the second spline wire (462). In some embodiments, instead of spline wires the electrical leads of at least two electrodes of the set of electrodes may be electrically coupled at or near a proximal portion of the ablation device, such as, for example, within a handle.

In other embodiments, referring to FIG. 4A, one or more of the spline wires (418, 419) may form a continuous loop between the electrically coupled electrodes (416). For example, a first set of spline wires (418) may form a first continuous loop between the electrodes (416) coupled thereto and a second set of spline wires (419) may form a second continuous loop between the electrodes (416') coupled thereto. In this case, the first continuous loop may be electrically isolated from the second continuous loop. In one embodiment, each of the electrodes (416) coupled to a first set of spline wires (418) may be configured as an anode while each of the electrodes (416) coupled to a second set of spline wires (419) may be configured as a cathode. Each group of electrically coupled electrodes (416) may be independently addressable. In some embodiments, instead of spline wires the electrical leads of at least two electrodes of the set of electrodes may be electrically coupled at or near a proximal portion of the ablation device, such as, for example, within a handle.

In other embodiments, the size, shape, and spacing of the electrodes (416) may differ. The ablation device (400) may include any number of splines, for example, 3, 4, 5, 6, 7, 8, 9, 10, 12, 14, 16, 18, 20, or more splines. In some embodiments, the ablation device (400) may include 3 to 20 splines. For example, in one embodiment, the ablation device (400) may include between 4 and 9 splines.

For each of the ablation devices described herein, each of the splines may include a polymer and define a lumen so as to form a hollow tube. The one or more electrodes of the ablation device described herein may include a diameter from about 0.2 mm to about 2.5 mm and a length from about 0.2 mm to about 5.0 mm. In some embodiments, the electrode may include a diameter of about 1 mm and a length of about 1 mm. As the electrodes may be independently addressable, the electrodes may be energized in any sequence using any pulse waveform sufficient to ablate tissue by irreversible electroporation. For example, different sets of electrodes may deliver different sets of pulses (e.g., hierarchical pulse waveforms). It should be appreciated that the size, shape, and spacing of the electrodes on and between the splines may be configured to deliver energy sufficient to generate contiguous/transmural lesions in order to electrically isolate one or more pulmonary veins. In some embodiments, alternate electrodes (e.g., all the distal electrodes) may be at the same electric potential, and likewise for all the other electrodes (e.g., all the proximal electrodes). Thus, ablation may be delivered rapidly with all electrodes activated at the same time. A variety of such electrode pairing options exist and may be implemented based on the convenience thereof.

For each of the ablation devices discussed herein, the electrodes (e.g., ablation electrode, return electrode) may include biocompatible metals such as titanium, palladium, silver, platinum or a platinum alloy. For example, the electrode may preferably include platinum or a platinum alloy. Each electrode may include an electrical lead having sufficient electrical insulation to sustain an electrical potential difference of at least 700V across its thickness without dielectric breakdown. In other embodiments, the insulation on each of the electrical leads may sustain an electrical potential difference of between about 200 V to about 3,000 V across its thickness without dielectric breakdown, including all values and sub-ranges in between. The insulated electrical leads may run to the proximal handle portion of the catheter from where they may be connected to a suitable electrical connector. The catheter shaft may be made of a flexible polymeric material such as Teflon, Nylon, Pebax, etc.

FIG. 5 illustrates an embodiment of an ablation device (500) (e.g., structurally and/or functionally similar to the ablation device (140)) that may be configured to deliver voltage pulse waveforms generated by a signal generator (110) as described herein using a set of electrodes to ablate tissue which in some embodiments may generate a linear circumferential ablation lesion. The ablation device (500) may include a catheter (510) having a flexible elongate shaft (520). The elongate shaft (520) may be advanced and withdrawn from a lumen of the catheter (510). The flexibility of the catheter (510) may facilitate positioning of the electrodes (530) around asymmetric and/or complex contours. The elongate shaft (520) may include a set of electrodes (530) spaced apart along the elongate shaft (520). In some embodiments, the electrodes (530) may be integrally formed with the elongate shaft (520). Each of the electrodes (530) may be connected to a respective output channel of a signal generator. The electrodes (530) may be independently configured as an anode or cathode and configured to deliver a pulse waveform to target tissue to perform ablation. In some embodiments, the set of electrodes (530) may have a spacing (532) between electrodes configured to create a contiguous ablation lesion such as a circumscribing lesion around a left atrial target and pulmonary vein. In some embodiments, the ratio of the spacing (532) between consecutive electrodes (530) to the longitudinal length of each electrode may be less than about 3:1, and may be less than about 2:1.

Protection Device

Generally, the systems and devices configured for suppressing induced currents in connection with tissue ablation may include a protection device coupled between a first electronic device (e.g., pacing device) and a second electronic device (e.g., an apparatus to be protected). As described in more detail herein, the protection device configured to suppress a voltage and current induced in the first electronic device. The induced current may include one or more of a common mode current and a differential mode current. In some embodiments, the protection device may include one or more transformers and capacitors configured to suppress the induced current, and one or more diodes configured to shunt the induced voltage. In some embodiments, the protection device may include one or more inductors configured to suppress an alternating current induced in the first electronic device in a predetermined frequency range. In some embodiments, the protection device may include one or more balun circuits configured to suppress a common mode current induced in the first electronic device over a set of predetermined frequency ranges. In some embodiments, the protection device may be formed separate from the apparatus and the pacing device. In some embodiments, one or more protection devices may be formed integral with one or more of the apparatus and pacing device.

Figure 13:
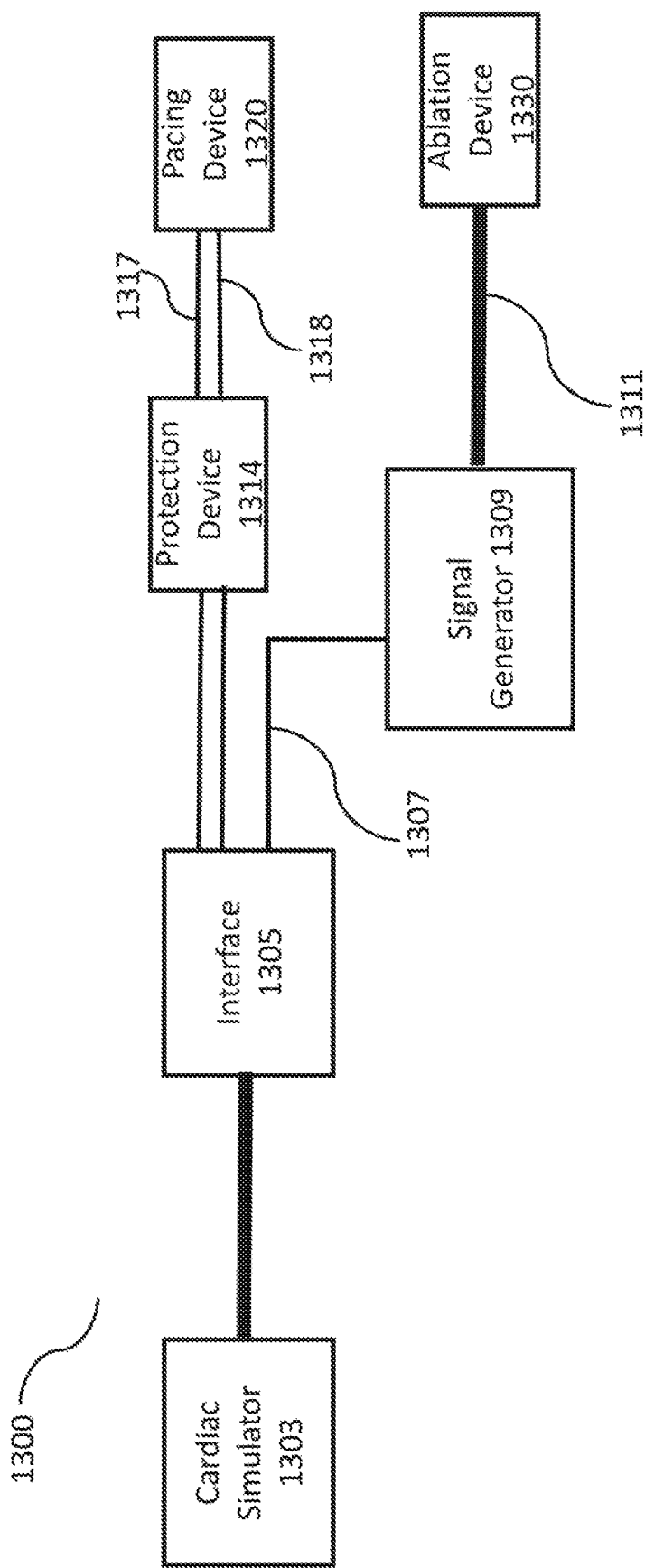
FIG. 13 is a block diagram illustrating an ablation system including a protection device, according to some embodiments.

FIG. 13 is a block diagram illustrating an ablation system (1300) including a protection device (1314) (e.g., filter box), according to some embodiments. In some embodiments, the ablation system (1300) may include a signal generator (1309), a cardiac stimulator (1303), an interface device (1305), a protection device (1314), electrical leads (1317, 1318) of pacing electrodes in a pacing device (1320), and the electrical ablation lead (1311) coupled to an ablation device (e.g., ablation catheter) (1330). The signal generator (1309) and the cardiac stimulator (1303) may be structurally and functionally similar to the signal generator (1250) and the cardiac stimulator (1260) described, respectively, with respect to FIG. 12. The cardiac stimulator (1303) may be configured to generate a pacing signal and deliver it to pacing device (1320) via the interface device (1305), the protection device (1314), and the electrical leads (1317, 1318). The pacing signal may be further delivered to the signal generator (1309) via the interface device (1305). The interface device (1305) may be configured to allow a connection between two or more of the cardiac stimulator (1303), one or more pacing devices (1320), signal generator (1309), and ablation device(s) (1330). For example, connectors such as a wired connector (e.g., cable of several meters in length) may be used and allow convenient and adaptable placement of system components within a space such as a clinical procedure room. In some embodiments, the signal generator (1309) may be configured to generate the voltage pulse waveform in synchronization with the indication of the pacing signal (e.g., within a common refractory window). The signal generator (1309) may deliver the voltage pulse waveform to the ablation device (1330) via the ablation lead (1311) (e.g., cable) to ablate tissue.

As the signal generator (1309) delivers the voltage pulse waveform to an ablation device (1330), the cardiac simulator (1303) may deliver the pacing signal to the pacing device (1320). However, a current may be induced in the pacing device leads (1317, 1318) by the proximity of the pacing device (132) to the voltage pulse waveform applied to tissue. These unbalanced currents may span a range of frequencies and impact the operation of one or more components of the system such as the cardiac stimulator (1303) and the signal generator (1309). Induced voltages and currents from the pacing device (1320) may interfere with operation of the cardiac stimulator (1303) such that the signal generator (1309) does not receive proper pacing signals from the cardiac stimulator (1303). Accordingly, operation of the signal generator (1309) may be interrupted, resulting in error and interruption of ablation energy delivery. The protection devices, as described in more detail herein, may be configured to suppress the propagation of induced currents and voltages in the system.

Figure 14:
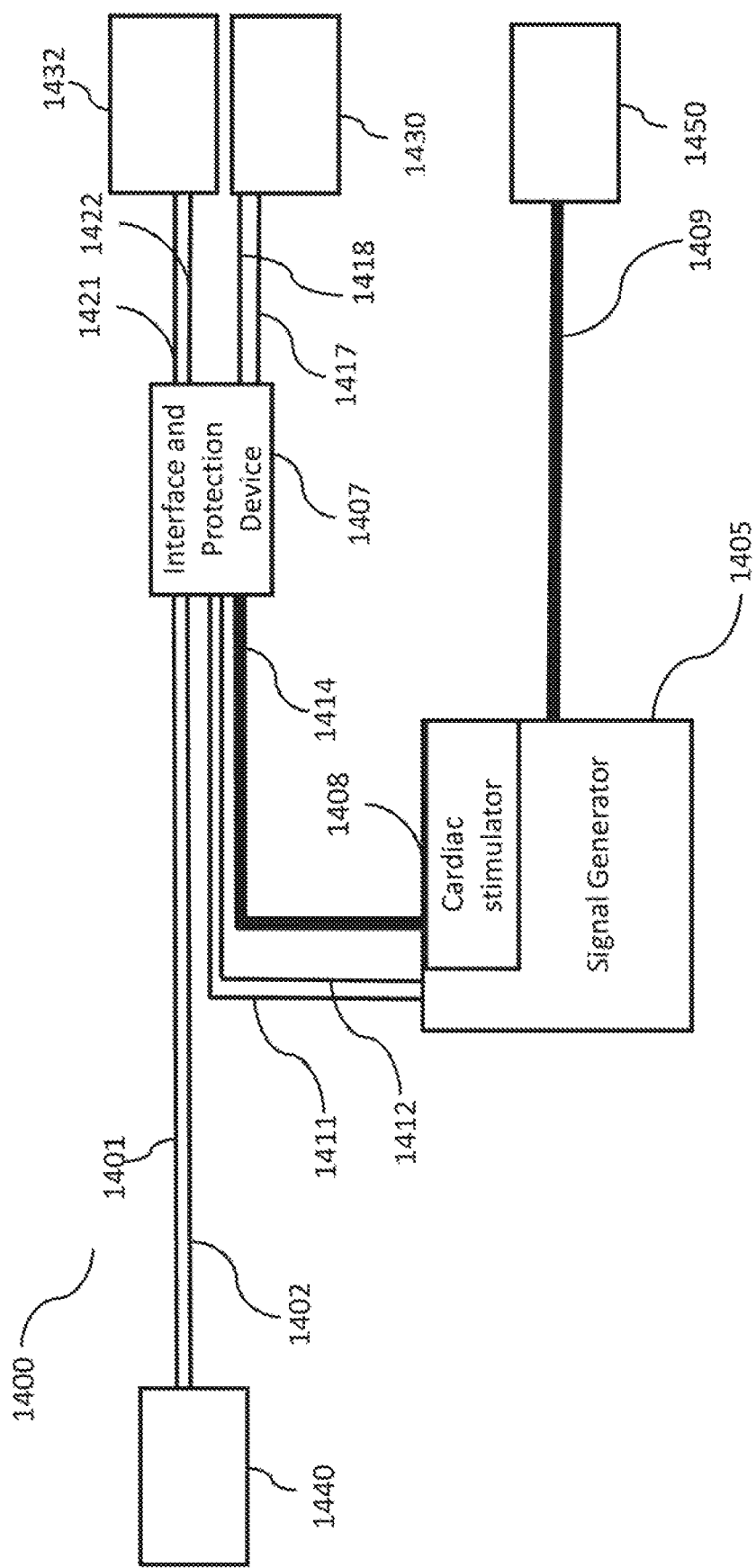
FIG. 14 is a block diagram illustrating an ablation system including a protection device, according to other embodiments.

FIG. 14 is a block diagram illustrating an ablation system (1400) including an interface device integrated with the protection device (1407) in the same enclosure (e.g., housing) and a cardiac simulator (1408) integrated with the signal generator (1405) in the same enclosure. A pacing signal may be generated by the integrated signal generator (1405) and cardiac simulator (1408) and delivered to a pacing device (1430) via the pacing device leads (1417, 1418). The combined interface device and the protection device (1407) may be configured to suppress (or reduce) the induced currents in the pacing device leads (1417, 1418).

In some embodiments, one or more electrode channels (1421, 1422) on an intracardiac device (1432) may be used as sensing channels for ECG analysis. The incoming ECG signals received from the patient via electrode channels (1421, 1422) may be filtered through the combined interface and protection device (1407) before they are delivered via leads (1411, 1412) to the signal generator (1405) for ECG analysis. In some embodiments, the ECG signals may also be delivered through leads (1401, 1402) to an ECG recording system (1440) and/or other external device (e.g., sensing and/or mapping systems). The signal generator (1405) may deliver the voltage pulse waveform to an ablation device (1450) via the cable (1409) to ablate tissue.

In some embodiments, one or more of an interface device (e.g., interface (1305)), a protection device (e.g., protection device (1314)), or an interface and protection device (e.g., interface and protection device (1407)) can be integrated into a cardiac stimulator and/or signal generator (e.g., cardiac stimulator (1303), signal generator (1309), or cardiac stimulator (1408) and signal generator (1405)). For example, in an alternative arrangement, a protection device can be integrated into a signal generator, which in turn is connected to and/or integrated with a cardiac stimulator, such that induced currents from the pacing device leads can be suppressed (e.g., filtered) by the protection device before it reaches the cardiac stimulator.

Figure 15:
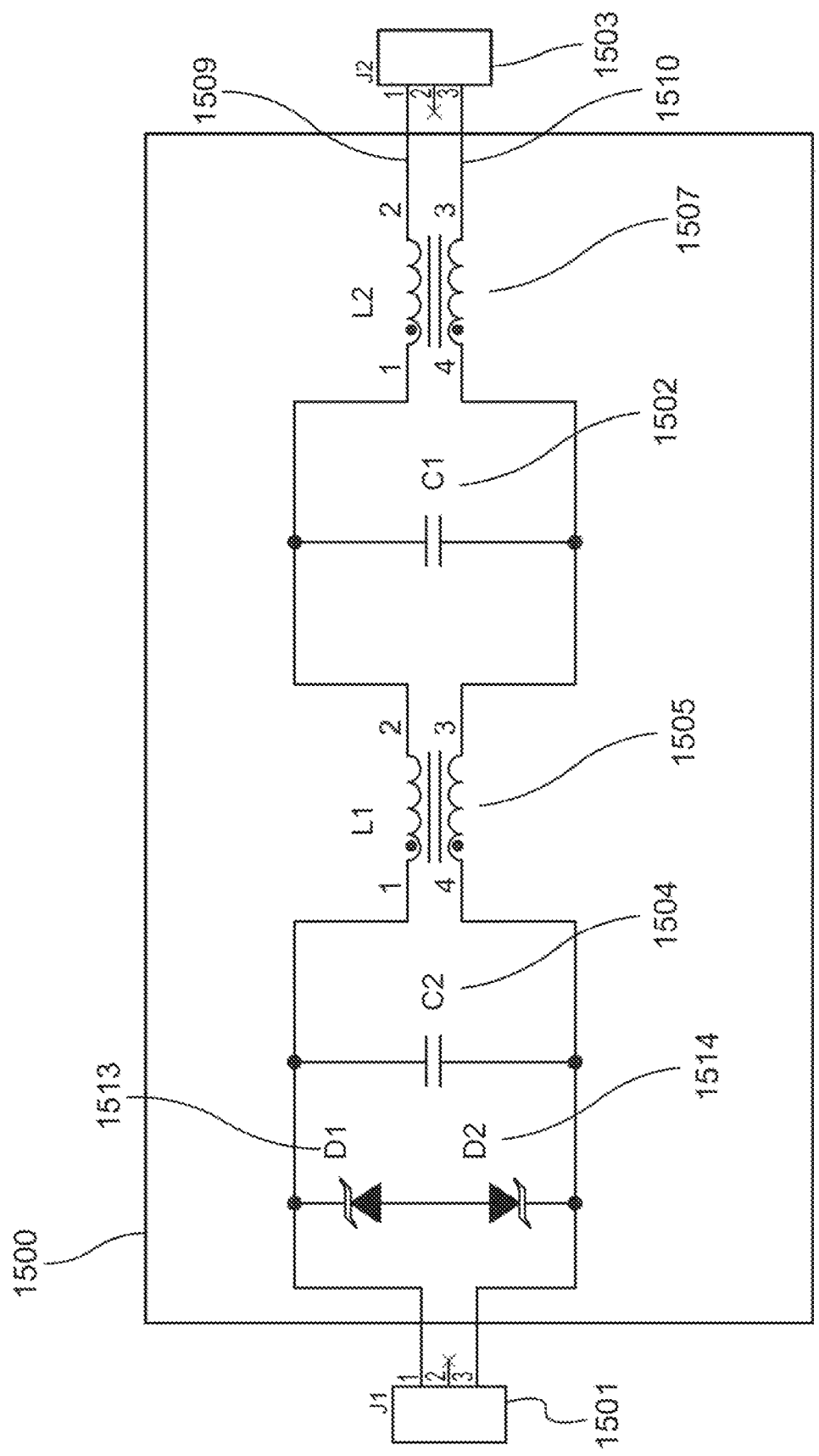
FIG. 15 is a circuit diagram of a protection device in a non-tuned common mode, according to embodiments.

FIG. 15 is a circuit diagram of a protection circuit (1500) configured to suppress common mode currents with transformers as described in the following, according to embodiments. The protection circuit (1500) may be configured to suppress large voltages and common mode currents that are induced in the pacing device leads (1509, 1510) by the pulse waveform generated by the signal generator (not shown in FIG. 15). In addition to suppressing common mode currents, the protection circuit may be configured in a common-differential mode (as described with respect to FIG. 18) and a tunable mode (as described with respect to FIGS. 20A-24). The protection circuit (1500) may include a first common mode transformer L2 (1507), a second common mode transformer L1 (1505), a first capacitor C1 (1502), a second capacitor C2 (1504), and first and second Zener diodes (1513, 1514). In some embodiments, the first diode D1 (1513) and second diode D2 (1514) may be configured to shunt an induced voltage away from the second electronic device (e.g., cardiac stimulator (1501)). The second capacitor C2 (1504) may short relatively high frequencies across the pacing device leads (1509, 1510) and suppress induced currents from flowing in the pacing device leads (1509, 1510). The first common mode transformer (1507) and the second common mode transformer (1505) may be configured to suppress common mode currents in the pacing device leads (1509, 1510), as a high-impedance element for common mode currents. The first capacitor C1 (1502) may short above a predetermined frequency (higher than the lower end of the band-stop range) across the pacing device leads (1509, 1510) and suppress induced currents from flowing in the pacing device leads (1509, 1510).

The signal generator may be structurally and/or functionally similar to the signal generator (1309) described with respect to FIG. 13 or the signal generator (1405) described with respect to FIG. 14. The protection circuit (1500) may be configured to be coupled to the cardiac simulator (1501) and the pacing device leads (1509, 1510). The pacing device leads (1509, 1510) may be included within a pacing device that may be introduced into a cardiac chamber of a patient (1503). The cardiac stimulator (1501) may be configured to generate a heart pacing signal to be delivered to the patient (1503).

Figure 16:
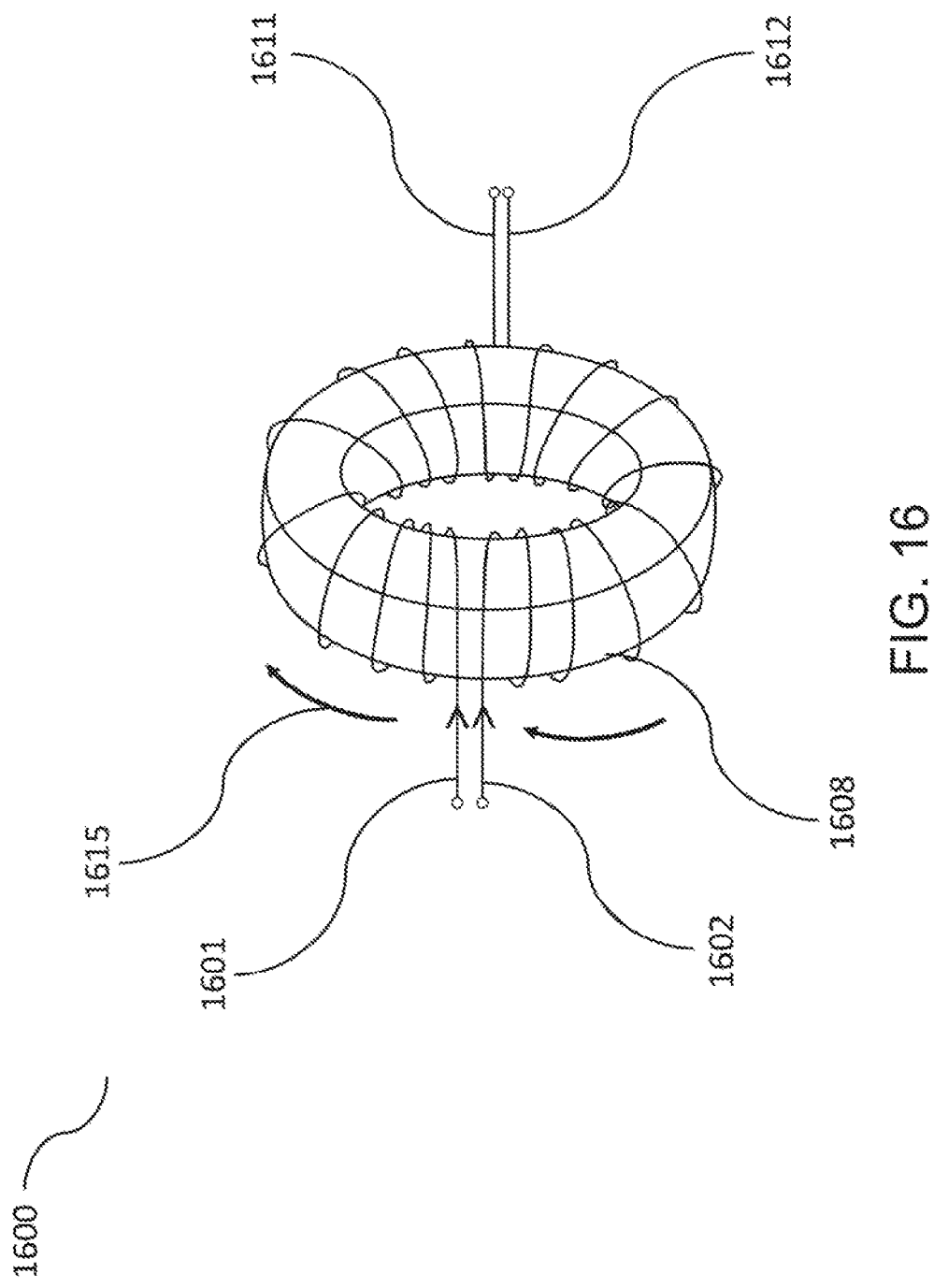
FIG. 16 is a perspective view of a common mode transformer, according to embodiments.

FIG. 16 illustrates an embodiment of the first common mode transformer L2 (1507) and the second common mode transformer L1 (1505). As shown in FIG. 16, a common mode transformer (1600) may include a toroid core (1608), a first winding (1601, 1611), and a second winding (1602, 1612). The toroid core (1608) may include or be a soft magnetic material that has a high magnetic permeability (e.g., iron) in a ring shape. The toroid core (1608) may be chosen to have a construction with relatively broad laminations (for example, a set of laminations where each lamination's cross section has an aspect ratio of 5 or less) to allow losses in the core (1608). The first winding (1601 to 1611) and the second winding (1602 to 1612) wind around a body of the core (1608) in the same direction, while the first winding (1601 to 1611) winds along the circumferential axis of the core (1608) in a first direction (e.g., a counterclockwise direction as shown in FIG. 16)) and the second winding (1602 to 1612) winds along the circumferential axis of the core (1608) in a second direction opposite to the first direction (e.g., a clockwise direction as shown in FIG. 16).

In some embodiments, the outer radius of the core (1608) may be between about 4 cm and about 10 cm, and the inner radius of the core (1608) may be between about 2 cm and about 9 cm, including all values and sub-ranges in-between. In some embodiments, the thickness of the core (1608) may be between about 1 cm and about 6 cm. In some instances, the number of turns (e.g., windings) on each winding (1601, 1602) may be between about 3 and about 50, including all values and sub-ranges in-between.

In some embodiments, common mode currents with a non-zero frequency may flow through the first winding (from 1601 to 1611) and the second winding (from 1602 to 1612) in parallel directions in the leads 1601 and 1602 at the ends of the toroid such that a first magnetic field generated by the current through the first winding (1601 to 1611) and a second magnetic field generated by the current through the second winding (1602 to 1612) may have equal magnitude in same direction (1615). In other words, the common mode transformer (1600) may generate a magnetic field in a single circumferential direction (i.e., either parallel or anti-parallel to the arrow 1615) when a common mode current flows through the first and second windings. The equal magnitude and in-phase magnetic fields may add together, resulting in a high impedance to the common mode current, which passes through the common mode transformer (1600) heavily attenuated. For example, the common mode power suppression may be at least about 15 dB over a frequency band between about 100 kHz and about 10 MHz, including all values and sub-ranges in-between. In some embodiments, the suppression can be 20 dB, 25 dB or larger. The impedance to the common mode current may further include a real component (e.g., due to resistive core losses) in addition to an imaginary component (e.g., due to a high inductance of the core winding). The actual attenuation (e.g., common mode rejection) depends on the relative magnitudes of the transformer impedance and the load impedance. Thus, the common mode transformer (1600) may be configured to have an inductance of at least about 1 milliHenry and an effective resistance of at least about 500 Ohms. In other words, this impedance may act to suppress, reduce, or minimize the magnitude of the common mode current.

Returning to FIG. 15, the first common mode transformer (1507) and the second common mode transformer (1505) may be configured to suppress common mode currents in the leads, as a high-impedance element for common mode currents. As shown in FIG. 15, the first common mode transformer (1507) may be positioned between the pacing device leads (1509, 1510) of the first electronic device (1503) (e.g., pacing device) and the first capacitor C1 (1502). The first capacitor C1 (1502) may be used as a low-impedance capacitor for frequencies greater than the lower end (e.g., 0.5 MHz or higher) of the desired band-stop range. Thus, the first capacitor C1 (1502) may short relatively high frequencies (higher than the lower end of the band-stop range) across the pacing device leads (1509, 1510) and suppress induced currents from flowing in the pacing device leads (1509, 1510).

As shown in FIG. 15, the second common mode transformer (1505) may be positioned between the first capacitor C1 (1502) and the second capacitor C2 (1504). Similar to the second common mode transformer (1507), the first common mode transformer (1505) may be configured to generate a high impedance, and thus, suppressing, reducing or minimizing the magnitude of the common mode current. Similar to the first capacitor C1 (1502), the second capacitor C2 (1504) may short relatively high frequencies (e.g., voltages having frequencies above a predetermined threshold) across the pacing device leads (1509, 1510) and suppress induced currents from flowing in the pacing device leads (1509, 1510).

The first and second diodes D1 (1513) and D2 (1514) are diodes (e.g., Zener diodes) configured to allow current to flow not only from its anode to its cathode, but also in the reverse direction, when a predetermined voltage (e.g., Zener voltage) is reached. The first and second diodes D1 (1513) and D2 (1514) are configured to protect circuits from overvoltage. For example, the first and second diodes D1 (1513) and D2 (1514) may be configured to shunt high voltages away from the second electronic device (e.g., cardiac stimulator (1501)).

Figure 17:
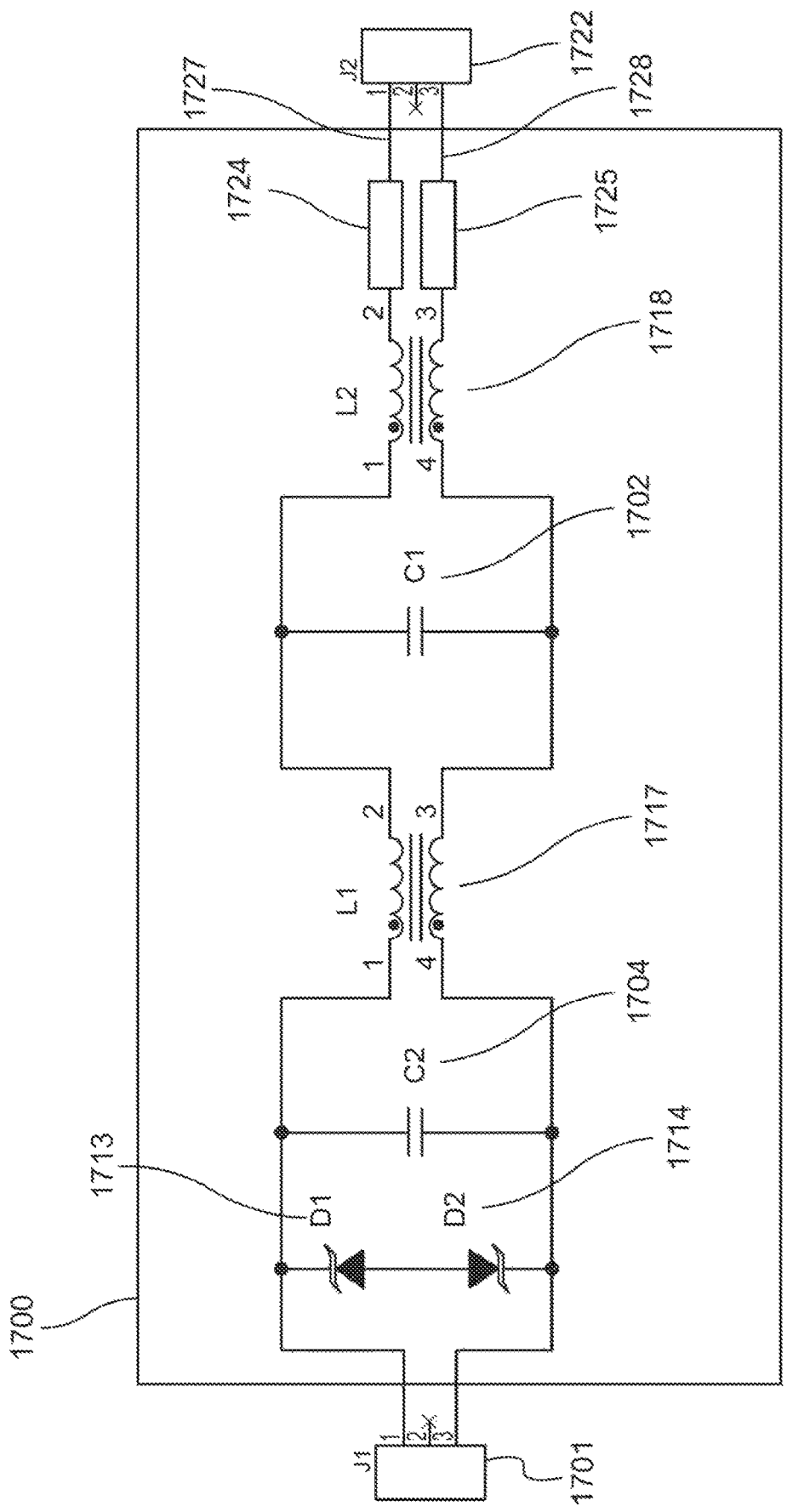
FIG. 17 is a circuit diagram of a protection device in a non-tuned common mode, according to embodiments.

FIG. 17 illustrates a circuit diagram of a protection circuit (1700) in a non-tuned common mode format. Similar to the protection circuit (1500) in FIG. 15, the protection circuit (1700) may be configured to suppress an induced voltage and induced common mode currents in pacing device leads (1727, 1728) by the pulse waveform generated by the signal generator (not shown in FIG. 17). Inductors (1724, 1725) (e.g., chokes) may add a further measure of large-current suppression, whether common-mode or differential mode. Further, in addition to the non-tuned common mode, a protection circuit may also include circuitry to operate in a non-tuned common-differential mode (as described with respect to FIG. 18) and a tunable mode (as described with respect to FIGS. 20A-24).

The signal generator may be structurally and/or functionally similar to the signal generator (1309) described with respect to FIG. 13 or the signal generator (1405) described with respect to FIG. 14. The protection circuit (1700) may be configured to be coupled to the second electronic device (e.g., cardiac simulator (1701)) and the pacing device leads (1727, 1728). The pacing device leads (1727, 1728) may be included within a first electronic device (e.g., pacing device) (1722) that may be introduced into a cardiac chamber of a patient. The second electronic device (e.g., cardiac stimulator (1701)) may be configured to generate a heart pacing signal to be delivered to the patient (1722). The protection circuit (1700) may include a first common mode transformer L2 (1718), a second common mode transformer L1 (1717), a first capacitor C1 (1702), a second capacitor C2 (1704), a first and second diode (1713, 1714), and first and second inductors (e.g., chokes) (1724, 1725).

The first common mode transformer L2 (1718), the second common mode transformer L1 (1717), the first capacitor C1 (1702), the second capacitor C2 (1704), and the first and second diodes (1713, 1714) may be structurally and/or functionally similar to the first common mode transformer L2 (1507), the second common mode transformer L1 (1505), the first capacitor C1 (1502), the second capacitor C2 (1504), and the first and second diodes (1513, 1514) respectively described with respect to FIG. 15. The first common mode transformer (1718) and the second common mode transformer (1717) may be configured to suppress induced common mode currents in the leads (1727, 1728), as a high-impedance element for common mode currents. The first capacitor C1 (1702) and the second capacitor C2 (1704) may short relatively high frequencies (higher than the lower end of the band-stop range) across the pacing device leads (1727, 1728) and suppress induced currents from flowing in the pacing device leads (1727, 1728). The first and second diodes D1 (1713) and D2 (1714) may be configured to shunt high voltages away from the second electronic device (e.g., cardiac stimulator (1701)).

The first and second inductors (1724, 1725) may be configured to block or suppress induced higher-frequency alternating current (AC), while passing lower-frequency current and/or direct current (DC). In some instances, the first and second inductors (1724, 1725) may be configured to suppress induced currents for frequencies corresponding to the lower or the higher end of a predetermined band-stop range. In some instances, a first inductor (1724) may be coupled to a first pacing device lead (1727) and a second inductor (1725) may be coupled to a second pacing device lead (1728).

Figure 18:
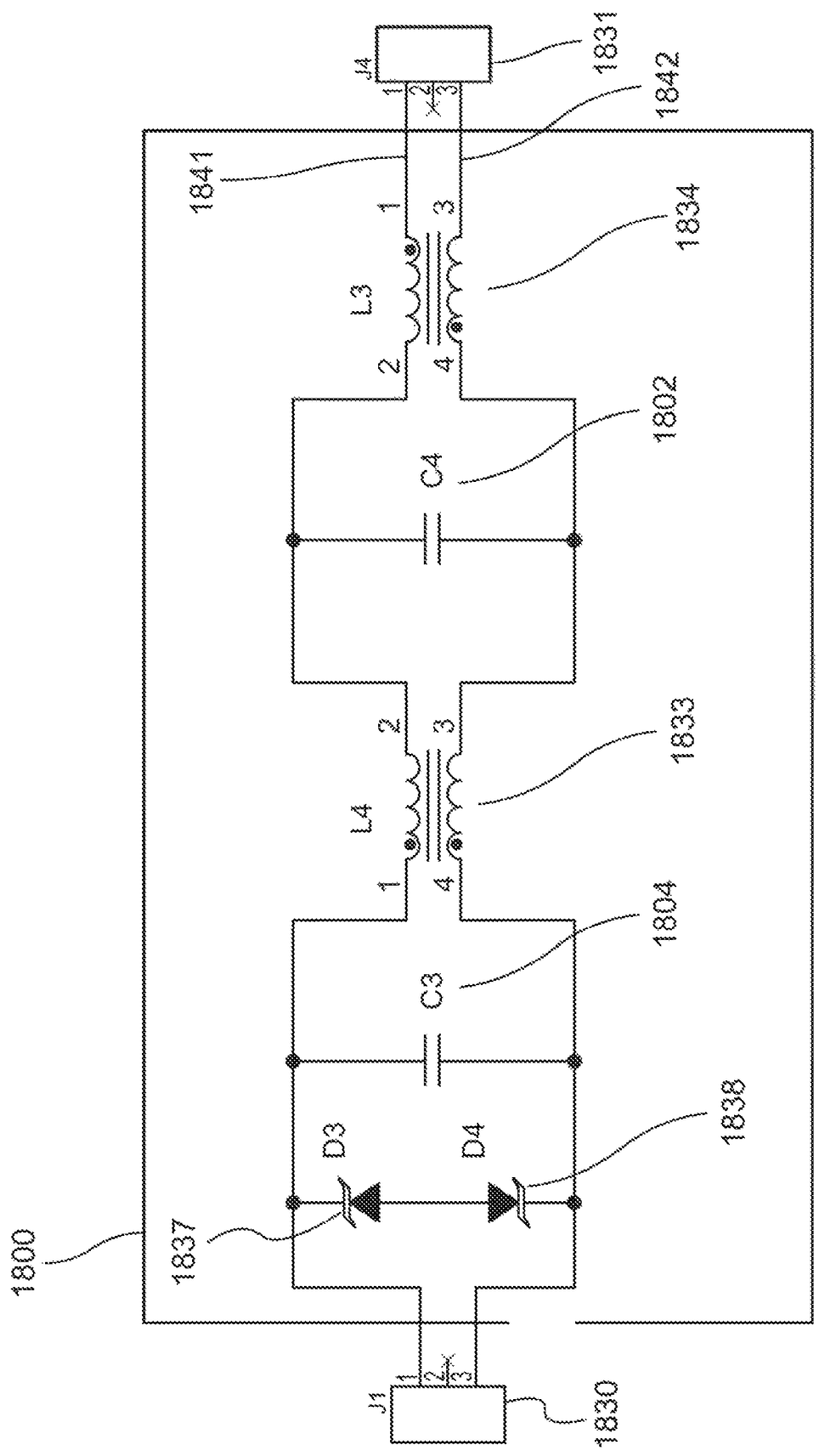
FIG. 18 is a circuit diagram of a protection device in a non-tuned common-differential mode, according to embodiments.

FIG. 18 illustrates a circuit diagram of a protection circuit (1800) in a non-tuned common-differential mode. Similar to the protection circuit (1500) in FIG. 15, the protection circuit (1800) may be configured to suppress induced voltages and induced common mode currents in pacing device leads (1841, 1842) by the pulse waveform generated by a signal generator (now shown in FIG. 18), as well as induced differential mode currents. Generally, the protection circuit may be operated in a non-tuned common mode (as described with respect to FIGS. 15 and 17), a non-tuned common-differential mode (as described herein with respect to FIG. 18), and/or a tunable mode (as described with respect to FIGS. 20A-24).

The signal generator may be structurally and/or functionally similar to the signal generator (1309) described with respect to FIG. 13 or the signal generator (1405) described with respect to FIG. 14. The protection circuit (1800) may be configured to be coupled to a second electronic device (e.g., cardiac simulator (1830)) and the first and second pacing device leads (1841, 1842). The first and second pacing device leads (1841, 1842) may be included within a first electronic device (1831) (e.g., pacing device) that may be introduced into a cardiac chamber of a patient. The second electronic device (1830) (e.g., cardiac stimulator) may be configured to generate a heart pacing signal to be delivered to a patient. The protection circuit (1800) may include a first differential mode transformer L3 (1834), a second common mode transformer L4 (1833), a first capacitor C4 (1802), a second capacitor C3 (1804), and first and second Zener diodes (1837, 1838).

Figure 19:
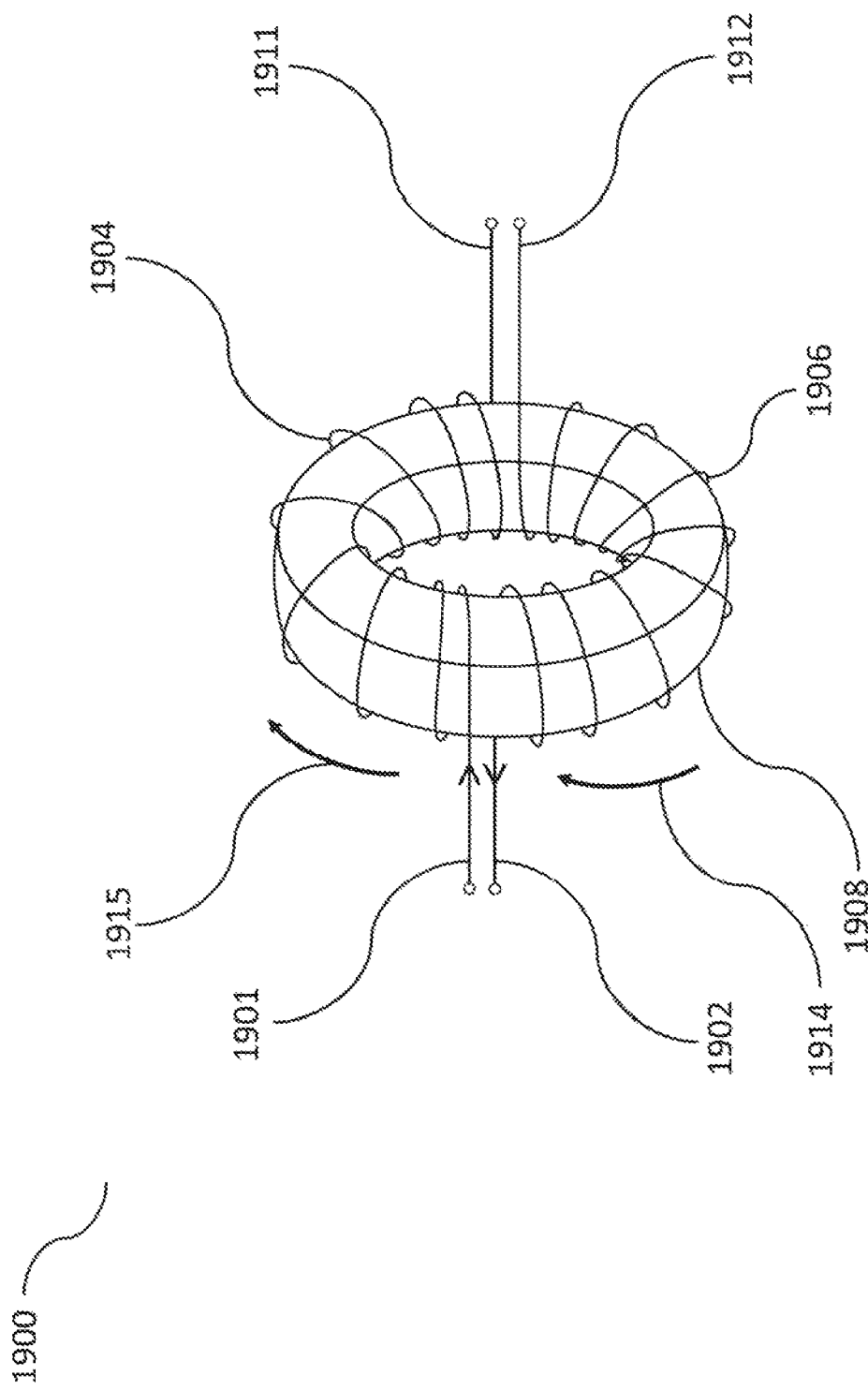
FIG. 19 is a perspective view of a differential mode transformer, according to embodiments.

The first differential mode transformer L3 (1834) is described with respect to FIG. 19. As shown in FIG. 19, a differential mode transformer (1900) includes a toroid core (1908), a first winding (1901, 1911), and a second winding (1902, 1912). The toroid core (1908) may include and/or be composed of a soft magnetic material that has a high magnetic permeability (e.g., iron) in a ring shape. The toroid core (1908) may be chosen to have a construction with relatively broad laminations to allow losses in the core (1908). The first winding (1901, 1911) may wind around a body of the core (1908) in a first direction, and the second winding (1902, 1912) may wind around the body of the core (1908) in a second direction opposite the first direction. The first winding (1901, 1911) may wind along the circumferential axis of the core (1908) in a first direction (e.g., a counterclockwise direction as shown in FIG. 19) and the second winding (1902, 1912) may wind around the circumferential axis of the core (1908) also in the first direction (e.g., a counterclockwise direction). Similar to the toroid core (1608) in the common mode transformer (1600) in FIG. 16, in some instances, the outer radius of the core (1908) may be between about 4 cm and about 10 cm, and the inner radius of the core (1908) may be between about 2 cm and about 9 cm. In some instances, the thickness of the core (1908) may be between about 1 cm and about 6 cm. In some instances, the number of turns/windings on each winding (1901, 1902) may be between about 3 and about 50.

A differential mode current with a non-zero frequency flowing through the first winding (1901, 1911) in a first direction (e.g., left-to-right in FIG. 19) may generate a first magnetic field in the core (1908) in the first direction that is indicated by arrow (1915). In this differential mode, the current flowing through the second winding (1902, 1912) is in a second direction opposite to the first direction (e.g., right-to-left in FIG. 19) and generates a second magnetic field in the same direction (1914). The magnitudes of the first magnetic field and the second magnetic field may be similar or equal. In other words, the winding configuration of the differential mode transformer (1900) allows currents flowing in opposite directions through the first winding (1901, 1911) and the second winding (1902, 1912) (e.g., a differential mode current) to induce a magnetic field in the toroid core (1908) that points in the same direction (1914, 1915). These in-phase magnetic fields may add together, resulting in a high impedance to the differential mode current flowing though the coupled pacing device leads (e.g., 1841, 1842 in FIG. 18). The impedance to the differential mode current may further include a real component (e.g., due to resistive core losses) in addition to an imaginary component (e.g., due to a high inductance of the core winding). This high impedance of the differential mode transformer (1900) may act to suppress, reduce, or minimize the magnitude of the differential mode current though a set of pacing device leads. In some embodiments, the combination of a differential mode transformer L3 (1834) and a common mode transformer L4 (1833) may be configured to suppress induced common mode current and induced differential mode current in a predetermined band-stop frequency range.

Returning to FIG. 18, the common mode transformer L4 (1833), the first capacitor C4 (1802), the second capacitor C3 (1804), and the first and second diodes (1837, 1838) are structurally and/or functionally similar to the second common mode transformer L1 (1505), the first capacitor C1 (1502), the second capacitor C2 (1504), and the first and second diodes (1513, 1514) respectively described with respect to FIG. 15. The common mode transformer L4 (1833) may be configured to suppress common mode currents in the leads, as a high-impedance element for common mode currents. The first capacitor C4 (1802) and the second capacitor C3 (1804) may short relatively high frequencies (higher than the lower end of the band-stop range) across the pacing device leads (1841, 1842) and suppress induced currents from flowing in the pacing device leads (1841, 1842). The first and second diodes D3 (1837) and D4 (1838) may be configured to shunt high voltages away from the second electronic device (e.g., cardiac stimulator (1830)).

Figure 20A:
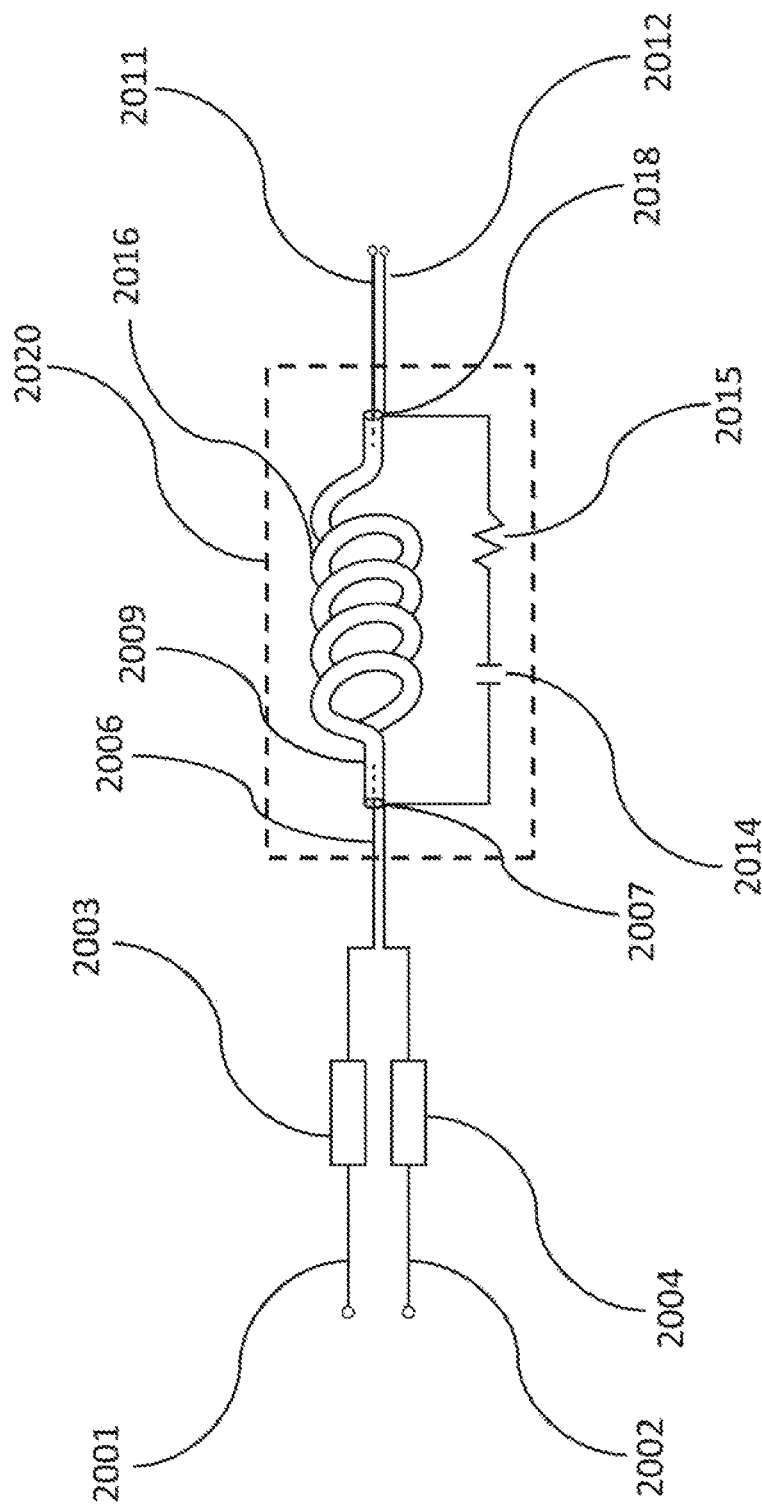
FIGS. 20A-20B are circuit diagrams of a tunable protection device, according to embodiments.
Figure 20B:
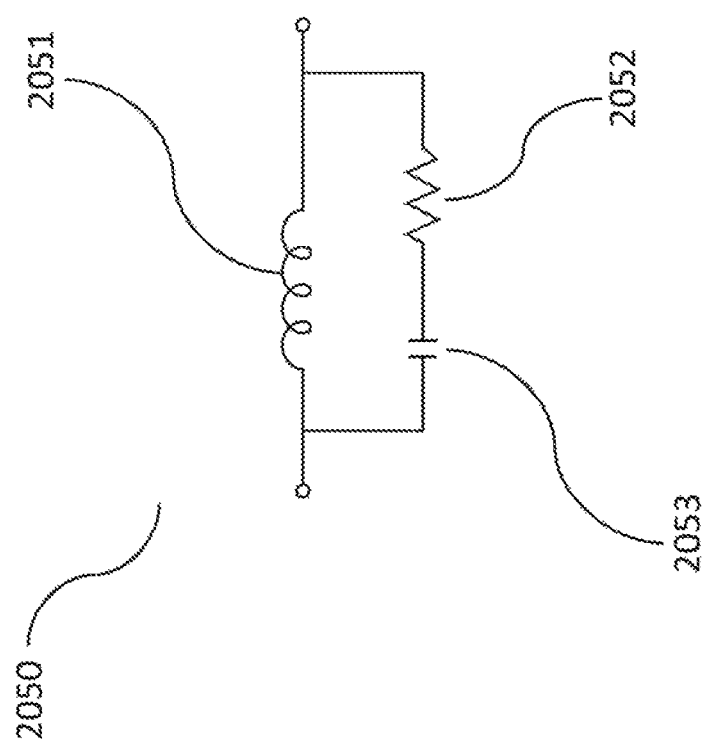

FIGS. 20A-20B illustrates a circuit diagram of a protection device including a tunable circuit (2020) (e.g., balun circuit). The balun circuit (2020) may be configured to join a balanced line (e.g., two conductors with equal currents in opposite directions) to an unbalanced line (e.g., one conductor and a ground, coaxial cable). The balun circuit (2020) may be configured to convert an unbalanced signal to a balanced signal by suppressing common mode currents. In some embodiments, the balun circuit (2020) may be configured to provide impedance transformation in addition to conversion between balanced and unbalanced signal modes. The balun circuit (2020) may be implemented in any of the protection devices described herein (e.g., described with respect to FIGS. 15, 17, and 18).

As shown in FIG. 20A, in some embodiments, the balun circuit (2020) may be coupled to a first and second inductor (e.g., choke) (2003, 2004). The first and second inductors (2003, 2004) may be configured to suppress large currents for frequencies corresponding to the lower or the higher end of a predetermined band-stop range. In some embodiments, a first inductor (2003) may be coupled to a first pacing device lead (2001) and a second inductor (2004) may be coupled to a second pacing device lead (2002). The pacing device leads (2001, 2002) may be coupled to a first electronic device (not shown) that is introduced into a cardiac chamber of a patient. The balun circuit (2020) may be coupled to a second electronic device (e.g., cardiac stimulator) (not shown) via third and fourth leads (2011, 2012).

In some embodiments, the balun circuit (2020) may include a coaxial cable (2009) formed into a coaxial winding (2016) having a center conductor (configured to carry a signal) connected to first lead (2001) at a first junction (2006) and having a shield conductor (configured to connect to electrical ground) connected to a second lead (2002) at second junction (2007). A capacitor (2014) connected in series with a resistor (2015) may be coupled in parallel and across the length of the coaxial cable (2009) at second junction (2007) and third junction (2018) (i.e., the capacitor (2014) and the resistor (2015) can be connected to shield conductor of the coaxial cable (2009) at second junction (2007) and third junction (2018). The coaxial cable (2009) may be coupled to third and fourth leads (2011, 2012).

FIG. 20B illustrates an equivalent circuit diagram (2050) of the tunable balun circuit (2020) in FIG. 20A. A coaxial shield conductor of the coaxial winding (2016) is represented, as shown in FIG. 20B, by an equivalent inductor (2051). The inductor (2051) may be coupled in parallel with a serially-connected capacitor (2053) and resistor (2052). The capacitor (2053) may be configured to resonate with the inductor (2051). For example, a vector network analyzer may be configured to select a capacitance value of the capacitor (2053). A resistance value of the resistor (2052) may be selected to configure a width and height of a resonance peak as described in more detail with respect to FIGS. 21, 23, and 24.

Figure 21:
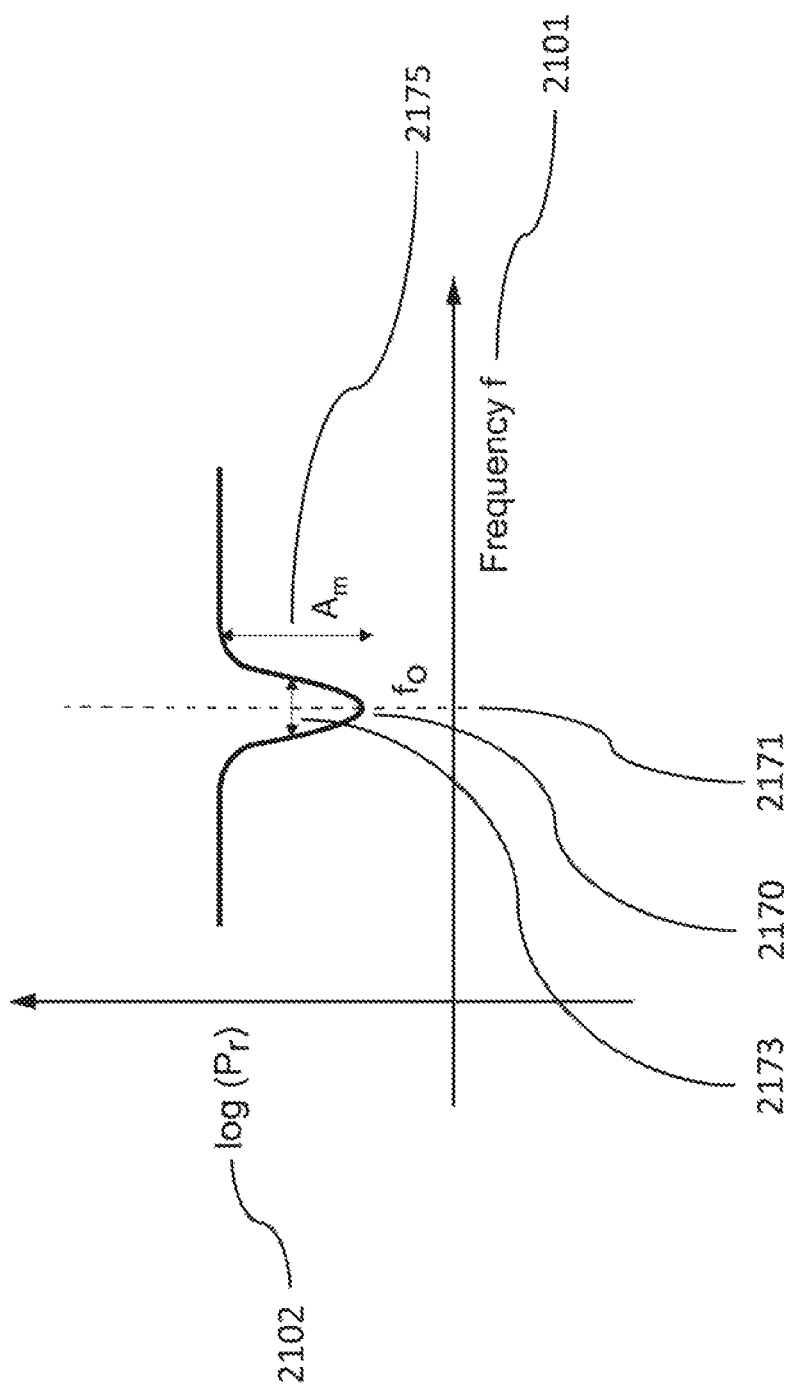
FIG. 21 is a plot of a resonance peak and frequency of the tunable protection device of FIGS. 20A-20B, according to embodiments.

FIG. 21 is a schematic illustration of a resonance peak obtained using a tunable circuit (e.g., balun circuit). The balun circuit can be structurally and/or functionally similar to the balun circuit (2020) described with respect to FIG. 20A. When power is transmitted through the shield of a coaxial winding, the ratio ($P_r$) of the power transmitted through the shield of the winding may be measured with, for example, a network analyzer. The plot in FIG. 21 illustrates the logarithmic function of transmitted power ($P_r$) (2102) as a function of the frequency f (2101). The resonance has a peak (2170) at a frequency $f_0$ (2171) where the height $A_m$ of the peak (2175) corresponds to power attenuation of $f_0$. The resonance frequency $f_0$ (2171) may be adjusted by selecting the capacitance value of a capacitor (e.g., capacitor (2014) in FIG. 20A) of a tunable circuit. In some instances, the circuit may be configured for high power attenuation. The breadth of the resonance peak (2173) may be measured, for example, by the full-width (2173) of the resonance peak at half-maximum height and may be adjusted by the resistance value of a resistor (e.g., resistor (2015) in FIG. 20A). In some instances, increasing a resistance value increases the breadth and reduces the height (2175) of the resonance peak (2173).

Figure 22:
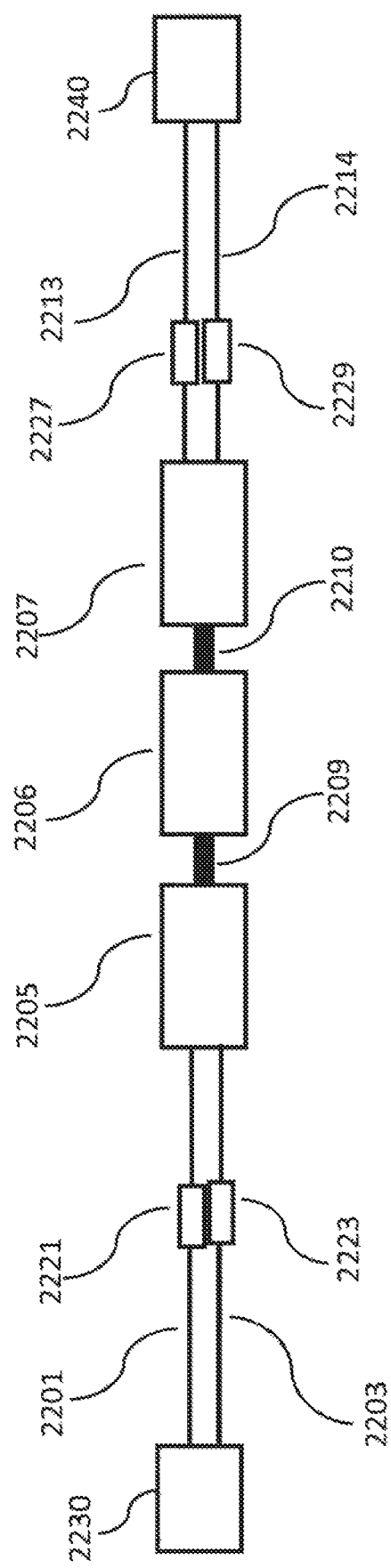
FIG. 22 is a circuit diagram of a series of tunable protection devices, according to embodiments.

FIG. 22 is a schematic illustration of a set of tunable circuits (e.g., sets of balun circuits). Each tunable balun circuit in the set of tunable circuits (2205, 2206, 2207) may be structurally and/or functionally similar to the tunable circuit (2020) as described with respect to FIG. 20A. The set of tunable circuits (2205, 2206, 2207) may be collectively configured as a broadband common mode suppression circuit in a protection device.

In some embodiments, the set of tunable circuits (2205, 2206, 2207) may be coupled to first and second inductors (e.g., chokes) (2221, 2223). The first and second inductors (2221, 2223) may be configured to suppress induced currents for frequencies corresponding to the lower or the higher end of a predetermined band-stop range. For example, a first inductor (2221) may be coupled to a first pacing device lead (2201) and a second inductor (2223) may be coupled to a second pacing device lead (2203). The first and second pacing device leads (2201, 2203) may be coupled to a first electronic device (e.g., pacing device) that is introduced into a cardiac chamber of a patient. The set of tunable circuits (2205, 2206, 2207) may be interconnected through respective coaxial lines (2209, 2210) and configured to attenuate common mode currents over a set of predetermined frequency ranges. Each tunable circuit in the set of tunable circuits (2205, 2206, 2207) may be configured for different frequency ranges such that their frequency response curves partially overlap (described with respect to FIG. 23). Thus, the set of tunable circuits (2205, 2206, 2207) may provide attenuation over overlapping frequency ranges to suppress common mode currents over a predetermined range of frequencies. The other end of the set of tunable circuits (2205, 2206, 2207) may be coupled to a second electronic device (e.g., cardiac stimulator) via third and fourth inductors (2227, 2229). The third and fourth inductors (2227, 2229) may be configured to suppress currents corresponding to frequencies on a lower or higher end of a predetermined band-stop range.

Figure 23:
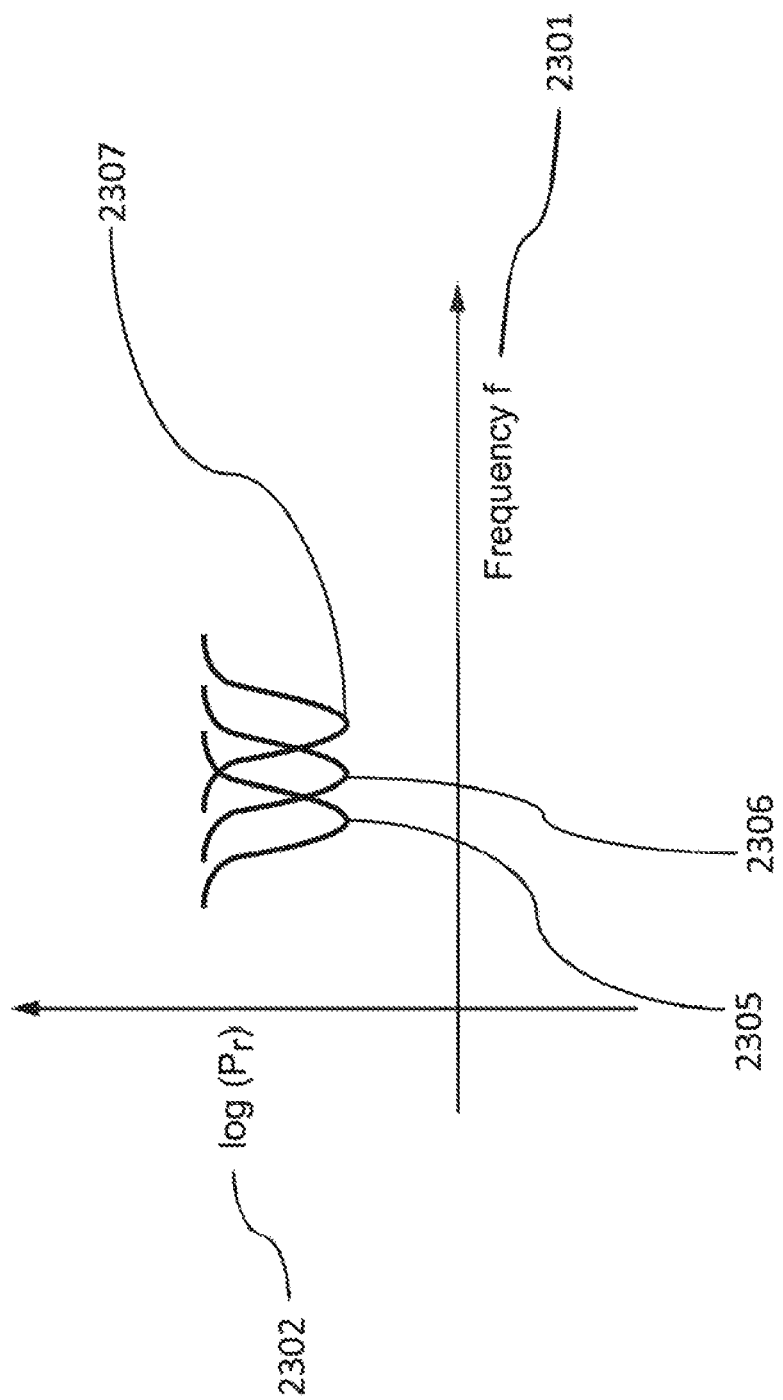
FIG. 23 is a plot of a set of resonance peaks and frequency of the tunable protection devices illustrated in FIG. 22, according to embodiments.

FIG. 23 is a schematic illustration of a set of resonance peaks of each tunable circuit of a set of tunable circuits (e.g. the set of tunable circuits (2205, 2206, 2207) in FIG. 22), according to embodiments. The power ($P_r$) is transmitted through a coaxial winding and may be measured with, for example, a network analyzer. The plot in FIG. 23 illustrates the logarithmic function of the transmitted power ($P_r$) (2302) as a function of the frequency f (2301). FIG. 23 illustrates respective resonance peaks (2305, 2306, 2307) of each tunable circuit of a set of tunable circuits (e.g. the set of tunable circuits (2205, 2206, 2207) in FIG. 22). For example, each tunable circuit in the set of tunable circuits (2205, 2206, 2207) may be configured such that the frequency response curves partially overlap.

Figure 24:
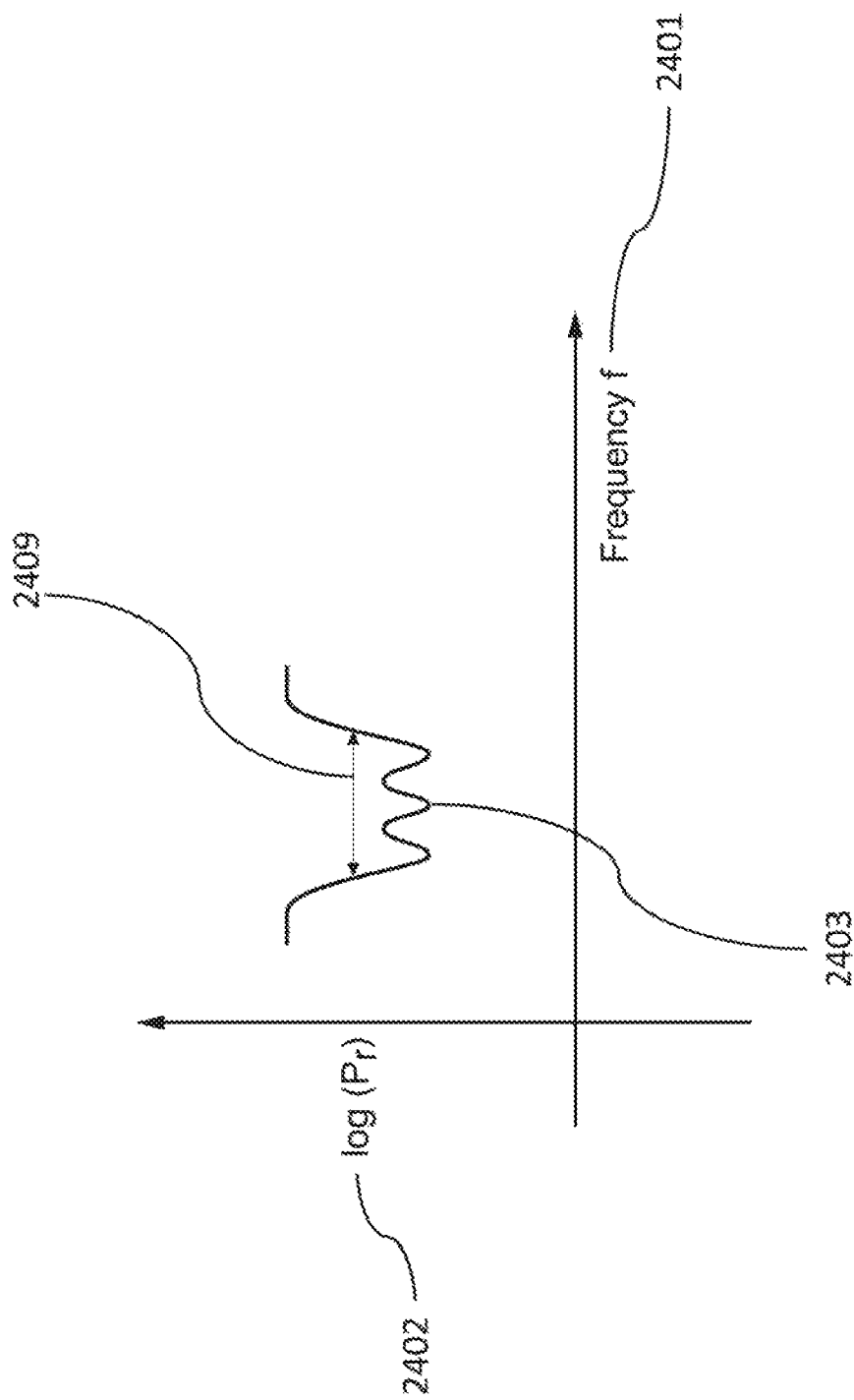
FIG. 24 is a plot of a set of resonance peaks and frequency of the tunable protection devices illustrated in FIG. 22, according to embodiments

FIG. 24 is a schematic illustration of a suppression of common mode currents by a set of tunable circuits (e.g., the set of tunable circuits (2205, 2206, 2207) in FIG. 22). The set of tunable circuits (e.g. the set of tunable balun circuits (2205, 2206, 2207) in FIG. 22) may have overlapping resonance frequencies, as described with respect to FIG. 23. FIG. 24 illustrates a net resonance peak (2403) from the set of tunable circuits. Similar to FIG. 23, the plot in FIG. 24 illustrates the logarithmic function of transmitted power ($P_r$) (2402) as a function of the frequency f (2401). The net effect of the set of tunable circuits may be broadband suppression over a range (2409) of frequencies from the partially overlapping frequency ranges.

Methods

Also described here are methods for protecting electronic circuitry from induced currents during a tissue ablation process performed in a heart chamber using the systems and devices described herein. The heart chamber may be the left atrial chamber and include its associated pulmonary veins. Generally, the methods described here include introducing and disposing a pacing device (e.g., pacing device (160), pacing device (1207)) in contact with one or more heart chambers. The pacing device may deliver a pacing signal to the heart using a cardiac stimulator (e.g., cardiac stimulator (150)) and/or measure cardiac activity. An ablation device (140, 1212) may be introduced and disposed in contact with one or more pulmonary vein ostial or antral regions. A pulse waveform may be delivered by one or more electrodes (e.g., electrodes (1213)) of the ablation device to ablate tissue. The pacing device may be electrically coupled to the system and configured to deliver pacing signals to the heart and/or measure cardiac activity. In some embodiments, a protection device may suppress the induced current and voltage from a first electronic device.

Additionally or alternatively, the pulse waveforms may include a plurality of levels of a hierarchy to reduce total energy delivery, e.g., as described in International Application Serial No. PCT/US2016/057664, filed Oct. 19, 2016, titled "Systems, apparatuses and methods for delivery of ablative energy to tissue," and incorporated herein by reference. The tissue ablation thus performed may be delivered in synchrony with paced heartbeats to reduce the risk of atrial and/or ventricular fibrillation and damage to healthy tissue. It should be appreciated that any of the ablation devices described herein (e.g., ablation device (140), ablation device (1212)) may be used to ablate tissue using the methods discussed below as appropriate.

In some embodiments, the ablation devices (e.g., ablation device (140), ablation device (1212)) described herein may be used for focal ablation of cardiac features/structures identified to cause arrhythmia (e.g., fibrillation). For example, a cardiac electrophysiology diagnostic catheter (e.g., mapping catheter) may be used to map areas with sources of arrhythmias that may be subsequently ablated through focal ablation using any of the ablation devices described herein. Focal ablation may, for example, create a spot lesion that neutralizes a rotor while sparing surrounding tissue. In some embodiments, one or more focal ablation lesions may be formed in combination with one or more box or line lesions to treat cardiac arrhythmia. As a non-limiting example, in some embodiments, a system may include one or more mapping catheters and one or more ablation devices (e.g., ablation device (140), ablation device (1212)) useful for creating lesions via focal ablation. Examples of suitable focal ablation catheters are described in International Application Serial No. PCT/US2019/014226, as incorporated herein by reference.

Figure 25:
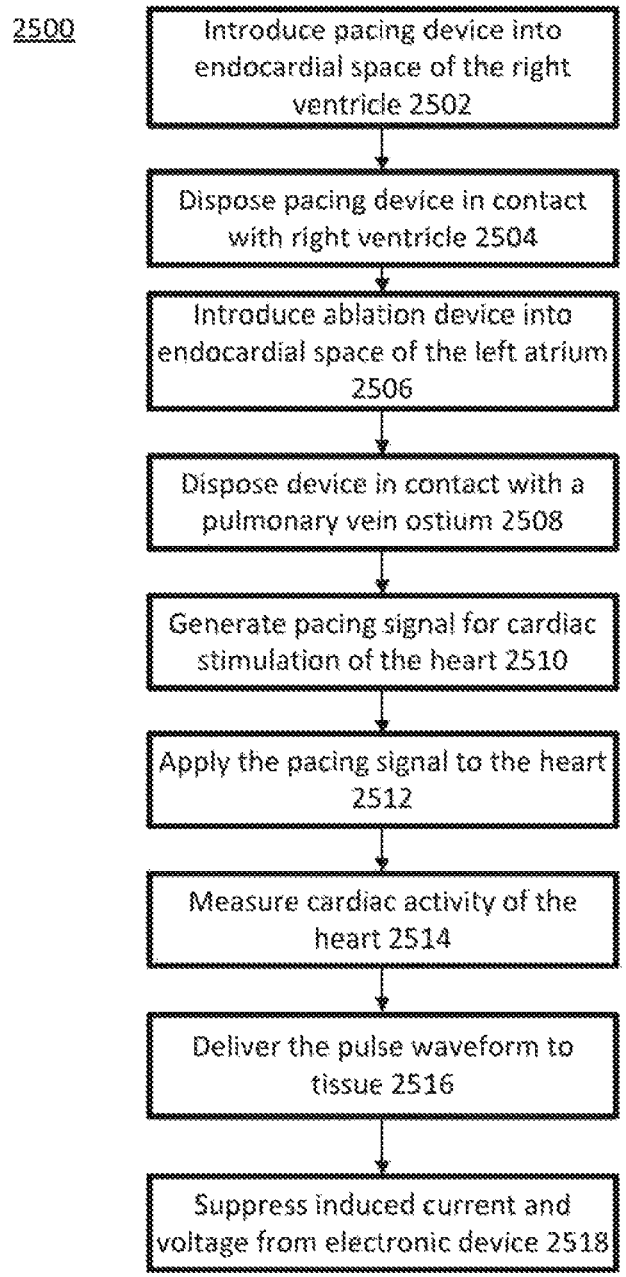
FIG. 25 illustrates a method for protecting electronic components from high voltage signals, according to embodiments.

FIG. 25 is an example method (2500) of tissue ablation. In some embodiments, the voltage pulse waveforms described herein may be applied during a refractory period of the cardiac cycle so as to avoid disruption of the sinus rhythm of the heart. The method (2500) includes introduction of a pacing device (e.g., pacing device (160, 1207)) into an endocardial space of a right ventricle, at (2502). The pacing device may be advanced to be disposed in contact with the right ventricle, at (2504). For example, sensor electrodes may be configured for cardiac activity measurement (e.g., ECG signals) and pacing electrodes may be configured for delivering pacing signals may be disposed in contact with an inner surface of the right ventricle. An ablation device (e.g., ablation device (140, 1212)) may be introduced into an endocardial space of a left atrium, at (2506). The ablation device may be advanced to be disposed in contact with a pulmonary vein ostium, at (2508). In one non-limiting example, electrodes of an ablation device may form an approximately circular arrangement of electrodes disposed in contact with an inner radial surface at a pulmonary vein ostium. In some embodiments, a pacing signal may be generated by a cardiac stimulator (e.g., cardiac stimulator (150, 1260)) for cardiac stimulation of the heart, at (2510). The pacing signal may then be applied to the heart, at (2512), using the pacing electrodes of the pacing device. For example, the heart may be electrically paced with the pacing signal to ensure pacing capture to establish periodicity and predictability of the cardiac cycle. One or more of atrial and ventricular pacing may be applied. Examples of applied pacing signals relative to patient cardiac activity are described in more detail herein.

In some embodiments, pacing capture may be automatically confirmed by one or more of the signal generator, processor (e.g., signal generator (110, 1250)), and confirmed by a user. For example, the user may confirm pacing capture using a user interface (e.g., an input/output device such as a touch screen monitor or other type of monitor) based on measured cardiac activity signals. If the signal generator, processor, and/or the user viewing the displayed cardiac output, determines that there is an absence of pacing capture, pulse waveform generation may be prohibited and the user may be prompted to adjust system parameters by, for example, repositioning the pacing device to improve tissue engagement and/or modify pacing signal parameters (e.g., pulse width, pulse amplitude, pulse frequency, etc.).

In some embodiments, the pacing device may further measure cardiac activity (e.g., ECG signals) corresponding to electrical cardiac activity of the heart, at (2514). For example, the measured cardiac activity may include a measured cardiac pacing pulse, R-wave, and high voltage signals. One or more of the measured cardiac activity parameters may be used to generate a protection signal.

The generated pulse waveform may be delivered to tissue for ablation, at (2516). In some embodiments, a refractory time period may follow a pacing signal. For example, a common refractory time period may be between both atrial and ventricular refractory time windows. A voltage pulse waveform may be applied in the common refractory time period. In some embodiments, the pulse waveform may be generated with a time offset with respect to the indication of the pacing signal. For example, the start of a refractory time period may be offset from the pacing signal by a time offset. The voltage pulse waveform(s) may be applied over a series of heartbeats over corresponding common refractory time periods.

Current and voltage induced in the pacing device are suppressed from an electronic device by a protection device, at (2518). For example, the protection device suppresses an induced current and voltage from coupling to a cardiac stimulator and/or other components coupled to the protection device.

Figure 26:
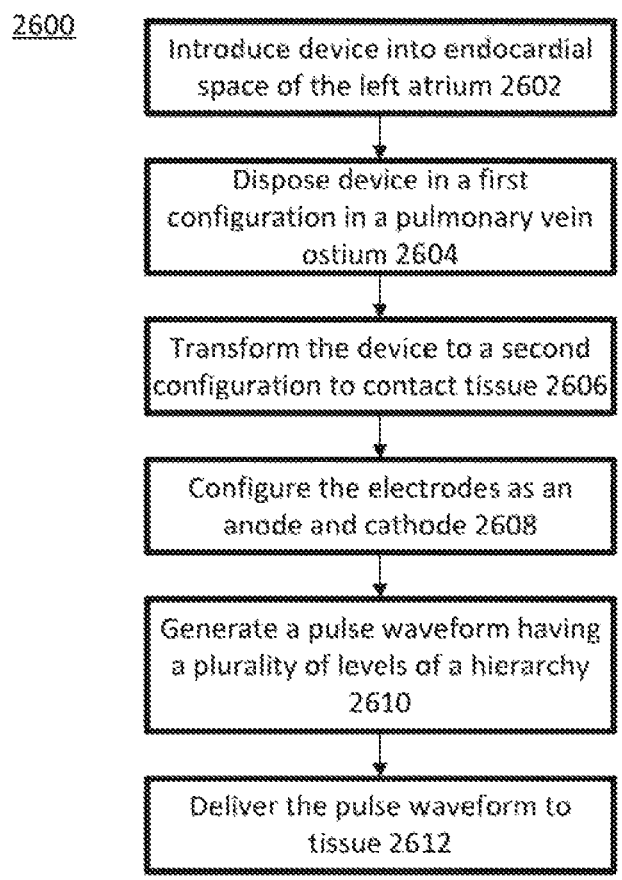
FIG. 26 illustrates a method for tissue ablation, according to embodiments.

In some embodiments, hierarchical voltage pulse waveforms having a nested structure and a hierarchy of time intervals as described herein may be useful for irreversible electroporation, providing control and selectivity in different tissue types. FIG. 26 is a flowchart (2600) of another example method of a tissue ablation process. The method (2600) includes the introduction of a device (e.g., ablation device (140, 1212)) into an endocardial space of a left atrium, at (2602). The device may be advanced to be disposed in a pulmonary vein ostium, at (264). In embodiments where the device may include a first and second configuration (e.g., compact and expanded), the device may be introduced in the first configuration and transformed to a second configuration to contact tissue at or near the pulmonary vein antrum or ostium, at (2606). The device may include electrodes and may be configured in anode-cathode subsets, at (2608), as discussed in detail above. For example, a subset of electrodes of the devices may be selected as anodes, while another subset of electrodes of the device may be selected as cathodes, with the voltage pulse waveform applied between the anodes and cathodes.

A pulse waveform may be generated by a signal generator (e.g., the signal generator (110)) and may include a plurality of levels in a hierarchy, at (2660). A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval. The pulse waveform generated by the signal generator (e.g., signal generator (110)) may be delivered to tissue using the ablation device, at (2612).

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). As discussed above, one or more of the waveforms applied across the anode-cathode subsets may be applied during the refractory period of a cardiac cycle. The pulse waveform may be delivered to tissue. It should be appreciated that the steps described in FIGS. 25 and 26 may be combined and modified as appropriate.

In some embodiments, the pulse waveform may be delivered to pulmonary vein ostium of a patient via a set of splines of an ablation device. In some embodiments, voltage pulse waveforms as described herein may be selectively delivered to electrode subsets such as anode-cathode subsets for ablation and isolation of the pulmonary vein. For example, a first electrode of a group of electrodes may be configured as an anode and a second electrode of the group of electrodes may be configured as a cathode. These steps may be repeated for a desired number of pulmonary vein ostial or antral regions to have been ablated (e.g., 1, 2, 3, or 4 ostia). Suitable examples of ablation devices and methods are described in International Application No. PCT/US2019/014226.

Figure 6:
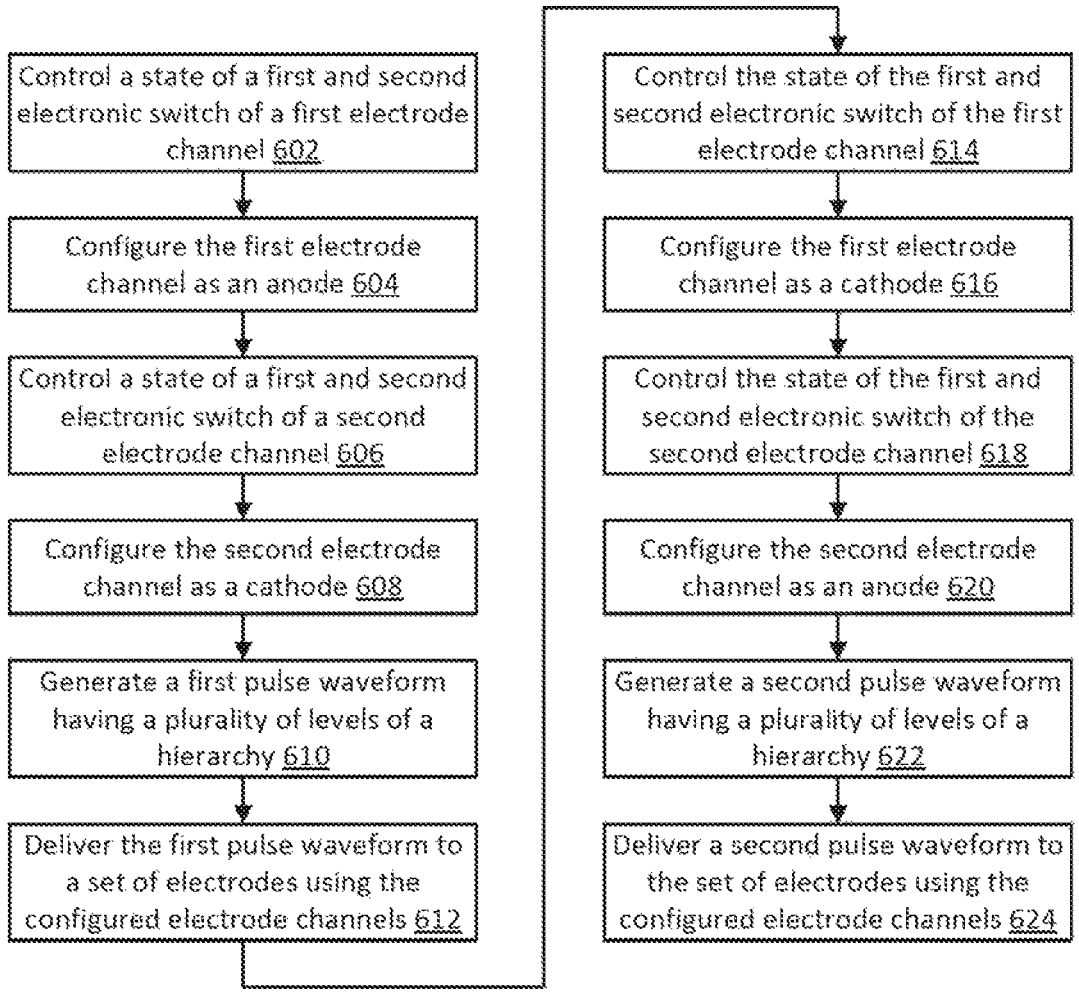
FIG. 6 illustrates a method for tissue ablation, according to embodiments.

FIG. 6 is a method (600) for one embodiment of a signal generation process using the systems and devices described herein. The method (600) includes controlling a state of a first and second electronic switch of a first electrode channel, at (602). For example, (602) may control a state of first electronic switch (220) and second electronic switch (230) of the first electrode channel (201) illustrated in FIG. 2. In some embodiments, a drive circuit (e.g., drive circuits (222, 232)) coupled to an electronic switch may be configured to control the state of the electronic switch. In some embodiments, the electronic switch may be configured to switch between an ON state and an OFF state using the drive circuit. The first electrode channel may be configured as an anode, at (604). A state of a first and second electronic switch of a second electrode channel may be controlled, at (606) by, for example, drive circuits controlling the ON/OFF states of respective electronic switches. The second electrode channel may be configured as a cathode, at (608).

In some embodiments, hierarchical voltage pulse waveforms having a nested structure and a hierarchy of time intervals, as described herein, may be useful for irreversible electroporation, as well as providing control and selectivity in different tissue types. In some embodiments, a first pulse waveform may be generated having a set of levels of a hierarchy, at (610). In some embodiments, a first level of a hierarchy of the first pulse waveform may include a first set of pulses, with each pulse having a pulse time duration. A first time interval may separate successive pulses. A second level of the hierarchy of the first pulse waveform may include a set of first sets of pulses as a second set of pulses with a second time interval separating successive first sets of pulses. The second time interval may be at least three times the duration of the first time interval. A third level of the hierarchy of the pulse waveform may include a set of second sets of pulses as a third set of pulses with a third time interval separating successive second sets of pulses. The third time interval may be at least thirty times the duration of the second level time interval. An energy source may deliver the first pulse waveform to a set of electrodes during use via the first electrode channel and the second electrode channel, at (612). The first pulse waveform may be delivered at a first time.

At a second time subsequent to the first time, the state of the first and second electronic switch of the first electrode channel may be controlled, at (614). The first electrode channel may be configured as a cathode, at (616). The state of the first and second electronic switch of the second electrode channel may be controlled, at (618). The second electrode channel may be configured as an anode, at (620). In some embodiments, a second pulse waveform may be generated having a set of levels of a hierarchy, at (622), such as including the first, second, and third hierarchy levels described herein. The energy source may deliver the second pulse waveform to the set of electrodes during use via the first electrode channel and the second electrode channel at the second time, at (624).

Pulse Waveform

Disclosed herein are methods, systems and devices for the selective and rapid application of pulsed electric fields/waveforms to effect tissue ablation with irreversible electroporation. The pulse waveform(s) as disclosed herein are usable with any of the systems (100, 200, 300), ablation devices (e.g., 140, 400, 500), and methods (e.g., 600) described herein. Some embodiments are directed to pulsed high voltage waveforms together with a sequenced delivery scheme for delivering energy to tissue via sets of electrodes. In some embodiments, peak electric field values may be reduced and/or minimized while at the same time sufficiently large electric field magnitudes may be maintained in regions where tissue ablation is desired. This also reduces the likelihood of excessive tissue damage or the generation of electrical arcing, and locally high temperature increases. In some embodiments, a system useful for irreversible electroporation may include a signal generator capable of being configured to deliver pulsed voltage waveforms to a set of electrodes of an ablation device. In some embodiments, a processor of the signal generator is configured to control a set of electrode channels whereby selected pairs of anode-cathode subsets of electrodes may be sequentially triggered based on a predetermined sequence, and in one embodiment the sequenced delivery may be triggered from a cardiac stimulator and/or pacing device. In some embodiments, the ablation pulse waveforms may be applied in a refractory period of the cardiac cycle so as to avoid disruption of the sinus rhythm of the heart. One example method of enforcing this is to electrically pace the heart with a cardiac stimulator (e.g., cardiac stimulator (150)) and ensure pacing capture to establish periodicity and predictability of the cardiac cycle, and then to define a time window well within the refractory period of this periodic cycle within which the ablation waveform is delivered.

In some embodiments, the pulsed voltage waveforms disclosed herein are hierarchical in organization and have a nested structure. In some embodiments, the pulsed waveform includes hierarchical groupings of pulses with a variety of associated timescales. Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered. This in turn may broaden the areas of clinical application of electroporation including therapeutic treatment of a variety of cardiac arrhythmias.

Figure 7:
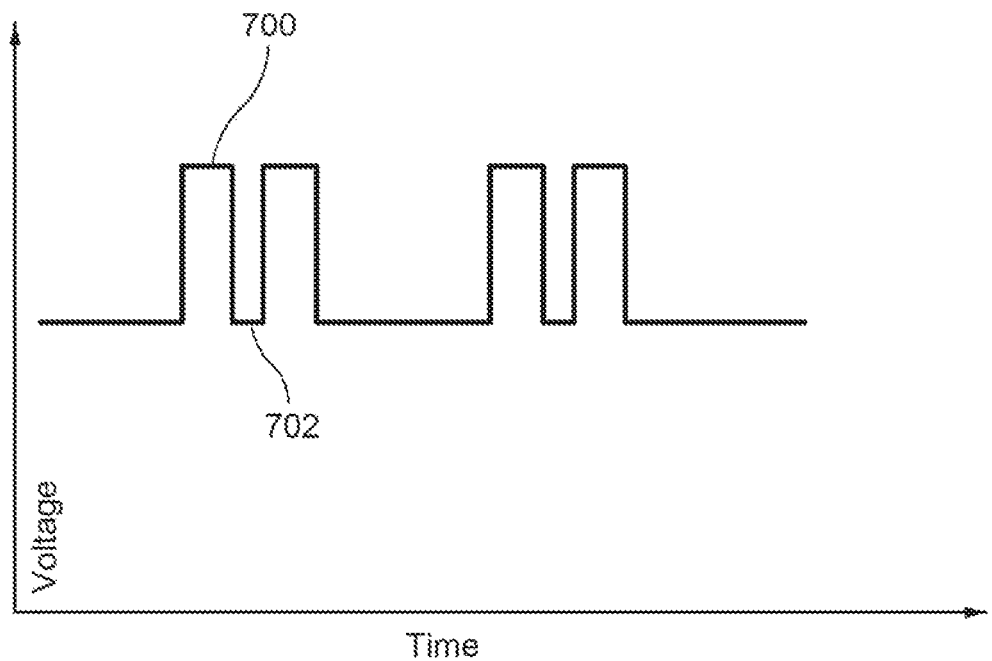
FIG. 7 is an example waveform showing a sequence of voltage pulses with a pulse width defined for each pulse, according to embodiments.

FIG. 7 illustrates a pulsed voltage waveform in the form of a sequence of rectangular double pulses, with each pulse, such as the pulse (700) being associated with a pulse width or duration. The pulse width/duration may be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 7 illustrates a set of monophasic pulses where the polarities of all the pulses are the same (all positive in FIG. 7, as measured from a zero baseline). In some embodiments, such as for irreversible electroporation applications, the height of each pulse (700) or the voltage amplitude of the pulse (700) may be in the range from about 400 V, about 1,000 V, about 5,000 V, about 10,000 V, about 15,000 V, including all values and sub ranges in between. As illustrated in FIG. 7, the pulse (700) is separated from a neighboring pulse by a time interval (702), also sometimes referred to as a first time interval. The first time interval may be about 10 microseconds, about 50 microseconds, about 100 microseconds, about 200 microseconds, about 500 microseconds, about 800 microseconds, about 1 millisecond including all values and sub ranges in between, in order to generate irreversible electroporation.

Figure 8:
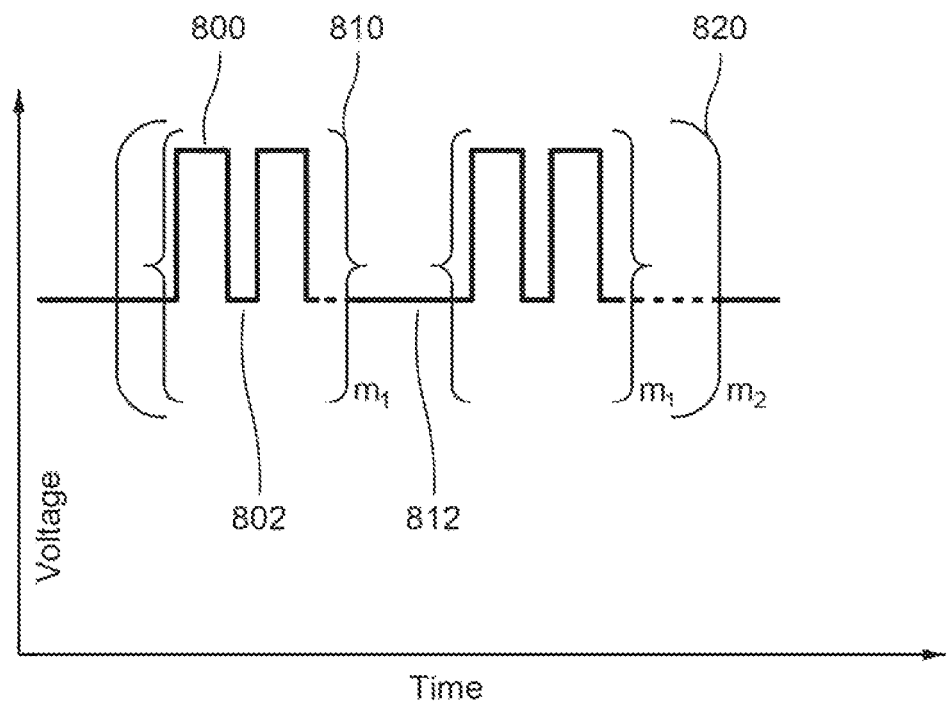
FIG. 8 schematically illustrates a hierarchy of pulses showing pulse widths, intervals between pulses, and groupings of pulses, according to embodiments.

FIG. 8 introduces a pulse waveform with the structure of a hierarchy of nested pulses. FIG. 8 shows a series of monophasic pulses such as pulse (800) with pulse width/pulse time duration w, separated by a time interval (also sometimes referred to as a first time interval) such as (802) of duration $t_1$ between successive pulses, a number $m_1$ of which are arranged to form a group of pulses (810) (also sometimes referred to as a first set of pulses). Furthermore, the waveform has a number $m_2$ of such groups of pulses (also sometimes referred to as a second set of pulses) separated by a time interval (812) (also sometimes referred to as a second time interval) of duration $t_2$ between successive groups. The collection of $m_2$ such pulse groups, marked by (820) in FIG. 8, constitutes the next level of the hierarchy, which may be referred to as a packet and/or as a third set of pulses. The pulse width and the time interval $t_1$ between pulses may both be in the range of microseconds to hundreds of microseconds, including all values and sub ranges in between. In some embodiments, the time interval $t_2$ may be at least three times larger than the time interval $t_1$. In some embodiments, the ratio $t_2/t_1$ may be in the range between about 3 and about 300, including all values and sub-ranges in between.

Figure 9:
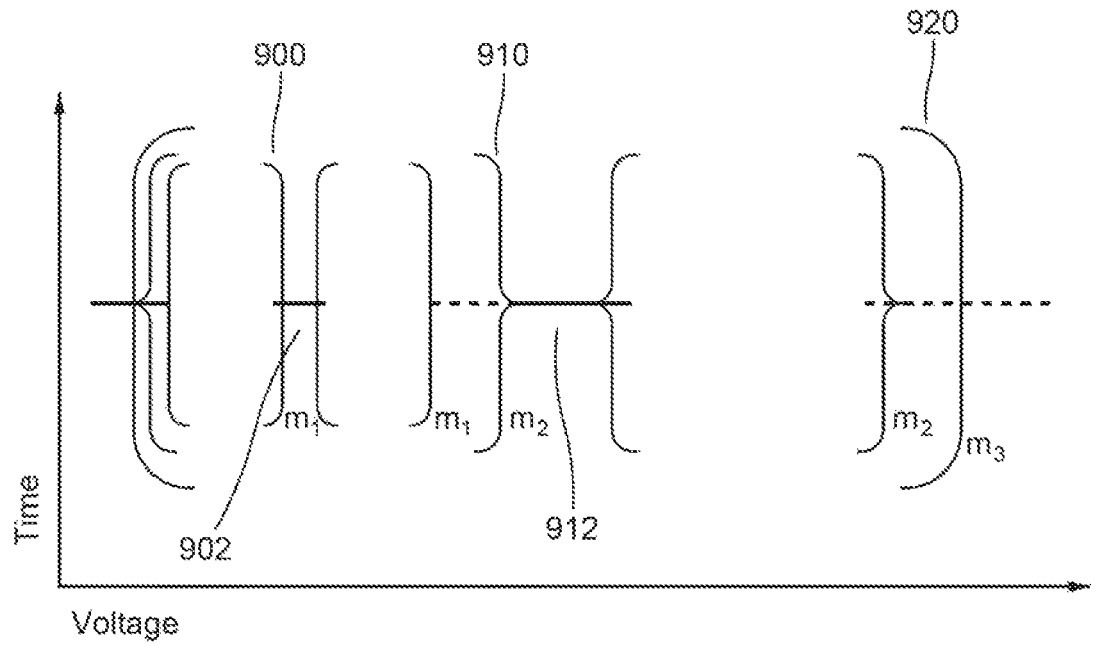
FIG. 9 provides a schematic illustration of a nested hierarchy of monophasic pulses displaying different levels of nested hierarchy, according to embodiments.

FIG. 9 further elaborates the structure of a nested pulse hierarchy waveform. In this figure, a series of $m_1$ pulses (individual pulses not shown) form a group of pulses (902) (e.g., a first set of pulses). A series of $m_2$ such groups separated by an inter-group time interval (910) of duration $t_2$ (e.g., a second time interval) between one group and the next form a packet (910) (e.g., a second set of pulses). A series of $m_3$ such packets separated by time intervals (912) of duration $t_3$ (e.g., a third time interval) between one packet and the next form the next level in the hierarchy, a super-packet labeled (920) (e.g., a third set of pulses) in the figure. In some embodiments, the time interval $t_3$ may be at least about thirty times larger than the time interval $t_2$. In some embodiments, the time interval $t_3$ may be at least fifty times larger than the time interval $t_2$. In some embodiments, the ratio $t_3/t_2$ may be in the range between about 30 and about 800, including all values and sub-ranges in between. The amplitude of the individual voltage pulses in the pulse hierarchy may be anywhere in the range from 500 V to 7,000 V or higher, including all values and sub-ranges in between.

Figure 10:
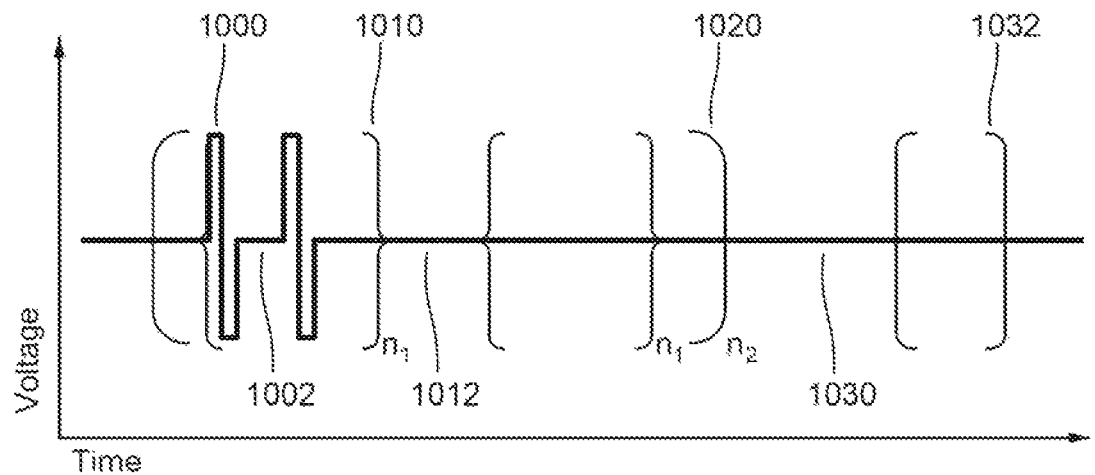
FIG. 10 is a schematic illustration of a nested hierarchy of biphasic pulses displaying different levels of nested hierarchy, according to embodiments.

FIG. 10 provides an example of a biphasic waveform sequence with a hierarchical structure. In the example shown in the figure, biphasic pulses (1000) have a positive voltage portion as well as a negative voltage portion to complete one cycle of the pulse. There is a time delay (1002) (e.g., a first time interval) between adjacent cycles of duration $t_1$, and $n_1$ such cycles form a group of pulses (1010) (e.g., a first set of pulses). A series of $n_2$ such groups separated by an inter-group time interval (1012) (e.g., a second time interval) of duration $t_2$ between one group and the next form a packet (1020) (e.g., a second set of pulses). The figure also shows a second packet (1032), with a time delay (1030) (e.g., a third time interval) of duration $t_3$ between the packets. Just as for monophasic pulses, higher levels of the hierarchical structure may be formed as well. The amplitude of each pulse or the voltage amplitude of the biphasic pulse may be anywhere in the range from 500 V to 7,000 V or higher, including all values and sub-ranges in between. The pulse width/pulse time duration may be in the range from nanoseconds or even sub-nanoseconds to tens of microseconds, while the delays $t_1$ may be in the range from zero to several microseconds. The inter-group time interval $t_2$ may be at least ten times larger than the pulse width. In some embodiments, the time interval $t_3$ may be at least about twenty times larger than the time interval $t_2$. In some embodiments, the time interval $t_3$ may be at least fifty times larger than the time interval $t_2$.

Embodiments disclosed herein may include waveforms structured as hierarchical waveforms that include waveform elements/pulses at various levels of the hierarchy. The individual pulses such as pulse (800) in FIG. 8 may include the first level of the hierarchy, and have an associated pulse time duration and a first time interval between successive pulses. A set of pulses, or elements of the first level structure, form a second level of the hierarchy such as the group of pulses/second set of pulses (810) in FIG. 8. Among other parameters associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses may be between about 20 microseconds and about 10 milliseconds, including all values and sub-ranges in between. A set of groups, second set of pulses, or elements of the second level structure, form a third level of the hierarchy such as the packet of groups/third set of pulses (820) in FIG. 8. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses may be between about 60 microseconds and about 200 milliseconds, including all values and sub-ranges in between. The generally iterative or nested structure of the waveforms may continue to a higher plurality of levels, such as ten levels of structure, or more.

In some embodiments, hierarchical waveforms with a nested structure and hierarchy of time intervals as described herein may be useful for irreversible electroporation ablation energy delivery, providing a good degree of control and selectivity for applications in different tissue types. A variety of hierarchical waveforms may be generated with a suitable pulse generator of the type described in this disclosure. It is understood that while the examples herein identify separate monophasic and biphasic waveforms for clarity, it should be noted that combination waveforms, where some portions of the waveform hierarchy are monophasic while other portions are biphasic, may also be generated/implemented.

Figure 11:
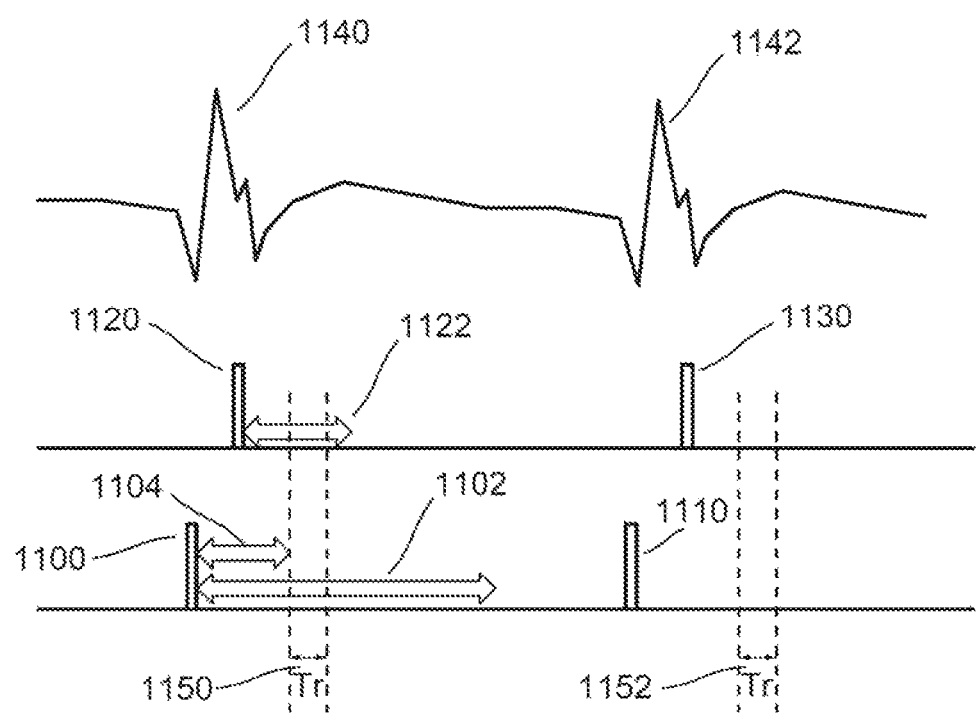
FIG. 11 illustrates schematically a time sequence of electrocardiograms and cardiac pacing signals together with atrial and ventricular refractory time periods and indicating a time window for irreversible electroporation ablation, according to embodiments.

In some embodiments, the ablation pulse waveforms described herein may be applied during the refractory period of the cardiac cycle so as to avoid disruption of the sinus rhythm of the heart. In some embodiments, a method of treatment may include electrically pacing the heart with a cardiac stimulator (e.g., cardiac stimulator (150)) to ensure pacing capture to establish periodicity and predictability of the cardiac cycle, and then defining a time window within the refractory period of the cardiac cycle within which one or more pulsed ablation waveforms may be delivered. FIG. 11 illustrates an example where both atrial and ventricular pacing is applied (for instance, with pacing leads or catheters situated in the right atrium and right ventricle respectively). With time represented on the horizontal axis, FIG. 11 illustrates a series of ventricular pacing signals (1100, 1110), and a series of atrial pacing signals (1120, 1130), along with a series of ECG waveforms (1140, 1142) that are driven by the pacing signals. As indicated in FIG. 11 by the thick arrows, there is an atrial refractory time window (1122) and a ventricular refractory time window (1102) that respectively follow the atrial pacing signal (1120) and the ventricular pacing signal (1100). As shown in FIG. 11, a common refractory time window (1150) of duration $T_r$, may be defined that lies within both atrial and ventricular refractory time windows (1122, 1102). In some embodiments, the electroporation ablation waveform(s) may be applied in this common refractory time window (1150). The start of this refractory time window (1150) is offset from the pacing signal (1100) by a time offset (1104) as indicated in FIG. 11.

The time offset (1104) may be smaller than about 25 milliseconds, in some embodiments. At the next heartbeat, a similarly defined common refractory time window (1152) is the next time window available for application of the ablation waveform(s). In this manner, the ablation waveform(s) may be applied over a series of heartbeats, at each heartbeat remaining within the common refractory time window. In one embodiment, each packet of pulses as defined above in the pulse waveform hierarchy may be applied over a heartbeat, so that a series of packets is applied over a series of heartbeats, for a given electrode set. Similarly, a first waveform packet may be delivered successively over a first sequence of electrodes, followed by a second waveform packet delivered over a second sequence of electrodes, and so on; in some cases, it may even be convenient for the second sequence of electrodes to be different from the first sequence of electrodes. The architecture of the signal generator and routing console as disclosed herein permits the delivery of a variety of such hierarchical waveforms wherein waveform packet delivery to a given set of electrodes, in the sense disclosed herein, may be interspersed with waveform packet deliveries to a different set of electrodes. This modality of interspersed waveform delivery described herein may include monophasic, biphasic, and mixed pulses that include both monophasic and biphasic components.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). As discussed above, one or more of the waveforms applied across the anode-cathode subsets may be applied during the refractory period of a cardiac cycle. It should be appreciated that the method steps described herein may be combined and modified as appropriate. Likewise, while the examples of electrode channel selection disclosed herein describe the selection of one anode and two cathode channels, it should be clear that a wide variety of channels may be selected to act as anodes or cathodes, without limitation.

It should be understood that while cardiac ablation devices are described here for ablation, the protection devices and embodiments disclosed herein are applicable to other clinical procedures and other ablation devices can be used without departing from the scope of the present invention.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some embodiments, the systems, devices, and methods may be in communication with other computing devices (not shown) via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, devices, and methods described herein may include a radiofrequency receiver, transmitter, and/or optical (e.g., infrared) receiver and transmitter to communicate with one or more devices and/or networks.

The specific examples and descriptions herein are exemplary in nature and embodiments may be developed by those skilled in the art based on the material taught herein without departing from the scope of the present invention, which is limited only by the attached claims.

We claim:

1. A system, comprising:
   a set of electrodes disposable near tissue of a subject;
   a signal generator configured to generate a voltage pulse waveform, the signal generator coupleable to the set of electrodes and configured to deliver the voltage pulse waveform to the set of electrodes to ablate the tissue, the set of electrodes configured to induce currents in a first electronic device disposed near the tissue in response to receiving the voltage pulse waveform, wherein the currents induced in the first electronic device include common mode currents; and
   a protection device coupleable between the first electronic device and a second electronic device, the protection device configured to reduce the currents induced in the first electronic device, the protection device including a common mode high-impedance element to suppress common mode currents and a capacitor across the high-impedance element to short currents above a predetermined frequency, the high impedance element including a plurality of transformers in series between the first device and the capacitor, the capacitor disposed across the high-impedance element.

2. The system of claim 1, wherein the first electronic device is a pacing device including a set of leads, and the second electronic device is a cardiac stimulator configured to deliver pacing signals to the pacing device.

3. The system of claim 1, wherein the currents induced in the first electronic device include differential mode currents, and the plurality of transformers configured to reduce the differential mode currents.

4. The system of claim 3, wherein each transformer of the one or more transformers includes a toroid core, a first winding around a first portion of the toroid core, and a second winding around a second portion of the toroid core.

5. The system of claim 1, wherein the protection device includes a plurality of capacitors configured to short currents above a predetermined frequency to reduce the currents induced in the first electronic device.

6. The system of claim 1, wherein the protection device includes one or more diodes configured to shunt high voltages away from the second electronic device.

7. The system of claim 1, wherein the protection device includes one or more inductors configured to reduce alternating currents induced in the first electronic device.

8. The system of claim 7, wherein the one or more inductors includes a first inductor coupled to a first lead of the first electronic device and a second inductor coupled to a second lead of the first electronic device, the first and second inductors configured to reduce alternating currents induced in the first and second leads.

9. The system of claim 1, wherein:
   the capacitor includes a first capacitor and a second capacitor each configured to short voltages above a predetermined frequency;
   the plurality of transformers includes a first transformer coupled between the first electronic device and the first capacitor and a second transformer coupled between the first capacitor and the second capacitor; and
   the protection device further includes a set of diodes arranged in parallel with the second capacitor and coupled to the second electronic device, the set of diodes configured to shunt high voltages away from the second electronic device.

10. The system of claim 9, wherein the first and second transformers each are common mode transformers configured to reduce common mode currents induced in the first electronic device.

11. The system of claim 9, wherein one of the first and second transformers is a differential mode transformer configured to reduce differential mode currents induced in the first electronic device, and the other of the first and second transformers is a common mode transformer configured to reduce common mode currents induced in the first electronic device.

12. The system of claim 1, wherein the protection device includes one or more balun circuits configured to reduce common mode currents induced in the first electronic device over a predetermined frequency range.

13. The system of claim 12, wherein the one or more balun circuits includes a plurality of balun circuits each configured to reduce common mode currents induced in the first electronic device over a predetermined frequency range of a set of predetermined frequency ranges, each predetermined frequency range of the set of predetermined frequency ranges at least partially overlapping at least one other predetermined frequency range of the set of predetermined frequency ranges.

14. The system of claim 12, wherein the protection device includes one or more inductors configured to reduce alternating currents induced in the first electronic device, and the one or more balun circuits are coupled between the one or more inductors and the second electronic device.

15. The system of claim 12, wherein at least one balun circuit of the one or more balun circuits includes an inductor in parallel with a capacitor and a resistor.

16. The system of claim 12, wherein at least one balun circuit of the one or more balun circuits includes a coaxial cable winding including first and second conductors, the first conductor coupled to a first lead of the first electronic device and the second conductor coupled to a second lead of the first electronic device.

17. The system of claim 12, wherein the one or more balun circuits includes a plurality of balun circuits connected in series.

18. The system of claim 1, wherein the protection device is further coupled between the first electronic device and the signal generator.

19. The system of claim 1, wherein the protection device is integrated into at least one of the signal generator and the second electronic device.

20. An apparatus, comprising:
   a protection device coupleable between a first electronic device and a second electronic device, the first electronic device disposable near tissue of a subject such that currents can be induced in the first electronic device by voltage pulse waveforms delivered to a set of electrodes near tissue, the protection device including:
   a set of capacitors each configured to short currents above a predetermined frequency to reduce the currents induced in the first electronic device;
   a set of serially coupled transformers each configured to reduce common mode currents or differential mode currents of the currents induced in the first electronic device, wherein a transformer of the set of serially coupled transformers is coupled between two parallel capacitors of the set of capacitors; and a set of diodes configured to shunt high voltages away from the second electronic device.

* * * * *